US007713962B2

(12) United States Patent
Wischik et al.

(10) Patent No.: US 7,713,962 B2
(45) Date of Patent: May 11, 2010

(54) NEUROFIBRILLARY LABELS

(75) Inventors: Claude Michel Wischik, Aberdeen (GB); Charles Robert Harrington, Aberdeen (GB); Janet Elizabeth Rickard, Aberdeen (GB); David Horsley, Aberdeen (GB)

(73) Assignee: Wista Laboratories Ltd., Singapore (SG)

( * ) Notice: Subject to any disclaimer, the term of this patent is extended or adjusted under 35 U.S.C. 154(b) by 0 days.

(21) Appl. No.: 12/071,693

(22) Filed: Feb. 25, 2008

(65) Prior Publication Data
US 2008/0219929 A1    Sep. 11, 2008

Related U.S. Application Data

(63) Continuation of application No. 10/665,008, filed on Sep. 22, 2003, now Pat. No. 7,335,652, which is a continuation of application No. PCT/GB02/01318, filed on Mar. 20, 2002.

(30) Foreign Application Priority Data
Mar. 20, 2001    (GB) ................. 0106953.3

(51) Int. Cl.
*A61K 31/54* (2006.01)
(52) U.S. Cl. ................... 514/224.8; 424/1.1
(58) Field of Classification Search ............. 424/1.11, 424/9.3, 9.4; 514/224.8
See application file for complete search history.

(56) References Cited

U.S. PATENT DOCUMENTS

| 5,008,099 | A | 4/1991 | Quay et al. |
| 5,536,761 | A | 7/1996 | Fujita |
| 6,953,794 | B2 | 10/2005 | Wischik et al. |
| 2006/0014216 | A1 | 1/2006 | Wischik et al. |

FOREIGN PATENT DOCUMENTS

| EP | 0 618 968 B1 | 10/1994 |
| EP | 0747450 A2 | 12/1996 |
| EP | 0 909 814 A2 | 4/1999 |
| EP | 0 911 390 A2 | 4/1999 |
| EP | 0 911 398 A2 | 4/1999 |
| EP | 1 048 302 A2 | 11/2000 |
| JP | 2000-344684 | 12/2000 |
| JP | 2000-344685 | 12/2000 |
| WO | WO 89 03993 | 5/1989 |
| WO | WO 93 01348 | 2/1993 |
| WO | WO 93/03369 A | 2/1993 |
| WO | WO 93 11231 | 6/1993 |
| WO | WO 93/19143 | 9/1993 |
| WO | WO 95/05601 | 2/1995 |
| WO | WO 96/04915 A | 2/1996 |
| WO | WO 96/05837 A | 2/1996 |
| WO | WO 96/30766 | 10/1996 |
| WO | WO 96/30766 A | 10/1996 |
| WO | WO 99/62548 | 12/1999 |
| WO | WO 01/70699 A1 | 9/2001 |
| WO | WO 02/16333 A2 | 2/2002 |
| WO | WO 02/055720 A2 | 7/2002 |
| WO | WO 02/059150 | 8/2002 |
| WO | WO 03/007933 A1 | 1/2003 |
| WO | WO 2005/030676 A1 | 4/2005 |
| WO | WO 2006/032879 A2 | 3/2006 |

OTHER PUBLICATIONS

Peter Friedhoff, Anja Schneider, Ev-Maria, Mandelkow and Eckhard Mandelokow, Rapid Assembly of Alzheimer-like paired helical filament from microtubule-associated protein tau monitored by Fluorescence in solution, Biochemistry, 1998, 37, 10223-10230.*
Aizawa, et al., "Microtubule-binding domain of tau proteins", Journal of Biological Chemistry, 1988, vol. 263, pp. 7703-7707.
Anderton, et al., "Dendritic changes in Alzheimer's disease and factors that may underlie these changes", Prog. Neurobiol., Aug. 1998, 55(6), pp. 595-609.
Bancher, et al., "Accumulation of abnormally phosphorylated Tprecedes the formation of neurofibrillary tangles in Alzheimer's disease", Brain Research, 1989, vol. 477, pp. 90-99.
Biernat, et al., "The switch of tau protein to an Alzheimer-like state includes the phosphorylation of two serine-proline motifs upstream of the microtubule binding region", EMBO Journal Nov. 1992, pp. 1593-1597.
Bobinski, et al., "MRI of entorhinal cortex in mild Alzheimer's disease", The Lancet, Jan. 2, 1999, vol. 353, pp. 38-39.
Bondareff, et al., "Immunohistochemical staging of neurofibrillary degeneration in Alzheimer's disease", Journal of Neuropathology and Experimental Neurology, Mar. 1994, vol. 53, No. 2, pp. 158-164.
Braak, et al., "Alzheimer's disease: transiently developing dendritic changes in pyramidal cells of sector CA1 of the ammon's horn", Acta Neuropathol, 1997, vol. 93, pp. 323-325.
Brandt, et al., "Cytoskeletal mechanisms of axon outgrowth and pathfinding", Cell Tissue Res., 1998, vol. 292, pp. 181-189.
Brion, et al., "Characterization of a partial cDNA specific for the high molecular weight microtubule-associated protein AMP2 that encodes epitopes shared with pared helical filaments of Alzheimer's disease", Dementia, 1990, vol. 1, pp. 304-315.
Caputo, et al., "Amyloid-like properties of a synthetic peptide corresponding to the carboxy terminus of β-amyloid protein precursor", Archives of Biochemistry and Biophysics, 1992, vol. 292, pp. 199-205.

(Continued)

*Primary Examiner*—Michael G Hartley
*Assistant Examiner*—Jagadishwar R Samala
(74) *Attorney, Agent, or Firm*—Foley & Lardner LLP

(57) ABSTRACT

A method for determining the Braak stage of neurofibrillary degeneration associated with a tauopathy in a subject having neurofibrillary degeneration is disclosed. The method comprises the steps of (i) administering to the subject a conjugated, chelated or detectable chemical group-associated ligand that labels aggregated paired helical filament (PHF) tau protein and is capable of crossing the blood brain barrier; (ii) determining the presence and\or amount of ligand bound to extracellular aggregated PHF tau in the medial temporal lobe of the brain of the subject, and (iii) correlating the result of the determination made in (ii) with the extent of neurofibrillary degeneration in the subject. Preferred ligands include sulphonated-benzothiazole-like compounds and diamonophenothiazines.

27 Claims, 54 Drawing Sheets

OTHER PUBLICATIONS

Caputo, et al., "The amyloid proteins of Alzheimer's disease as potential targets for drug therapy", Neurobiology of Aging, vol. 10, pp. 451-461.

Carretero, et al., "Changes in a CSF antigen associated with dementia", Dementia, 1995, vol. 6, pp. 281-295.

Condamines, et al., "New immonassay for the mapping of neurofibrillary degeneration in Alzheimer's disease using two monoclonal antibodies against human paired helical filament tau proteins", Neuroscience Letters, Jun. 9, 1995, vol. 192, No. 2, pp. 81-84.

Database WPI, Section Ch, Week 199228, Derwent Publications, Ltd., London, GB, Class B04, AN, 1992-226472, Jun. 2, 1992.

De Ancos, et al., "Differences in microtubule binding and self-association abilities of bovine brain tau isoforms", The Journal of Biological Chemistry, 1993, vol. 268, No. 11, pp. 7976-7982.

De Garcini, et al., "In vitro conditions for the self-polymerization of the microtubule-associated protein", J. Biochem., 1987, vol. 102, No. 6, pp. 1415-1421.

De Garcini, et al., "Self assembly of microtubule associated protein TAU into filaments resembling those found in Alzheimer disease", Biochemical and Biophysical Research Communications, 1986, pp. 790-797.

De Garcini, et al., "Tau factor polymers are similar to paired helical filaments of Alzheimer's disease", Elsevier Science Publishers B.V., 1988, pp. 150-154.

De Leon, et al, "Frequency of Hippocampal formulation atrophy in normal aging and Alzheimer's disease", Neurobiology of Aging, 1997, vol. 18, No. 1, pp. 1-11.

Detoledo-Morrell, et al., "Alzheimer's disease: in vivo detection of differential vulnerability of brain regions", Neurobiology of Aging, 1997, vol. 18, No. 5, pp. 463-468.

Deture, et al., "In vitro assembly of Alzheimer-like filaments. How a small cluster of charged residues in tau and MAP2 controls filament morphology", Journal of Biological Chemistry, 2002, vol. 277, pp. 34755-34759.

Dezutter et al., "$^{99m}$Tc-MAMA-chrysamine G a probe for beta-amyloid protein of Alzheimer's disease", European Journal of Nuclear Medicine, Nov. 1999, vol. 26, No. 11, pp. 1392-1399.

Eichenbaum, "How Does the Brain Organize Memories", Science, Jul. 18, 1997, vol. 277, pp. 330-332.

Fasulo, et al., "Overexpression of Alzheimer's PHF core tau fragments: implications for the tau truncation hypothesis", Alzheimer's Research 2, 1996, pp. 195-200.

Fox, et al., "Correlation between rates of brain atrophy and cognitive decline in AD", American Academy of Neurology, 1999, pp. 1687-1688.

Fox, et al., "Presymptomatic hippocampal atrophy in Alzheimer's disease", Brain, 1996, vol. 119, pp. 2001-2007.

Friedhoff, et al., "A nucleated assembly mechanism of Alzheimer paired helical filaments", Proc. Natl. Acad. Sci., USA, Dec. 1998, vol. 95, pp. 15712-15717.

Friedhoff, et al., "Rapid Assembly of Alzheimer-like paired helical filaments from microtubule-associated protein tai monitored by fluorescence in solution", Biochemistry, 1998, vol. 37, pp. 10223-10230.

Friedhoff, et al., Rapid Assemby of Alzheimer-like paired Helical Filaments from Microtuble-Associated Protein Tau Monitored by Florescence in Solution, 1998, 37, 10223-10230, *Biochemistry*.

Gertz, et al., "Examination of the validity of the hierarchical model of neuropathological staging in normal aging and Alzheimer's disease", Act Neuropathol., 1998, vol. 95, pp. 154-158.

Gertz, et al., "The relationship between clinical dementia and neuropathological staging (Braak) in a very elderly community sample", Eur. Arch. Psychiatry Clin. Neurosci., 1996, vol. 246, pp. 132-136.

Giannetti, et al., "Fibers of tau fragments, but not full length tau, exhibit a cross β-structure: implications for the formation of paired helical filaments", Protain Science, 2000, vol. 9, pp. 2427-2435.

Goedert, et al., "Cloning and sequencing of the cDNA encoding a core protein of the paired helical filament of Alzheimer disease: Identification as the microtubule-associated protein tau", Proc. Natl. Acad. Sci. USA, Jun. 1988, vol. 85, pp. 4051-4055.

Goedert, et al., "Tau proteins of Alzheimer paired helical filaments: Abnormal phosphorylation of all six brain isoforms", Neuron, Jan. 1992, vol. 8, pp. 159-168.

Grover, et al., "5' splice site mutations in tau associated with the inherited dementia FTDP-17 affect a stem-loop structure that regulates alternative splicing of Exon 10*", The Journal of Biological Chemistry, May 21, 1999, issue, vol. 274, No. 21, pp. 15134-15143.

Grundke-Iqbal, et al., "Abnormal phosphorylation of microtubule-associated protein T (tau) in Alzheimer cytoskeletal patholoy", Proc. Natl. Acad. Sci. USA, 1986, vol. 83, pp. 4913-4917.

Hagestedt, et al., "Tau protein becomes long and stiff upon phosphorylation: correlation between paracrystalline structure and degree of phosphorylation", The Journal of cell biology, 1989, vol. 109, pp. 1643-1651.

Harrington, et al., "Competitive ELISA for the measurement of tau protein in Alzheimer's disease", Journal of Immunological Methods, 1990, vol. 134, pp. 261-271.

Harrington, et al., "Measurement of distinct immunochemical presentations of tau protein in Alzheimer's disease", Proc. Natl. Acad. Sci., Jul. 1991, vol. 88, pp. 5842-5846.

Hodges, et al., "What and how: evidence for the dissociation of object knowledge and mechanical problem-solving skills in the human brain", Proc. Natl. Acad. Sci. USA, Aug. 1999, vol. 96, pp. 9444-9448.

Hutton, et al. "Association of missense and 5'-splice-site mutations in tau with the inherited dementia FTDP-17", Nature, Jun. 18, 1998, vol. 393, pp. 702-705.

Ibanez, et al., "Regional glucose metabolic abnormalities are not the result of atrophy in Alzheimer's disease", Neurology 50, Jun. 1998, pp. 1585-1593.

Imamura, et al., "Regional cerebral glucose metabolism in dementia with Lewy bodies and Alzheimer's disease: a comparative study using positron emission tomography," Neuroscience Letters 235, 1997, pp. 49-52.

Ishiguro, et al., "A novel tubulin-dependent protein kinase forming a paired helical filament epitope on tau", J. Biochem, 1988, vol. 104, pp. 319-321.

Ishiguro, et al., "A serine/threonine proline kinase activity is included in the tau protein kinase fraction forming a paired helical filament epitope", Neuroscience Letters, 1991, vol. 128, pp. 195-198.

Ishiguro, et al., "Phosphorylation sites on tau by tau protein kinase I, a bovine derived kinase generating an epitope of paired helical filaments", Neuroscience Letters, 1992, vol. 148, pp. 202-206.

Ishiguro, et al., "Tau protein kinase I converts normal tau protein into A68-like component of paired helical filaments", Journal of Biological Chemistry, 1992, vol. 267, pp. 10897-10901.

Ishii, et al., "Regional cerebral glucose metabolism in dementia with Lewy bodies and Alzheimer's disease", Neurology 51, Jul. 1998, pp. 125-129.

Jack, et al., "Medial temporal atrophy on MRI in normal aging and very mild Alzheimer's disease", American Academy of Neurology, Sep. 1997, pp. 786-794.

Jakes, et al., "Identification of 3- and 4-repeat tau isoforms within the PHF is Alzheimer's disease", The EMBO Journal, 1991, vol. 10, No. 10, pp. 2725-2729.

Janciauskiene, et al., "In vitro amyloid fibril formulation from α1-antitrypsin", Bio Chem, 1995, vol. 375, pp. 103-109.

Johnson, et al., "Preclinical prediction of Alzheimer's disease using SPECT", American Academy of Neurology 50, Jun. 1998, pp. 1563-1571.

Juottonen, et al., "Major decrease in the volume of the entorhinal cortex in patients with Alzheimer's disease carrying the apolipoprotein E ∈4 allele", J Neurol. Neurosurg Psychiatry, 1998, vol. 65, pp. 322-327.

Klymkowsky, "Weaving a tangled web: the interconnected cytoskeleton", Nature Cell Biology, 1999, vol. 1, No. 5, p. E121.

Ksiezak-Reding et al., "Structural stability of paired helical filaments requires microtubule-binding domains of tau: A model for self-association", Neuron, 1991, vol. 6, pp. 717-728.

Ksiezak-Reding et al., "Mass and physical dimensions of two distinct populations of paired helical filaments", Neurobiology of Aging, 1994, vol. 15, No. 1, pp. 11-18.

Ksiezak-Reding, "Assembled tau filaments differ from native paired helical filaments as determined by scanning transmission electron microscopy", STEM, 1998, pp. 86-98.

Kuller, et al., "Relationship between ApoE, MIR findings, and cognitive function in the cardiovascular health study", Stroke, 1998, vol. 29, pp. 388-398.

Lai, "The role of abnormal phosphorylation of tau protein in the development of neurofibrillary pathology in Alzheimer's disease", Christ's College, 1994, pp. 1-243.

Lai, et al., "Examination of phosphorylated tau protein as a PHF-precursor at early stage Alzheimer's disease", Neurobiology of Aging, 1995, vol. 16, No. 3, pp. 433-445.

Lakmache, et al, "Interhemispheric disconnection syndrome in Alzheimer's disease", Proc. Natl. Acad. Sci. USA, 1998, vol. 95, pp. 9042-9046.

Ledesma, et al., "Implication of brain cdc2 and MAP2 kinases in the phosphorylation of tau protein in Alzheimer's disease", FEBS, 1992, vol. 308, No. 2, pp. 218-224.

Lee et al., "A68: A major subunit of paired helical filaments and derivatized forms of normal tau", Science, 1991, vol. 251, pp. 675-678.

Lehtovirta, et al., "Longitudinal SPECT study in Alzheimer's disease: relation to apolipoprotein E polymorphism", J Neurol. Neurosurg Psychiatry, 1998, vol. 64, pp. 742-746.

Lewis, et al., "Microtubule-associated protein MAP2 shares a microtubule binding motif with tau protein", Science, 1988, vol. 242, pp. 936-939.

Lichtenberg-Kraag, et al., "Alzheimer-type phosphorylation of microtubule-associated protein tau in vitro", 1991/92.

Lichtenberg-Kraag, et al., "Phosphorylation-dependent epitopes of neurofilament antibodies on tau protein and relationship with Alzheimer tau", Proc. Natl. Acad. Sci. USA, 1992, vol. 89, pp. 5384-5388.

Lomas, et al., "The mechanism of Z $\alpha$1-antitrypsin accumulation in the liver", Nature, 1992, vol. 357, pp. 605-607.

Marin, et al., "The relationship between apolipoprotein E, dementia, and vascular illness", Atherosclerosis 140, 1998, pp. 173-180.

Mena, et al., "A progressive deposition of paired helical filaments (PHF) in the brain characterizes the evolution of dementia in Alzheimer's disease", Journal of Neuropathology and Experimental Neurology, 1991, pp. 474-490.

Mena, et al., "Monitoring pathological assembly of tau and $\beta$3-amyloid proteins in Alzheimer's disease", Acta Neuropathol, 1994, pp. 50-56.

Minoshima, et al., "Metabolic reduction in the posterior cingulate coretex in very early Alzheimer's disease", Annals. Neurology, Jul. 1997, vol. 42, No. 1, pp. 85-93.

Mori, et al., "Premorbid brain size as a determinant of reserve capacity against intellectual decline in Alzheimer's disease", Am. J. Psychiatry, Jan. 1997, vol. 154, No. 1, pp. 18-24.

Mukaetova-Ladinkska, et al., "Staging of cytoskeletal and beta-amyloid changes in human isocortex reveals biphastic synaptic protein response during progression of Alzheimer's disease", American Journal of Pathology, Aug. 2000, vol. 157, No. 2, pp. 623-636.

Nagy, et al., "Relationship between clinical and radiological diagnostic criteria for Alzheimer's disease and the extent of neuropathology as reflected by 'stage': a prospective study", Dementia and Geriatric Cognitive Disorders, 1999, vol. 10, pp. 109-114.

Novak, et al., Molecular characterization of the minimal protease resistant tau unit of the Alzheimer's disease paired helical filament, The EMBO Journal, 1993, vol. 12, No. 1, pp. 365-370.

Pedrotti, et al., "Interactions of microtubule-associated protein MAP2 with unpolymerized and polymerized tubulin and actin using a 96-well microtiter plate solid-phase immunoassy", Biochemistry, 1994, vol. 33, pp. 8798-8806.

Perez, et al., "In vitro assembly of tau protein: Mapping the regions involved in filament formation", Biochemistry, 2001, vol. 40, 5983-5991.

Perez-Tur, et al., "Neurodegenerative disease of Guam: Analysis of TAU", American Academy of Neurology, 1999, vol. 53, pp. 411-412.

Poulter, et al., "Locations and immunoreactivities of phosphorylation sites on bovine and porcine tau proteins and a PHF-tau fragment", The Journal of Biological Chemistry, 1993, vol. 268, No. 13, pp. 9636-9644.

Raul, et al., "Staging the pathological assembly of truncated tau protein into paired helical filaments in Alzheimer's disease", Acta Neuropathologica, 1996, vol. 91, No. 6, pp. 633-641.

Resch, et al., "Design and Synthesis of a Potential Affinity/Cleaving Reagent for Beta-Pleated Sheet Protein Structures", Bioorganic & Medical Chemistry Letters, vol. 1, No. 10, pp. 519-522 1991.

Sato-Harada, et al., "Microtubule-associated Proteins Regulate Microtubule Function as the Track for Intracellular Membrane Organelle Transports", Cell Structure Function 21, 1996, pp. 283-295.

Schneider, et al., "Phosphorylation that detaches tau protein from microtubules (Ser262 Ser214) also protects it against aggregation into Alzheimer paired helical filaments", Biochemistry, 1999, vol. 38, pp. 3549-3558.

Shogi-Jadid, et al., Localization of Neurofibrillary Tangles and Beta-Anyloid Plaques in the Brains of Living Patients with Alzheimer Disease, Am. J. Geriatr. Psychiatry, 10:1, Jan.-Feb. 2002, pp. 24-35.

Smith, et al., "The molecular pathology of Alzheimer's disease: are we any closer to understanding the neurodegenerative process?", Neuropathology and Applied Neurobiology, Blackwell Scientific Publications, London, GB, Aug. 1, 1994, vol. 20, No. 4, pp. 322-338.

STF File CA, Abstract 120: 11510 & WO 931019143 (Lord Corporation) Sep. 30, 1993, CAS Registry No. 56915-59-3 found at the website: stneasy.cas.org.

STF File CA, Abstract 122: 163754 & US 5,536,761 A (Fujita, H.) Jul. 16, 1996, CAS Registry No. 5915-59-3 found at the website: stneasy.cas.org.

STF File CA, Abstract 126: 76133 & EP 0747450 (Bayer Corporation) Dec. 11, 1996, CAS Registry No. 18532-01-1 found at the website:stneasy.cas.org.

Styren, et al., "X-34, a fluorescent derivative of congo red: a novel histochemical stain for Alzheimer's disease pathology", The Journal of Histochemistry and Cytochemistry, 2000, vol. 48, No. 9, pp. 1223-1232.

Van Rossum, et al., "Cytoskeletal dynamics in dendritic spines: direct modulation by glutamate receptors", Trends Neurosci., 1992, vol. 22, pp. 290-295.

Villareal, et al., "The diagnosis of Alzheimer's disease", Alzheimer's Disease Review 3, 1998 pp. 142-152.

Von Bergen, et al. "Assembly of tau protein into Alzheimer's paired helical filaments depends on a local sequence motif forming beta structure", Proceedings of the National Academy of Sciences of USA, National Academy of Science, May 9, 2000, vol. 97, No. 10, pp. 5129-5134.

Wille, "Alzheimer-like paired helical filaments and antiparallel dimers formed from microtubule-associated protein tau in vitro", J. Cell Biol., 118, 1992, pp. 573-584.

Willingham, "Systems of memory in the human brain", Neuron., Jan. 1997, vol. 18, pp. 5-8.

Wischik et al., "Selective Inhibition of Alzheimer Disease-Like Tau Aggregation by Phenothiazines," 1996, 93, 11213-11218, Proc. Nat. Acad. Sci. USA.

Wischik, "Cell biology of the Alzheimer tangle", Current Opinion in Cell Biology, 1989, vol. 1, pp. 115-122.

Wischik, "Molecular neuropathology of Alzheimer's disease" 1989, pp. 44-70.

Wischik, "Molecular neuropathology of Alzheimer's disease", John Libbey & Co., 1991, pp. 239-250.

Wischik, et al., "Author's response to commentaries", Neurobiology of Aging, 1995, vol. 16, No. 3, pp. 423-431.

Wischik, et al., "Isolation of a fragment of tau derived from the core of the paired helical filament of Alzheimer disease", Proc. Natl. Acad. Sci. USA, 1988, vol. 85, pp. 4506-4510.

Wischik, et al., "Modelling prion-like processing of tau protein in Alzheimer's disease for pharmaceutical development", pp. 185-241.

Wischik, et al., "Quantitative analysis of tau protein in paired helical filament preparations" Implications for the role of tau protein phosphorylation in PHF assembly in Alzheimer's disease, Neurobiology of Aging, 1995, vol. 16, No. 3, pp. 409-431.

Wischik, et al., "Selective inhibition of Alzheimer disease-like tau aggregation by phenothiazines", Proc. Natl. Acad. Scie. USA, 1996, vol. 93, pp. 11213-11218.

Wischik, et al., "Structural characterization of the core of the paired helical filament of Alzheimer disease", Proc. Natl. Acad. Sci. USA, 1988, vol. 85, pp. 4884-4888.

Wischik, et al., "Structure, biochemistry and molecular pathogenesis of paired helical filaments in Alzheimer's disease", Pathbiology of Alzheimer's Disease, 1995, pp. 10-39.

Wischik et al., "Subunit structure of paired helical filaments in Alzheimer's disease", The Journal of Cell Biology, 1985, vol. 100, pp. 1905-1912.

Wischik, et al., "The role of tau protein in the neurodegenerative dementias", Dementia $2^{nd}$ edition pp. 461-492, J (EDT)/Ames D (EDT)/Burns, A (EDT)/Levy, R/Publisher: Hodder Arnold Published Feb. 2001.

Wischik, et al., "The molecular basis of tau protein pathology in Alzheimer's disease and related neurodegenerative dementias", in Neurobiology of Alzheimer's Disease (Eds. D. Dawbarn & S.J. Allen) Oxford University Press, Oxford, pp. 103-206.

Wischik, Thesis "The structure and biochemistry of paired helical filaments in Alzheimer's disease", Part I and II, pp. 1-455.

Yens, et al., "Alzheimer's neurofibrillary tangles contain unique epitopes in common with the heat-stable microtubule-associated proteins tau and MAP2", American Journal of Pathology, 1987, vol. 126, pp. 81-91.

* cited by examiner

Diamino phenothiazines with varying methyl groups

Synthesis of [¹¹C] labelled Methylene Blue

Synthesis of [$^{11}$C] labelled Azure B

Synthesis of [$^{18}$F] labelled

Primulin

Benzothiazole analogue

Thiazin yellow

DENSITY OF AT8-T'S BY REGION AND STAGE

Preparation 1 dGA 5 mcg/ml, dGAE 5 mcg/ml

Preparation 2 dGA 4 mcg/ml, dGAE 5 mcg/ml

Preparation 1 dGA 5 mcg/ml, dGAE 5 mcg/ml

Preparation 2 dGA 10 mcg/ml, dGAE 10 mcg/ml

Preparation 1

Preparation 2 primulin thiazin red

Tau-Tau Binding at 5 mcM DMMB

Tau-Tau Binding at 5 mcM DMMB

Tau-Tau Binding at 15 mcM DMMB

Tau-Tau Binding at 15 mcM DMMB

NEUROFIBRILLARY LABELS

CROSS-REFERENCE TO RELATED APPLICATION

This application is a continuation of U.S. patent application Ser. No. 10/665,008, filed on Sep. 22, 2003, now U.S. Pat. No. 7,335,652 which is a continuation of International Application PCT/GB02/01318, filed on Mar. 20, 2002.

FIELD OF THE INVENTION

The present invention concerns materials, methods and models relating generally to the labelling and detection of neurofibrillary tangles. In addition, it concerns the identification and development of ligands suitable for neuropathological staging and their use in the diagnosis, prognosis or treatment of diseases such as Alzheimer's Disease (AD).

BACKGROUND TO THE INVENTION

Neuropathological Staging and AD

The neuropathological staging proposed by Braak (Braak, H et al. (1991), Acta. Neuropathol. 82, 239-259) provides the best available definition of progression of relatively pure neurofibrillary degeneration of the Alzheimer-type which is diagnostic of AD (Wischik et al. (2000), "Neurobiology of Alzheimer's Disease", Eds. Dawbarn et al., The Molecular and Cellular Neurobiology Series, Bios Scientific Publishers, Oxford). This staging is shown schematically in terms of brain region in FIG. 2B, and is based on a regular regional hierarchy of neurofibrillary tangle (NFT) distribution. Regions of the brain which appear earlier in the hierarchy have both more tangles and are affected in less severe cases than those later in the list.

Relationship Between AD, Clinical Dementia and Neuropathological Staging

The provision of an effective pre-mortem assessment of Braak Stage would be of use in the assessment and treatment of AD, for which the differential includes Lewy Body dementia, Parkinson's disease, various forms of fronto-temporal and cortico-basal degeneration, progressive supranuclear palsy and a range of rare neurological syndromes.

The original model proposed by Braak was essentially qualitative in nature, and was not linked to any implications about the threshold for development of clinical dementia and symptoms.

In terms of the appearance of clinical dementia by DSM-IV criteria, this corresponds statistically to the transition between Braak stages 3 and 4 (FIG. 2c). The DSM-IV criteria (Diagnostic and Statistical Manual of Mental Disorders, 4$^{th}$ Edition, American Psychiatric Association, American Psychiatric Press, Washington D.C. (1994)) for the definition of dementia equate to an MMSE (Mini-Mental State Examination) cut-off point of about 18, and corresponds to a dementia prevalence of about 5% of the population over-65 years old (over-65's represent about 17% of the total population).

Gertz et al. ((1996) Eur. Arch. Psychiatry Clin. Neurosci. 246, 132-6)) studied cases followed from general practice to post-mortem, which were rigorously characterised at the clinical level using CAMDEX (Roth et al, 1988, "The Cambridge Examination for Mental Disorders of the Elderly (CAMDEX)" Cambridge University Press). These were staged post-mortem by the criteria of Braak and, after excluding all cases with any degree of vascular pathology found post-mortem, there remained uncertainty in about one third of cases at the point of transition. That is, about one third of cases with a clinical diagnosis of AD are actually at early Braak stages (stages 1-3), have vascular pathology, or have concomitant Lewy body pathology. Thus there exists a high degree of uncertainty, even in the best practice research setting. The predominant neuropathological substrate that is actually present when a routine clinical diagnosis of AD is made is even more uncertain.

It has recently been reported that a molecule (PDDNP, 2-(1-{6-[(2-[$^{18}$F]fluoroethyl)(methyl)amino]-2-naphthyl}ethylidene)malononitrile) demonstrates increased relative retention time (RRT) in medial temporal lobe brain regions (hippocampus, entorhinal cortex and amygdala) following injection and PET imaging in cases with a clinical and neuroradiological diagnosis of Alzheimer's disease (Shoghi-Jadid et al., Am. J. Geriatr. Psychiatr. 2002, 10:24-35).

Although binding to NFTs and amyloid plaques is discussed, no binding to NFTs is shown, although the compound does bind with high affinity to synthetic beta-amyloid fibrils in vitro.

When cases were matched for corresponding disease severity by MMSE score with a neuropathological case series in which vascular pathology was excluded, the RRT values reported by Shoghi-Jadid et al. were found to correlate with beta-amyloid plaque counts but not with measures of neurofibrillary tangle pathology, as shown below.

Spearman Rank Correlation Coefficients:

|     | MTL AP  | Global AP | MTL NFT | Global NFT |
| --- | ------- | --------- | ------- | ---------- |
| RRT | 0.665** | 0.654**   | 0.244   | 0.189      |
| p   | <0.01   | <0.01     | >0.1    | >0.1       |

Pearson Correlation Coefficients:

|     | MTL AP | Global AP | MTL NFT | Global NFT |
| --- | ------ | --------- | ------- | ---------- |
| RRT | 0.602* | 0.596*    | 0.266   | 0.275      |
| p   | <0.05  | <0.05     | >0.3    | >0.3       |

Where the parameters are defined as follows:

| | |
|---|---|
| MTL AP | medial temporal lobe amyloid plaques |
| Global AP | average amyloid plaque load in 12 brain regions |
| MTL NFT | medial temporal lobe neurofibrillary tangles |
| Global NFT | average NFT load in 12 brain regions |

However, beta-amyloid deposition is known to discriminate poorly between normal aging and Alzheimer's disease (see FIG. 2d herein), and beta-amyloid pathology does not provide a sound basis for neuropathological staging (Braak and Braak, 1991). Therefore, FDDNP-RRT does not provide a method for in vivo neuropathological staging of Alzheimer's disease.

Although it is possible that further refinement in clinical methods with particular reference to more specific neuropsychological indicators (e.g. split attention tasks, delayed matching to sample, etc.) may improve the accuracy of clinical diagnosis, an essential problem is to develop methods for the direct measurement of underlying neuropathology during life, in particular the extent of neurofibrillary degeneration of the Alzheimer-type.

Progression of Neurofibrillary Degeneration and Tau

As described above, the tau-based pathology of AD is a major feature of the phenotype. It is highly correlated with extent of neuronal destruction (reviewed in Wischik et al. (2000) loc cit).

On a cellular basis, the formation of NFTs from Tau is believed to proceed as follows. In the course of their formation and accumulation, paired helical filaments (PHFs) first assemble as filaments within the cytoplasm, probably from early tau oligomers which become truncated prior to, and in the course of, PHF assembly (Refs 26, 27). They then go on to form classical intracellular NFTs. In this state, PHFs consist of a core of truncated tau and a fuzzy outer coat containing full-length tau (Wischik et al. (2000) loc. cit.). The assembly process is exponential, consuming the cellular pool of normal functional tau and inducing new tau synthesis to make up the deficit (Ref 29). Eventually functional impairment of the neurone progresses to the point of cell death, leaving behind an extracellular NFT. Cell death is highly correlated with the number of extracellular NFTs (Bondareff, W. et al. (1993) Arc. Gen. Psychiatry 50: 350-6). As the outer neuronal membrane is damaged and NFTs are extruded into the extracellular space, there is progressive loss of the fuzzy outer coat of the neurone with corresponding loss of N-terminal tau immunoreactivity, but preservation of tau immunoreactivity associated with the PHF core (FIG. 3; Ref 30).

In the process of aggregation, tau protein undergoes a conformational change in the repeat domain associated with a half-repeat phase-shift (Refs 32, 33). This creates a proteolytically-stable fragment which is identical to that found in the core of the paired helical filaments (PHFs) which constitute the neurofibrillary tangles characteristic of AD. By analogy with other protein aggregation systems, the process most likely involves an alpha-helix to beta-strand change in conformation (reviewed in Wischik et al. (2000) loc. cit.).

Generally speaking therefore, the aggregation of tau can be considered in 3 stages: intracellular oligomers; intracellular filaments (stage 1 of FIG. 3); extracellular filaments (stages 2 & 3 of FIG. 3).

However, to date, no definitive correlation has been established between these stages, which occur at the cellular level, and possibly at different rates and probabilities in different regions in the brain, and the progression of pathology according to the defined hierarchical system of Braak and Braak which, as discussed above, is the best available definition of progression of relatively pure neurofibrillary degeneration.

Invasive Methods for Assessing AD

Lumbar-puncture CSF measurements enable discrimination between AD and controls, and between AD and other neurological disorders, but lumbar-puncture is more invasive then nuclear medicine-based approaches, and carries a higher risk (Refs. 17 to 21). EEG-neurological diagnosis has also been developed (Refs 22-25), but in this regard there remains a need for cheap instrumentation which can be used at the point of clinician contact.

Neurofibrillary Degeneration Via Brain Atrophy —SPECT and PET

Numerous studies have shown that global brain atrophy and specific medial temporal lobe atrophy, particularly of the hippocampus, are closely linked to underlying neurofibrillary degeneration of the Alzheimer-type, and are valuable in the early diagnosis of AD (Refs 1-8).

However, although the diagnosis of AD by monitoring global brain atrophy represents a methodology which can be made to work in a research setting, there are difficulties in defining and measuring atrophy in specific brain regions, and likewise in the measurement of global neocortical atrophy. In any case, a diagnosis based on detectable atrophy may come too late for effective treatment.

There have been advances in diagnostic methodology in recent years, following the identification of diagnostic features in SPECT scans (Refs 9-12; characteristic patterns of perfusion defect detected by HMPAO SPECT), PET scans (Refs 13-15; metabolic defect detected by glucose metabolism profile) and MRI scans (Ref 16; global brain atrophy, specific patterns of lobar atrophy). Of these, the most generally accessible are MRI and SPECT, since PET is for the present time limited to centres which have local specialised cyclotron and radiochemistry capability for the preparation of short half-life injectable radioligands (Aberdeen, London, Cambridge in UK). Notably, the characteristic early stage temporo-parietal perfusion defect detected by HMPAO SPECT in patients with AD corresponds very closely to the pattern of tau pathology which can be detected biochemically (FIG. 1). The biochemical changes precede overt neurofibrillary degeneration as seen by the appearance of NFTs (FIG. 2; Mukaetova-Ladinska et al., 2000 Am. J. Pathol. Vol. 157, No. 2, 623-636).

However, although MRI and SPECT scans are useful for detecting specific patterns of perfusion defects characteristic of AD, discrimination between different neuropathological stages, or between AD and other types of dementia, is difficult.

For instance, SPECT is useful for detection of a specific pattern of bilateral temporo-parietal perfusion defect that is characteristic of AD (Refs 9-11), which can be useful even at very early stage disease. However, SPECT changes discriminate neuropathological stages poorly (Ref 12). Furthermore, discrimination between AD and Lewy Body dementia is difficult. Both have a bilateral temporo-parietal perfusion defect, but only in the latter does an occipital perfusion defect tend to be present. The same patterns of defect can be demonstrated using PET measurement of glucose metabolism (Refs 1315), but the problem of distinguishing Lewy Body dementia persists in this modality.

Thus, as can be inferred from data in Ref 12, the probability of successful SPECT detection of cases at Braak stages 1&2 is 50%, and at stages 3&4 is 60%. It is only at stages 5&6 that 95% of cases become SPECT-positive. Conversely, cases detected as SPECT-positive could be at stages 1&2 (20%), 3&4 (20%), or 5&6 (60%). SPECT will therefore fail to detect 40-50% of the pre-stage 4 target population for early diagnosis and therapeutic intervention. In a further study (data not shown) it was shown that overall agreement between SPECT diagnosis and clinical diagnosis was of the order of 50%.

Thus, in developing a treatment aimed specifically at preventing neurofibrillary degeneration of the Alzheimer-type, there is a critical need to develop, in parallel, non-invasive means of selecting patients for treatment, and monitoring their response to the treatment, according to a defined and reproducible definition of disease progression.

DISCLOSURE OF THE INVENTION

Brief Summary of the Invention

The present inventors have used immunochemical properties (Refs 26, 27, 30) to distinguish intracellular tangles from extracellular tangles. Both the frequency of cases with tangles in these categories (i.e. probability) and their quantity (i.e. counts per mm$^2$) were determined in a prospective case series and grouped into the regions of the brain known to represent stages in the progression of pathology according to the system of Braak and Braak.

As described in more detail below, these antibody studies demonstrate for the first time that by employing extracellular vs. intracellular specificity, in defined brain regions, deposits of PHF-tau provide a basis for empirical staging of the neurofibrillary degeneration of AD.

Thus in one aspect, the present invention provides a method for determining the stage of neurofibrillary degeneration associated with tauopathy (e.g. AD) in a subject believed to suffer from the disease, which method comprises the steps of:
(i) introducing into the subject a ligand capable of labelling aggregated PHF tau,
(ii) determining the presence and\or amount of ligand bound to extracellular aggregated PHF tau in the medial temporal lobe of the brain of the subject,
(iii) correlating the result of the determination made in (ii) with the extent of neurofibrillary degeneration in the subject.

As described in the introduction, progression of neurofibrillary degeneration is definitive of the neuropathological staging proposed by Braak, which in turn is the best available neuropathological definition of progression of AD. The methods of the present invention can thus be used to provide an actual Braak stage result. In preferred embodiments they can be used to diagnose patients at early Braak stages (e.g. Braak stage 2) even before clinical symptoms may be readily apparent—such diagnosis can be used to direct timely treatment and advice.

Interestingly, results shown in Gertz et al. (1996) loc cit, based on immunological detection of NFTs, but which did not distinguish extracellular and intracellular tangles, showed little difference between the numbers detected in demented (generally Braak stage 4-6) and non-demented (generally Braak stage 1-3) subjects in medial temporal lobe structures (see FIG. 1 and Table 2, page 134 therein; the relevant structures are labelled Pre alpha ent., CA1, Pri Ento.). Thus the correlation demonstrated by the present invention is particularly surprising.

The invention further provides novel ligands for use in labelling tau aggregates, plus also novel screens for discovering such ligands.

Some of the aspects of the invention discussed above will now be dealt with in more detail.

Choice of Subject

Suitable subjects for the method may be selected on the basis of conventional factors. Thus the initial selection of a patient may involve any one or more of: rigorous evaluation by experienced clinician; exclusion of non-AD diagnosis as far as possible by supplementary laboratory and other investigations; objective evaluation of level of cognitive function using neuropathologically validated battery.

Ligands

The ligand is capable of labelling aggregated PHF tau, the formation of which is discussed above. It may specifically or preferentially bind such tau (preferentially with respect to competing binding sites present in the relevant region of the brain). Suitable ligands (including novel ligands) and methods of identifying them are discussed below.

More specifically, the disclosure that Braak staging can be assessed on the basis described herein has significant implications for the choice and\or development of ligands for use in diagnostic labelling. Immunological methods suffer from the drawback that antibodies do not readily cross the blood-brain barrier in a quantitative manner, and furthermore, the method may be clinically unsuitable since adverse reactions may be triggered by the injection of antibodies into the body for this purpose. It is consequently difficult to discriminate between different stages of tau aggregation on the basis of differential patterns of immunoreactivity in living subjects.

The present inventors have therefore investigated the critical chemical characteristics of compounds which bind to neurofibrillary tangles. They provide herein a minimal chemical structure required for binding which has implications, inter alia, in the development and use of compounds as ligands of neurofibrillary tangles and such processes, uses and compounds form further aspects of the invention.

Preferred ligands, including novel ligands, are disclosed in more detail hereinafter, but may include in particular sulphonated-benzothiazole-like compounds (see e.g. FIG. 4a) and diaminophenothiazines (see e.g. FIG. 8) as well as other mimetic compounds sharing an appropriate minimal chemical structure with either of these. Compositions comprising, or consisting of, combinations of the ligands disclosed herein (preferably distinguishable ligands e.g. in terms of labelling) and\or combinations of ligands with blocking agents (see below) form various aspects of the invention.

Binding to Extracellular Tau

The determination of (ii) above is made based on extracellular aggregated tau. In general terms, for the purposes of the present invention, this may be determined from extracellular tangles (see e.g. Refs 26, 27 and Examples, Methods and Materials, Table).

It has previously been shown from histological studies that, during the course of aggregation, tau protein acquires binding sites for compounds such as thiazin red and thioflavin-S (Refs 26, 27). The binding site can be shown to exist within the tangle itself, and not in extraneous proteins (Ref 34). Thus both intracellular and extracellular tangles are labelled to some extent by such ligands, as judged histologically.

In general terms, the probability or amount of extracellular binding sites (as opposed to total binding sites, or intracellular sites) may be determined either by using ligands which are too large to gain ready intracellular access, or ligands which can act intracellularly, but at a defined (relatively lower) concentration at which extracellular action is favoured.

Large chelated ligands, such as those susceptible to detection by SPECT, could be expected to at least reach and bind appropriate extracellular targets. Compounds labelled directly for PET could potentially detect both intracellular or extracellular targets, with the latter being favoured at low concentration. Thus the work of the present inventors shows that both of these detection methods have potential in Braak staging, when used with an appropriate tangle-binding ligand. Nevertheless, in the light of the present disclosure, it will be appreciated that in order to conveniently assess Braak stage via NFT numbers it may be important to employ ligands which are not only capable of crossing the blood brain barrier and labelling specified extracellular or intracellular deposits of aggregated tau, but preferably can also retain this property when conjugated to further compounds.

However, for the avoidance of doubt, ligands may be visualised or detected by any suitable means, and the skilled person will appreciate that any suitable detection means as is known in the art could be substituted for these examples.

Enhancement of Preferential Tau Binding

In one embodiment of the invention, steps (i) and\or (ii) of the method are performed in conjunction with (preferably preceded by) the further step of introducing into the subject a second ligand which labels competing (i.e. non-aggregated tau) binding sites present in the relevant region of the brain preferentially to the first ligand.

Thus the methods and other embodiments herein may include a step:

(ibis) introducing into the subject a blocking ligand which labels non-aggregated tau binding sites in the brain of the subject preferentially to the ligand capable of labelling aggregated PHF tau.

A competing binding site may be one which is provided by e.g. amyloid plaques, such as may be present in the subject. By introducing such second ligands into the subject, the relative or effective concentration of first ligand available to bind to aggregated tau may be enhanced. Suitable second ligands (or blocking compounds as they may be described herein) are described below, but they may in particular include benzthiazoles such as are shown in FIG. 5, compounds 1B and 2. Another suitable blocking ligand may be FDDNP of Shoghi-Jadid et al., Am. J. Geriatr. Psychiatr. 2002, 10:24-35, discussed above.

Brain Regions

The significance of the medial temporal lobe i.e. E2/Trans (Entorhinal cortex layer 2/transitional entorhinal cortex) and E4/HC (Entorhinal cortex layer 4 and hippocampus) regions, and also neocortical structures (FIT/P regions—frontal, temporal, parietal) of the brain are demonstrated in FIGS. 25, 27, and 29.

In one embodiment, the method comprises only analysing the data based on extracellular NFTs in the medial temporal lobe.

If a further embodiment, both this region and the neocortical structure data is assessed. In the latter case it may be preferable to assess intracellular PHF deposits.

Thus the methods and other embodiments herein may include a further step:

(iib) additionally determining the presence and\or amount of ligand bound to intracellular aggregated PHF tau in a neocortical structure of the brain of the subject, This may be followed by:

(iii) correlating the result of the determination made in (ii) and optionally (iib) with the extent of neurofibrillary degeneration in the subject, and hence the AD state of the subject.

The ligand used for intracellular labelling may in principle be the same as that used for extracellular labelling, but preferably will be different and\or labelled distinctively (such that it can be distinguished by whatever imaging process is being used).

The additional steps may be particularly preferred for assessing or confirming neurofibrillary degeneration in subjects at Braak stage 2-6.

Determination of Neurofibrillary Degeneration

The determination may be of the presence of binding in a given area. This determination can then be related to a normal range of values for cases without any pathology (i.e. cases putatively at Braak Stage 1), or ranges of reference values which have been determined for successive Braak stages to determine the neuropathological stage corresponding to the given determination. The correlation may be done by means of a look-up table or graph, e.g. based on data corresponding to the Figures and Table 1 in Example 1 herein for density. Alternatively, a given determination may be related with reference to a given threshold value to a probability of a case being at a Stage more advanced that Stage 1 (e.g. based on data corresponding to the Figures herein for probability), and thereby giving a probability of correctly attributing a diagnosis of Alzheimer's disease.

Uses of the Method

The determination may be as part of a method of diagnosis or prognosis. It may be used to select a patient for treatment, or to assess the effectiveness of a treatment or a therapeutic e.g. an inhibitor of tau-tau association administered to the subject.

Thus embodiments of the invention include:

A ligand which is capable of labelling extracellular aggregated PHF tau for use in a method of diagnosis or prognosis of AD in a subject believed to suffer from the disease, which method comprises the steps of:

(i) introducing into the subject a ligand capable of labelling aggregated PHF tau, (ii) determining the presence and\or amount of ligand bound to extracellular aggregated PHF tau in the of the medial temporal lobe of the brain of the subject, (iii) correlating the result of the determination made in (ii) with the extent of neurofibrillary degeneration in the subject, and hence the AD state of the subject.

Use of a ligand which is capable of labelling extracellular aggregated PHF tau in a method for preparing a diagnostic or prognostic reagent suitable for use in a method of determining the stage of neurofibrillary degeneration associated with AD in a subject believed to suffer from the disease, which method comprises the steps of:

(i) introducing into the subject said reagent which is capable of labelling aggregated PHF tau, (ii) determining the presence and\or amount of the reagent bound to extracellular aggregated PHF tau in the medial temporal lobe of the brain of the subject, (iii) correlating the result of the determination made in (ii) with the extent of neurofibrillary degeneration in the subject.

In a still further aspect, the invention provides a kit for performing the uses and methods described above, the kit comprising one or more ligands or derivatives as provided herein, which are capable of binding to the aggregated molecules. It may include means for increasing the detectability of such compounds e.g. a technetium chelating group, plus optionally means to conjugate this to the ligand, plus optionally technetium. Where the kit comprises a derivative of a compound as disclosed herein, this may be e.g. fluoroscopically detectable, as discussed elsewhere in this description. The kit may also include means for detecting or visualising the ligand, e.g. where the ligand has an incorporated biotin group, the kit preferably includes an antibiotin antibody. Similarly, the kit may include means for detecting the inherent fluorescence of a compound, means for detecting photoactivatable groups, further labelled antibodies, etc.

Various preferred ligands for use in the methods and other embodiments of the present invention will now be discussed in more detail. In each case, those skilled in the art will appreciate that instead of administering ligands directly, they could be administered in a precursor form, for conversion to the active form by an activating agent present in, or administered to, the same subject.

Sulphonated-benzothiazole-Like Ligands

Suitable ligands for use in this aspect of the present invention are compounds of the formula:

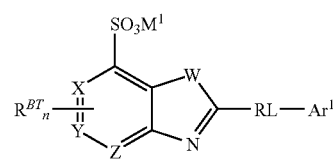

wherein:
W is S, O, or NH;
exactly one of X, Y, and Z is CH or N;
the others of X, Y, and Z are CH;
$M^1$ is an alkali metal cation;

RL is a rigid linker group;
Ar$^1$ is an C$_{5-20}$aryl group;
n is an integer from 0 to 3; and,
each R$^{BT}$ is a core substituent.

In one embodiment, each of X, Y, and Z is CH, and the compounds have the following formula:

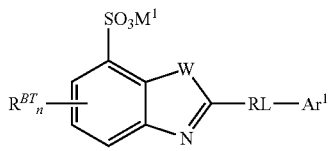

In one embodiment, X is N; Y and Z are each CH; and the compounds have the following formula:

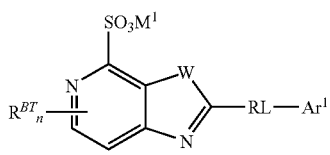

In one embodiment, Y is N; X and Z are each CH; and the compounds have the following formula:

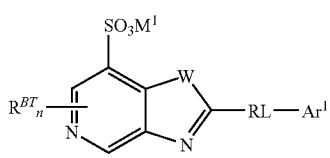

In one embodiment, Z is N; X and Y are each CH; and the compounds have the following formula:

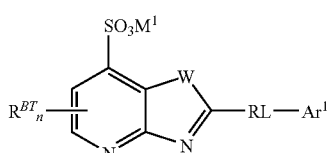

In one embodiment, W is S, and the compounds have the following formula:

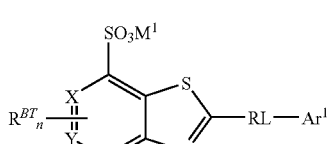

In one embodiment, W is O, and the compounds have the following formula:

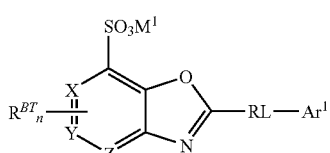

In one embodiment, W is NH, and the compounds have the following formula:

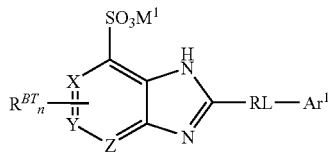

In one embodiment, each of X, Y, and Z is CH; and W is S.
In one embodiment, each of X, Y, and Z is CH; and W is O.
In one embodiment, each of X, Y, and Z is CH; and W is NH.
In one embodiment, X is N; Y and Z are each CH; and W is S.
In one embodiment, X is N; Y and Z are each CH; and W is O.
In one embodiment, X is N; Y and Z are each CH; and W is NH.
In one embodiment, Y is N; X and Z are each CH; and W is S.
In one embodiment, Y is N; X and Z are each CH; and W is O.
In one embodiment, Y is N; X and Z are each CH; and W is NH.
In one embodiment, Z is N; X and Y are each CH; and W is S.
In one embodiment, Z is N; X and Y are each CH; and W is O.
In one embodiment, Z is N; X and Y are each CH; and W is NH.

The bicyclic group, comprising W, X, Y, and Z, may be denoted the "core group." When each of X, Y, and Z is CH, and W is S, the compound may be referred to as a benzothiazole compound, and may be considered to have, as a core group, a benzothiazole group. The "core substituents" may be then be referred to as "benzothiazole substituents."

A preferred ligand for use in this aspect of the present invention is a ligand compound of the formula (I):

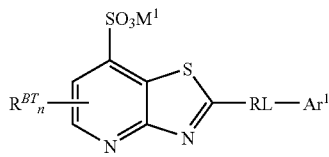

wherein:
M$^1$ is an alkali metal cation;
RL is a rigid linker group;
Ar$^1$ is an C$_{5-20}$aryl group;
n is an integer from 0 to 3; and,
each R$^{BT}$ is a independently benzothiazole substituent.

Both the rigid linker group, RL, and the aryl group, Ar$^1$, are substantially planar. In addition, the rigid linker group, RL, and the aryl group, Ar$^1$, together with the core group (e.g., benzothiazole group), form a compound which is substantially planar. By "substantially planar," it is meant that the moiety/compound has a high degree of planarity e.g. less than 5, 4, 3, 2 or 1° twist between the components, as quantified using standard chemical models and assumptions. Preferably the twist will be no greater than that of the compound of FIG. 16.

In one embodiment, the compound has a compound length which is from about 14.7 AU to about 15.3 AU.

The present inventors have determined that compounds having the characteristics described above may be particularly suitable for the 'Braak staging' methods of the invention. Such compounds may be known in the art, or may be novel as described in more detail below.

The "compound length" is the distance between the two most distant aromatic ring atoms (denoted "reference atoms"). For example, for benzothiazole compounds, at the benzothiazole "end" of the molecule, the reference atom will be one of two atoms:

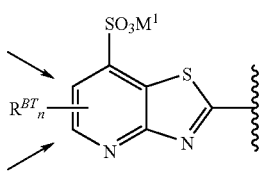

At the aryl "end" of the molecule, when $Ar^1$ is an aryl group having a phenyl core (see below), the reference atom will be one of three atoms:

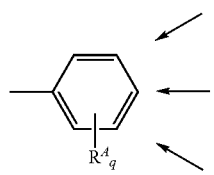

Distances used herein may be computed using 'Chemical Database Service', Daresbury, and the Cambridge Structure Database, using 'Chemical structure search and retrieval software'. This data and software are available in the public domain.

In one embodiment, M is Li, Na, K, or Cs.
In one embodiment, M is Na or K.
In one embodiment, n is 0. In one embodiment, n is 1.
In one embodiment, n is 2. In one embodiment, n is 3.
In one embodiment, each $R^{BT}$ is independently selected from: $C_{1-4}$alkyl, hydroxy, $C_{1-4}$alkoxy, nitro, cyano, halo, and amino.

In one embodiment, each $R^{BT}$ is independently selected from: -Me, -Et, -nPr, -iPr, —OH, —OMe, —OEt, —O(nPr), —O(iPr), —NO$_2$, —CN, —F, —Cl, —Br, —I, —NH$_2$, —NH$_2$, —NHMe, —NHEt, —NH(iPr), —NH(nPr), —NMe$_2$, —NEt$_2$, N(iPr)$_2$, and —N(nPr)$_2$.

In one embodiment, each $R^{BT}$ is independently selected from: $C_{1-4}$alkyl. In one embodiment, each $R^{BT}$ is selected from: -Me, -Et, -nPr, and -iPr. In one embodiment, each $R^{BT}$ is -Me.

In one embodiment, n is 1 and $R^{BT}$ is -Me, -Et, -nPr, or -iPr.
In one embodiment, n is 1 and $R^{BT}$ is -Me.
In one embodiment, the compound has the following formula:

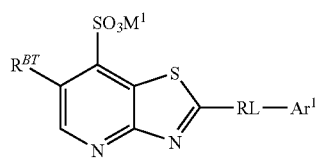

In one embodiment, the compound has the following formula:

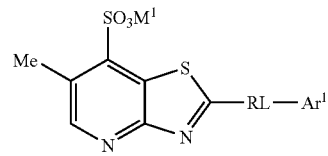

In one embodiment, R is a group of the formula:

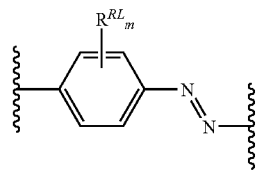

wherein m is an integer from 0 to 4, and each $R^{RL}$ is independently a rigid linker aryl substituent, and the compounds have the formula:

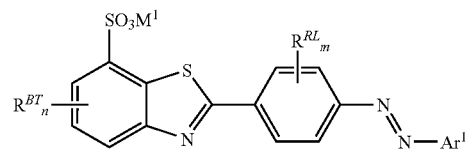

In one embodiment, m is 0. In one embodiment, m is 1.
In one embodiment, m is 2. In one embodiment, m is 3.
In one embodiment, m is 4.

In one embodiment, each $R^{RL}$ is independently selected from: $C_{1-4}$alkyl, hydroxy, $C_{1-4}$alkoxy, nitro, cyano, halo, and amino.

In one embodiment, each $R^{RL}$ is independently selected from: -Me, -Et, -nPr, -iPr, —OH, —OMe, —OEt, —O(nPr), —O(iPr), —NO$_2$, —CN, —F, —Cl, —Br, —I, —NH$_2$, —NH$_2$, —NHMe, —NHEt, —NH(iPr), —NH(nPr), —NMe$_2$, —NEt$_2$, N(iPr)$_2$, and —N(nPr)$_2$.

In one embodiment, each $R^{RL}$ is independently selected from: $C_{1-4}$alkyl.

In one embodiment, RL is a group of the formula:

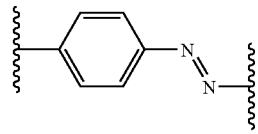

In one embodiment, RL is a group of the formula:

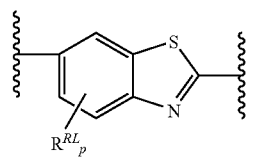

wherein p is an integer from 0 to 3, and each $R^{RL}$ is independently a rigid linker aryl substituent, and the compounds have the formula:

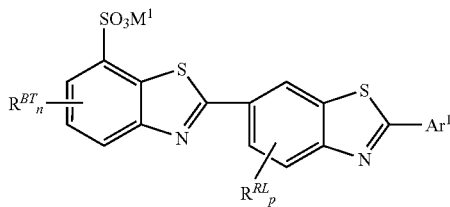

In one embodiment, p is 0. In one embodiment, p is 1.

In one embodiment, p is 2. In one embodiment, p is 3.

In one embodiment, each $R^{RL}$ is independently selected from: $C_{1-4}$alkyl, hydroxy, $C_{1-4}$alkoxy, nitro, cyano, halo, and amino.

In one embodiment, each $R^{RL}$ is independently selected from: -Me, -Et, -nPr, -iPr, —OH, —OMe, —OEt, —O(nPr), —O(iPr), —NO$_2$, —CN, —F, —Cl, —Br, —I, —NH$_2$, —NH$_2$, —NHMe, —NHEt, —NH(iPr), —NH(nPr), —NMe$_2$, —NEt$_2$, N(iPr)$_2$, and —N(nPr)$_2$.

In one embodiment, each $R^{RL}$ is independently selected from: $C_{1-4}$alkyl.

In one embodiment, RL is a group of the formula:

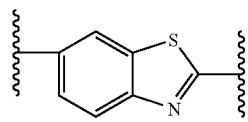

The aryl group, Ar$^1$, is a $C_{5-20}$aryl group. The term "$C_{5-20}$aryl," as used herein, pertains to a monovalent moiety obtained by removing a hydrogen atom from an aromatic ring atom of a $C_{5-20}$aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms. "$C_{5-20}$" denotes ring atoms, whether carbon atoms or heteroatoms.

Examples of $C_{5-20}$aryl groups which do not have ring heteroatoms (i.e., $C_{5-20}$carboaryl groups) include, but are not limited to, those derived from benzene (i.e., phenyl) ($C_6$), naphthalene ($C_{10}$), anthracene ($C_{14}$), phenanthrene ($C_{14}$), naphthacene ($C_{18}$), and pyrene ($C_{16}$).

Examples of $C_{5-20}$heteroaryl groups include, but are not limited to, $C_5$heteroaryl groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, and oxatriazole; and $C_6$heteroaryl groups derived from isoxazine, pyridine (azine), pyridazine (1,2-diazine), pyrimidine (1,3-diazine; e.g., cytosine, thymine, uracil), pyrazine (1,4-diazine), triazine, tetrazole, and oxadiazole (furazan).

Examples of $C_{5-20}$heterocyclic groups (including $C_{5-20}$heteroaryl groups) which comprise fused rings, include, but are not limited to, $C_9$heterocyclic groups derived from benzofuran, isobenzofuran, indole, isoindole, purine (e.g., adenine, guanine), benzimidazole; $C_{10}$heterocyclic groups derived from quinoline, isoquinoline, benzodiazine, pyridopyridine, quinoxaline; $C_{1-3}$heterocyclic groups derived from carbazole; $C_{1-4}$heterocyclic groups derived from acridine, xanthene, phenoxathiin, phenazine, phenoxazine, phenothiazine.

In one embodiment, Ar$^1$ is an aryl group having a phenyl core, and has the formula:

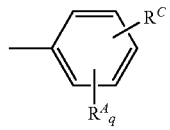

wherein q is an integer from 0 to 5; and each $R^A$ is independently an aryl substituent; $R^C$, is present, is a reactive conjugating substituent, or $R^C$ is, or contains, a detectable label; and the compound has the formula:

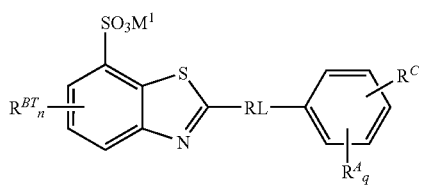

In one embodiment, $R^C$, if present, is a reactive conjugating substituent, and is a group which is suitable for conjugation to another molecule or chemical species.

In one embodiment, $R^C$, if present, is a reactive conjugating substituent, and is, or contains, a reactive functional group suitable for conjugation to another molecule by chemical reaction therewith, to form a covalent linkage therebetween. Examples of suitable reactive functional groups include active esters (e.g., succinimidyl esters).

In one embodiment, $R^C$, if present, is a reactive conjugating substituent, and is, or contains, a moiety suitable for conjugation to another molecule by a strong non-covalent interaction. Examples of such groups include biotin (for binding with molecules bearing avidin or streptavidin).

In one embodiment, $R^C$, if present, is a reactive conjugating substituent, and is, or contains, a moiety suitable for conjugation to another molecule by complex or chelate formation, e.g., a chelating group. Examples of such groups include groups which complex with or chelate, e.g., metal ions, e.g., technetium ions. Examples of such groups include diethylenetriaminepentaacetic acid.

In one embodiment, $R^C$, if present, is, or contains, a detectable label. Examples of detectable labels include, e.g., dyes, fluorescent markers, antigenic groups, stable and unstable isotopes, and positron-emitting carbon atoms. In one embodiment, $R^C$, if present, is, or contains, a detectable label comprising a stable isotope. In one embodiment, $R^C$, if present, is, or contains, a detectable label comprising an unstable isotope. In one embodiment, $R^C$, if present, is, or contains, $^{18}$F. In one embodiment, $R^C$, if present, is, or contains, a detectable label comprising a positron-emitting carbon atom.

Further $R^C$ substituents are discussed below.

In one embodiment, $R^C$ is present, and is as defined above.

In one embodiment, q is 0. In one embodiment, q is 1.

In one embodiment, q is 2. In one embodiment, q is 3.

In one embodiment, q is 4. In one embodiment, q is 5.

In one embodiment, each $R^A$ is independently selected from: —OH, —NH$_2$, —NHR$^1$, —NR$^1$R$^2$, —SO$_3$M$^2$, $C_{1-4}$alkyl, wherein R$^1$ and R$^2$ are each $C_{1-4}$alkyl, and M$^2$ is an alkali metal cation, as defined above.

In one embodiment, at least one $R^A$ is —OH or —NH$_2$.

In one embodiment, Ar¹ is an aryl group having an amino-substituted phenyl core, and has the formula:

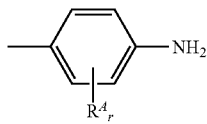

wherein r is an integer from 0 to 4, and each $R^A$ is independently an aryl substituent, as defined above.

In one embodiment, r is 0. In one embodiment, r is 1. In one embodiment, r is 2. In one embodiment, r is 3. In one embodiment, r is 4.

In one embodiment, r is 1 and Ar¹ is a group of the formula:

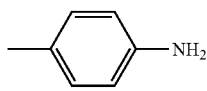

In one embodiment, the compound has the formula:

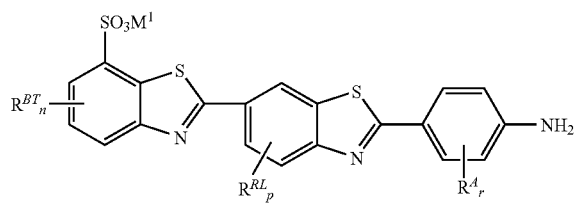

In one embodiment, the compound has the formula:

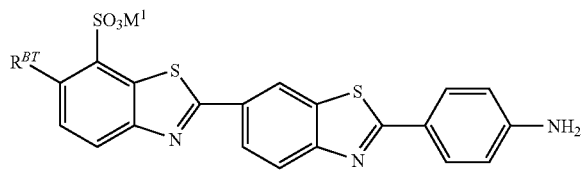

In one embodiment, Ar¹ is an aryl group having a hydroxy-substituted phenyl core, and has the formula:

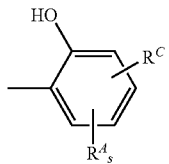

wherein s is an integer from 0 to 4, and each $R^A$ is independently an aryl substituent, as defined above, and $R^C$, is present, is a reactive conjugating substituent, or $R^C$ is, or contains, a detectable label, as defined above.

In one embodiment, s is 0. In one embodiment, s is 1. In one embodiment, s is 2. In one embodiment, s is 3. In one embodiment, s is 4.

In one embodiment, Ar¹ is a group of the formula:

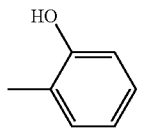

In one embodiment, Ar¹ is a group of the formula:

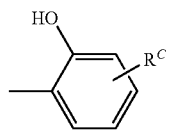

In one embodiment, Ar¹ is a group of the formula:

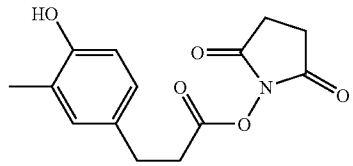

In one embodiment, Ar¹ is an aryl group having a naphthyl core, and has the formula:

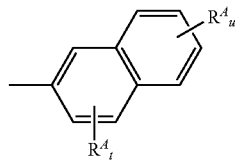

wherein t is an integer from 0 to 3, u is an integer from 0 to 4, and each $R^A$ is independently an aryl substituent, as defined above, and the compound has the formula:

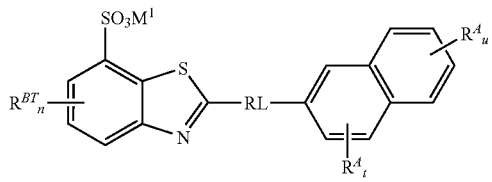

In one embodiment, Ar¹ is an aryl group having a hydroxy-substituted naphthyl core, and has the formula:

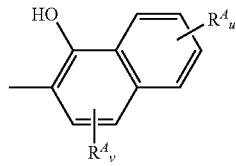

wherein v is an integer from 0 to 2, u is an integer from 0 to 4, and each $R^A$ is independently an aryl substituent.

In one embodiment, Ar¹ has the formula:

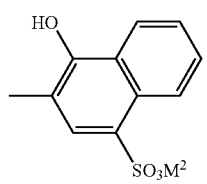

In one embodiment, the compound has the formula:

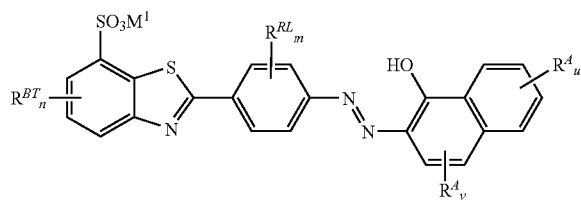

In one embodiment, the compound has the formula:

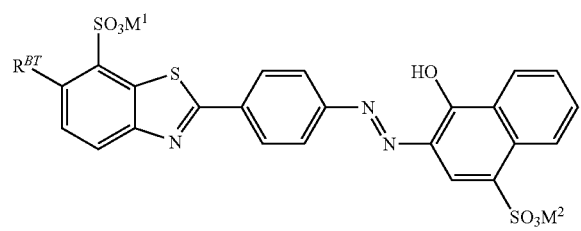

In one embodiment, the ligand is a compound as described below under the heading "Preferred sulphonated-benzothiazole-like ligands."

Compounds of the type described above, e.g. of formula (I), for use in the diagnostic methods of the present invention, may be prepared my conventional means—see e.g. Reference 31.

All such compounds described herein (or derivatives thereof) having the appropriate formula, size, planarity, and activity may be referred to generally, but not limitatively, hereinafter as 'sulphonated benzothiazole-like compounds' or 'SB ligands'). Such compounds will generally be ligands of aggregated tau molecules, e.g. those found in paired helical filaments or neurofibrillary tangles.

The ligands described herein can suitably be detected by incorporating a positron-emitting carbon into one of the methyl groups of the compound as disclosed herein, and detecting the compound by use of positron emission tomography (PET) as is known in the art. Alternatively, or in addition, a technetium-containing chelate can be incorporated into the compound (e.g. as in the $R^C$ group of the compounds described herein), so that selective detection of extracellular tangles could be achieved. A preferred chelating group is $R^C$=diethylenetriaminepentaacetic acid.

The ligands may be conjugated, chelated, or otherwise associated, with other chemical groups, dyes, fluorescent markers, antigenic groups, therapeutic moieties, or any other entity which may aid in a prognostic, diagnostic or therapeutic application. For instance, where the ligand is attached to a dye or fluorescent group, the conjugate can be used as a label of aggregated tau or tau-like molecules. It can thus be used to label intracellular or extracellular tangles characteristic of AD.

Phenothiazines

The present inventors have previously identified another class of compounds, members of which disrupt the structure of PHFs, and reverse the proteolytic stability of the PHF core (WO 96/30766).

Diaminophenothiazine compounds described in WO 96/30766 are shown by the structures of FIG. 8a. Formula (IV) in FIG. 8a represents different resonance form of (II) included for clarity. Compounds (II)-(IV) are all oxidised forms while (I) is a reduced form. Such compounds (which may be referred to hereinafter as 'diaminophenothiazines' or 'phenothiazines') include, e.g. tolonium chloride and methylene blue. Examples are shown in FIG. 8b. All of these are shown in the oxidised form, with all except thionine being in the form stabilised salts (thionine is shown as a neutral oxidised form).

Compounds which may be used in the methods described herein may be any having a formula shown in FIG. 8a, wherein:

each of $R_1$, $R_3$, $R_4$, $R_6$, $R_7$ and $R_9$ is independently hydrogen, halogen, hydroxy, carboxy, substituted or unsubstituted alkyl, haloalkyl or alkoxy;

$R_5$ is hydrogen, hydroxy, carboxy, substituted or unsubstituted alkyl, haloalkyl or alkoxy; and, $R_{10}$ and $R_{11}$ are independently hydrogen, hydroxy, carboxy, substituted or unsubstituted alkyl, haloalkyl or alkoxy;

and pharmaceutically acceptable salts thereof.

In one embodiment:

each of $R_1$, $R_3$, $R_4$, $R_6$, $R_7$ and $R_9$ is independently hydrogen, halogen, hydroxy, carboxy, substituted or unsubstituted $C_{1-6}$alkyl, $C_{1-4}$haloalkyl, or $C_{1-6}$alkoxy;

$R_5$ is independently hydrogen, hydroxy, carboxy, substituted or unsubstituted $C_{1-6}$alkyl, $C_{1-4}$haloalkyl, or $C_{1-6}$alkoxy;

$R_{10}$ and $R_{11}$, are independently selected from hydrogen, hydroxy, carboxy, substituted or unsubstituted $C_{1-6}$alkyl, $C_{1-4}$haloalkyl, or $C_{1-6}$alkoxy.

The term "alkyl" as used in this respect refers to straight or branched chain groups, preferably having one to eight, more preferably one to six, carbon atoms. For example, "alkyl" may refer to methyl, ethyl, n-propyl, isopropyl, butyl, isobutyl, sec-butyl, tert-butyl, pentyl, isopentyl, tert-pentyl, hexyl, isohexyl, and the like. Suitable substituents for the substituted alkyl groups used in the invention include the mercapto, thioether, nitro, amino, aryloxy, halogen, hydroxyl, and carbonyl groups as well as aryl, cycloalkyl and non-aryl heterocyclic groups.

The terms "alkoxy" refers to groups as defined herein above as alkyl groups, as the case may be, which also carry an oxygen atom interposed between them and the substrate residue to which they are attached.

The term "haloalkyl" represents a straight or branched alkyl chain having from one to four carbon atoms with 1, 2 or 3 halogen atoms attached to it. Typical haloalkyl groups include chloromethyl, 2-bromethyl, 1-chloroisopropyl, 3-fluoropropyl, 2,3-dibrombutyl, 3-chloroisobutyl, iodo-t-butyl, trifluoromethyl and the like.

The "halogen" represents fluoro, chloro, bromo or iodo.

Some of these phenothiazines possess one or more asymmetrically substituted carbon atoms and therefore exist in racemic and optically active forms. The invention is intended to encompass the racemic forms of the compounds as well as any of the optically active forms thereof.

Acid addition salts may be formed between basic compounds of FIG. 8a or 8b and inorganic acids, e.g. hydrohalic acids such as hydrochloric acid and hydrobromic acid, sulphuric acid, nitric acid, phosphoric acid etc., or organic acid, e.g. acetic acid, citric acid, maleic acid, fumaric acid, tartaric acid, methanesulphonic acid, p-toluenesulphonic acid etc.

In a particular preferred embodiment the present invention employs a phenothiazine wherein:

$R_1$, $R_3$, $R_4$, $R_6$, $R_7$ and $R_9$ are independently —H, —CH$_3$, —C$_2$H$_5$, or —C$_3$H$_7$;

$R_{10}$ and $R_{11}$ are independently —H, —$CH_3$, —$C_2H_5$ or —$C_3H_7$;

$R_5$ is —H, —$CH_3$, —$C_2H_5$, or —$C_3H_7$;

or a pharmaceutically acceptable salt thereof.

The present inventors now teach herein that such phenothiazine compounds of this sort can bind to the PHFs at a specific site which appears, on the basis of its binding characteristics, to be distinct from that at which the sulphonated benzothiazole-like compounds, described above, can bind. The binding of the phenothiazine compounds to this site is thought to effect the inhibition of tau aggregation.

Phenothiazine compounds may be used in the methods and other embodiments described above, incorporating labels as appropriate. When suitably labeled with a positron-emitting functional group (detectable by PET—see FIGS. 11, 11b, 12, 13) such compounds would serve as ligands for all tau aggregates, and would be capable of crossing the blood-brain-barrier (Ref 36) and entering cells.

In a further embodiment, in the light of the disclosure herein, it will be appreciated that the effect of, and particularly the progress of, therapy based on tau-tau binding inhibitors may be monitorable by use of SB ligands.

Blocking Ligands

Preferably these are benzthiazoles of the formula:

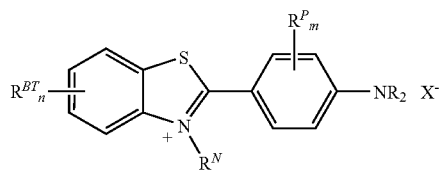

wherein:

n is an integer from 0 to 4;

each $R^{BT}$ is independently a blocking ligand benzothiazole substituent;

m is an integer from 0 to 4;

each $R^P$ is independently a phenylene substituent;

each R is independently —H or an amino substituent; and, either:

$R^N$ and $X^-$ are both absent and the associated (tertiary) nitrogen atom is neutral;

or:

$R^N$ is a benzothiazolino substituent and the associated (quaternary) nitrogen atom bears a positive charge, and $X^-$ is a counter ion.

Preferred benzthiazoles include thioflavin T. As shown in the Examples below, such compounds (e.g. 1b or 2 in FIG. 5) are displaced from NFTs by SB-ligands (e.g. 1a in FIG. 5). However such compounds do bind preferentially to amyloid.

In one embodiment, n is 0. In one embodiment, n is 1.

In one embodiment, n is 2. In one embodiment, n is 3.

In one embodiment, n is 4. In one embodiment, n is 0, 1, or 2.

Examples of blocking ligand benzothiazole substituents, $R^{BT}$, include, but are not limited to, $C_{1-4}$alkyl groups, —$SO_3H$, and —$SO_3M^3$, wherein $M^3$ is a cation. In one embodiment, $M^3$ is an alkali metal cation. In one embodiment, $M^3$ is Li, Na, K, or Cs. In one embodiment, $M^3$ is Na or K. Examples of $C_{1-4}$alkyl groups include, but are not limited to, -Me, -Et, -nPr, and -iPr.

In one embodiment, each $R^{BT}$ is independently a $C_{1-4}$alkyl group.

In one embodiment, each $R^{BT}$ is selected from: -Me, -Et, -nPr, and -iPr. In one embodiment, each $R^{BT}$ is -Me. In one embodiment, n is 1 and $R^{BT}$ is -Me, -Et, -nPr, or -iPr. In one embodiment, n is 1 and $R^{BT}$ is -Me.

In one embodiment, one of the $R^{BT}$ groups is —$SO_3H$ or —$SO_3M^3$. In one embodiment, one of the $R^{BT}$ groups is —$SO_3H$ or —$SO_3M^3$, and another of the $R^{BT}$ groups is a $C_{1-4}$alkyl group. In one embodiment, n is 2 and one $R^{BT}$ is a $C_{1-4}$alkyl group and one $R^{BT}$ is —$SO_3H$ or —$SO_3M^3$. In one embodiment, n is 2 and one $R^{BT}$ is -Me and one $R^{BT}$ is —$SO_3H$ or —$SO_3M^3$.

In one embodiment, $R^N$ and $X^-$ are both absent and the associated (tertiary) nitrogen atom is neutral.

In one embodiment, $R^N$ is a benzothiazolino substituent and the associated (quaternary) nitrogen atom bears a positive charge, and $X^-$ is a counter ion. Examples of benzothiazolino substituents, $R^N$, include, but are not limited to, $C_{1-4}$alkyl groups. In one embodiment, $R^N$ is -Me, -Et, -nPr, or -iPr. In one embodiment, $R^N$ is -Me. Examples of counter ions include, but are not limited to, $Cl^-$, $Br^-$, and $I^-$. In one embodiment, $R^N$ is -Me and $X^-$ is $Cl^-$.

In one embodiment, m is 0. In one embodiment, m is 1.

In one embodiment, m is 2. In one embodiment, m is 3.

In one embodiment, m is 4.

Examples of phenylene substituents, $R^P$, include, but are not limited to, $C_{1-4}$alkyl groups.

In one embodiment, each R is —H, and the amino group is —$NH_2$. In one embodiment, one R is —H and one R is an amino substituent. In one embodiment, each R is an amino substituent. Examples of amino substituents include, but are not limited to, $C_{1-4}$alkyl groups. In one embodiment, the amino group is —$NH_2$, —NHMe, —NHEt, —NH(iPr), —NH(nPr), —$NMe_2$, —$NEt_2$, $N(iPr)_2$, or —$N(nPr)_2$.

Preferred embodiments of blocking ligands are shown in FIG. 5 as compounds 1b and 2.

Preferred Sulphonated-benzothiazole-Like Ligands

In one aspect of the present invention, the ligands used to label the aggregated tau, preferable extracellular aggregated tau present in NFTs, are compounds having the formula (II):

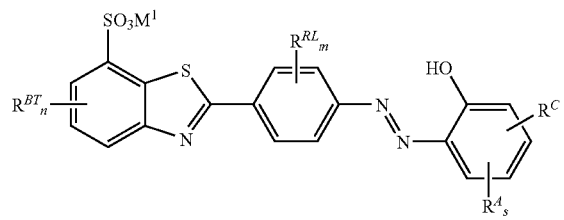

wherein:

$M^1$ is an alkali metal cation;

n is an integer from 0 to 3;

each $R^{BT}$ is a independently benzothiazole substituent;

m is an integer from 0 to 4;

each $R^{RL}$ is independently a rigid linker aryl substituent;

s is an integer from 0 to 4;

each $R^A$ is independently an aryl substituent; and, $R^C$, if present, is a reactive conjugating substituent, or $R^C$ is, or contains, a detectable label.

In various embodiments, $M^1$, n, each $R^{BT}$, each $R^{RL}$, s, each $R^A$, and $R^C$ are as described herein (e.g., under the heading "Sulphonated-benzothiazole-like ligands," above).

The rigid linker group, RL, and the aryl group, $Ar^1$, together with the benzothiazole group, form a compound which is substantially planar, that is, has a high degree of planarity.

As shown herein, such compounds may be particularly effective when it is desired to incorporate a bulky $R^C$ group in order to facilitate detection.

In one embodiment, the compound has the formula:

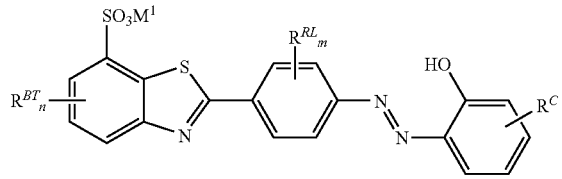

In one embodiment, the compound has the formula:

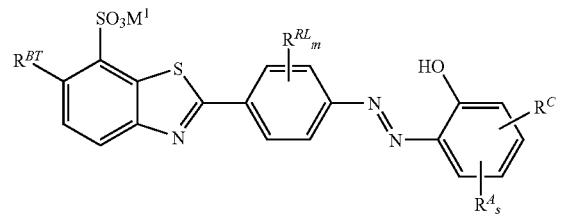

In one embodiment, the compound has the formula:

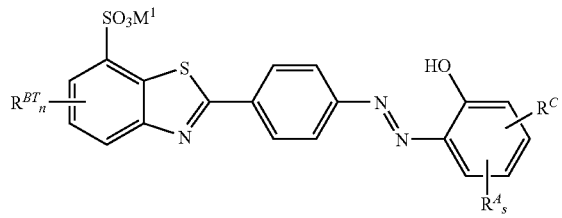

In one embodiment, the compound has the formula:

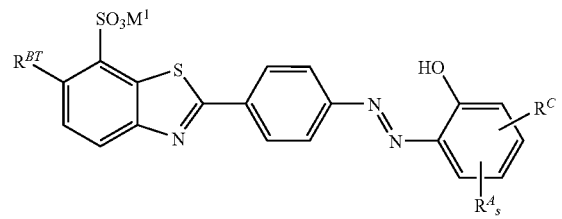

In various embodiments, s may be as discussed above.

In one embodiment, each $R^A$ is independently selected from the substituents given above in relation to formula (I).

In one embodiment, the compound has the formula:

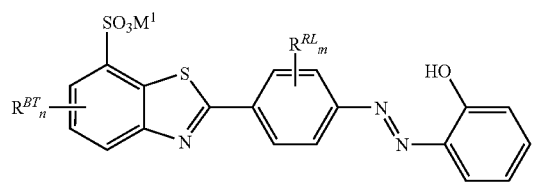

In one embodiment, the compound has the formula:

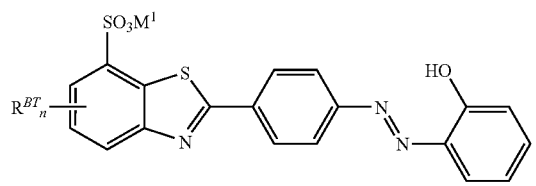

In one embodiment, the compound has the formula:

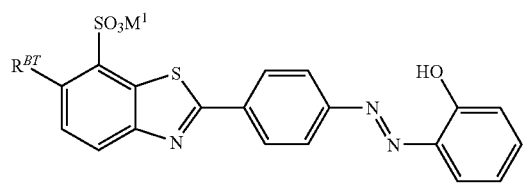

In one embodiment, the compound has the formula:

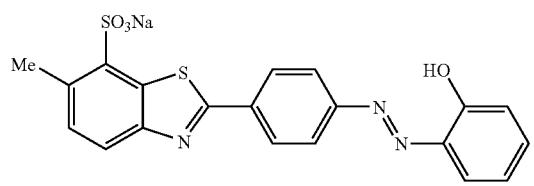

In one embodiment, the compound has the formula:

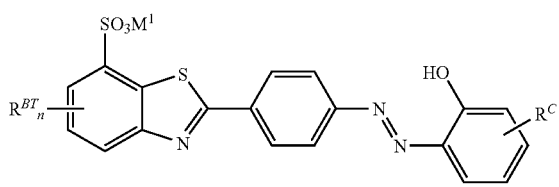

In one embodiment, the compound has the formula:

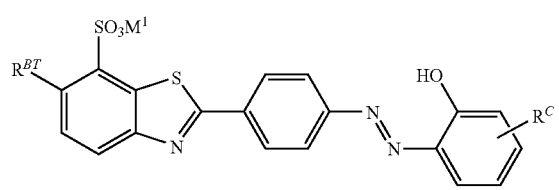

In one embodiment, the compound has the formula:

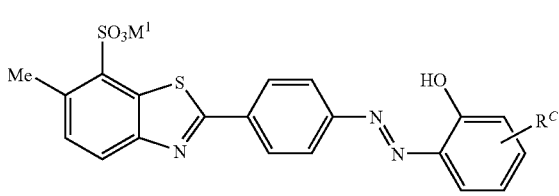

Various $R^C$ substituents are discussed elsewhere herein.
In one embodiment, the compound has the formula:

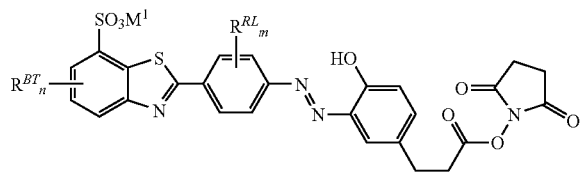

In one embodiment, the compound has the formula:

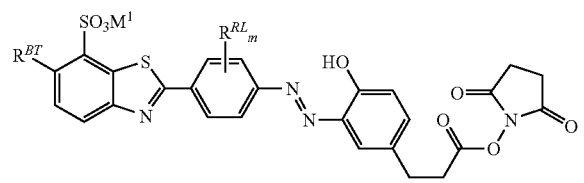

In one embodiment, the compound has the formula:

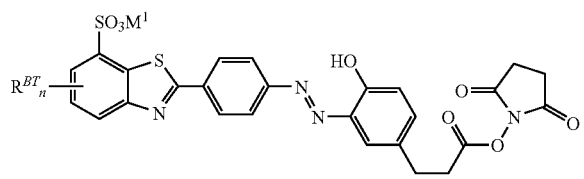

In one embodiment, the compound has the formula:

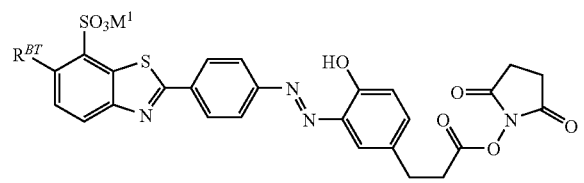

In one embodiment, the compound has the formula:

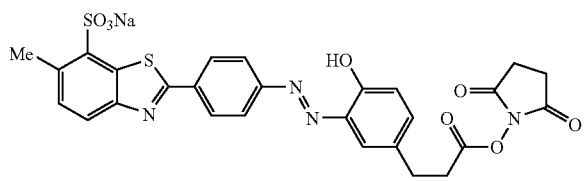

Some of these preferred compounds are shown in FIGS. 4a-c, and derivatives thereof.

Thus, according to one aspect, the present invention provides a compound represented by the formula shown in FIG. 4a, or a derivative thereof e.g. wherein $R^C$ is a conjugating group as described above. As shown in the Examples hereinafter, such derivatives (e.g. compound 4b) retain the appropriate binding activity.

The novel compounds disclosed (e.g. of formula (II)) herein are useful inter alia as synthetic ligands of neurofibrillary tangles, such as those characteristic of AD. The discovery of the minimum critical structure required for binding to these tangles thus provides for the possibility of designing high-affinity ligands which can be used to target the tangles, and can thus be used in the diagnosis, prognosis or treatment of diseases such as AD.

Such compounds will be referred to below as preferred SB ligands.

Mimetics of Preferred SB Ligands

In general, there are several steps commonly taken in the design of a mimetic from a compound having a given target property (in this case a preferred SB tau-tau aggregation ligand) of which the most important is that the particular parts of the compound that are critical and/or important in determining the target property are determined. The provision by the present inventors of the minimum critical structure required for high affinity binding to aggregated tau molecules has obviated this step.

The minimum critical structure of compound 4a can be modeled according to its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of the ligand, rather than the bonding between atoms) and other techniques can be used in this modeling process.

In a variant of this approach, the three-dimensional structure of the preferred SB ligand and its binding partner are modeled. This can be especially useful where the ligand and/or binding partner change conformation on binding, allowing the model to take account of this in the design of the mimetic. A template molecule is then selected onto which chemical groups which mimic the minimum critical structure can be grafted. The template molecule and the chemical groups grafted on to it can conveniently be selected so that the mimetic is easy to synthesise, is likely to be pharmacologically acceptable, and does not degrade in vivo, while retaining the required biological activity. The mimetic or mimetics found by this approach can then be screened to see whether they have the target property, or to what extent they exhibit it. Further optimisation or modification can then be carried out to arrive at one or more final mimetics for further testing or optimisation, e.g. in vivo or clinical testing. Optimisation may include selecting a mimetic compound as described above, and contacting it with a preparation of aggregated tau molecules (e.g. preaggregated tau in solution, or bound to a solid phase, or isolated from PHFs—see WO96/30766 and assays described below) and determining the extent to which the test substance(s) binds to the aggregated tau molecules and\or displaces compound 4a from the molecules.

Methods of Labelling Aggregated Tau

In one aspect, the present invention thus provides a method of labelling aggregated tau or tau-like molecules, comprising contacting the aggregated tau molecules with a preferred SB-ligand compound or derivative thereof as provided herein (e.g. of formula (II)) and detecting the presence of said compound or derivative. Methods of use may be performed e.g. by analogy to the use of the ligands given in Refs 26-34.

Where used herein, the term "tau protein" refers generally to any protein of the tau protein family. Tau proteins are characterised as being one among a larger number of protein families which co-purify with microtubules during repeated cycles of assembly and disassembly (Shelanski et al. (1973) Proc. Natl. Acad. Sci. USA, 70., 765-768), and are known as microtubule-associated-proteins (MAPs). Members of the tau family share the common features of having a characteristic N-terminal segment, sequences of approximately 50 amino acids inserted in the N-terminal segment, which are developmentally regulated in the brain, a characteristic tandem repeat region consisting of 3 or 4 tandem repeats of 31-32 amino acids, and a C-terminal tail.

"Tau like" molecules include, for instance, MAP2, which is the predominant microtubule-associated protein in the somatodendritic compartment (Matus, A., in "Microtubules" [Hyams and Lloyd, eds.] pp 155-166, John Wiley and Sons, NY). MAP2 isoforms are almost identical to tau protein in the tandem repeat region, but differ substantially both in the sequence and extent of the N-terminal domain (Kindler and Garner (1994) Mol. Brain. Res. 26, 218-224). Nevertheless, aggregation in the tandem-repeat region is not selective for the tau repeat domain. Thus it will be appreciated that any discussion herein in relation to tau protein or tau-tau aggregation should be taken as relating also to tau-MAP2 aggregation, MAP2-MAP2 aggregation and so on.

The preferred SB ligand may be conjugated, chelated, or otherwise associated with, a further group or entity which has a diagnostic, prognostic or therapeutic purpose or effect, e.g. to a fluorescent group which thus enables visualisation of neurofibrillary tangles to which the ligand binds.

Diagnostic Compositions and Uses

Generally, a preferred SB ligand according to the present invention (e.g. of formula (II)) may be provided in an isolated and/or purified form, i.e. substantially pure. This may include being in a composition where it represents at least about 90% active ingredient, more preferably at least about 95%, more preferably at least about 98%. Such a composition may, however, include inert carrier materials or other pharmaceutically- and physiologically-acceptable excipients. A composition according to the present invention may include in addition to a preferred SB ligand as disclosed herein, one or more other molecules of diagnostic, prognostic or therapeutic use.

A preferred SB ligand substance according to the present invention, or a composition comprising such a ligand, may be provided for use in a method of diagnosis, prognosis or treatment of the human or animal body by therapy, especially in relation to a condition such as AD as described below.

In a further aspect, the present invention provides a method of diagnosis or prognosis, the method comprising administering to the mammal a diagnostically- or prognostically-effective amount of one or more preferred SB ligands as described herein. This aspect embraces such compounds for use in a method of diagnosis or prognosis. Both in vitro and in vivo uses are encompassed by this aspect. In vitro methods may be performed by (i) obtaining a sample of appropriate tissue from a subject; (ii) contacting the sample with the preferred SB ligand; (iii) detecting the amount and\or localisation of the preferred SB ligand bound to the sample (iv) correlating the result of (v) with the stage or severity of the disease in the subject.

In a further aspect, the present invention provides the use of a preferred SB ligand or derivative as provided herein, in the manufacture of a composition for the diagnosis, prognosis or therapy of a disease as described above.

The disease or condition may be e.g. AD, or an AD-like condition, or any other condition in which aggregated protein molecules are implicated.

Notably it is not only Alzheimer's Disease in which tau protein (and aberrant function or processing thereof) may play a role. The pathogenesis of neurodegenerative disorders such as Pick's disease and Progressive Supranuclear Palsy (PSP) appears to correlate with an accumulation of pathological truncated tau aggregates in the dentate gyrus and stellate pyramidal cells of the neocortex, respectively. Other dementias include fronto-temporal dementia (FTD); parkinsonism linked to chromosome 17 (FTDP-17); disinhibition-dementia-parkinsonism-amyotrophy complex (DDPAC); pallido-ponto-nigral degeneration (PPND); Guam-ALS syndrome; pallido-nigro-luysian degeneration (PNLD); cortico-basal degeneration (CBD) and others (see Wischik et al. 2000, loc. cit, for detailed discussion—especially Table 5.1). All of these diseases, which are characterized primarily or partially by abnormal tau aggregation, are referred to herein as "tauopathies".

Diagnostic compositions may comprise, in addition to one of the above SB-ligand derivatives, a diagnosticly acceptable excipient, carrier, buffer, stabiliser, or other materials well known to those skilled in the art. Such materials should be non-toxic and should not interfere with the binding activity of the substance to aggregated tau, or the efficacy of any bioactive group linked to or otherwise associated with the substance. The precise nature of the carrier or other material may depend on the route of administration, e.g. oral, intravenous, cutaneous or subcutaneous, nasal, intramuscular, intraperitoneal routes.

Diagnostic compositions for oral administration may be in tablet, capsule, powder or liquid form. A tablet may include a solid carrier such as gelatin or an adjuvant. Liquid diagnostic compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the ligand will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A composition as described above may be administered alone or in combination with other treatments, either simultaneously or sequentially, depending on the condition to be treated.

Identification of Ligands

A further method for identifying ligands for aggregated tau requires a screening assay which can be used in a format which permits high through-put screening of chemical libraries to identify compounds with the required activity. Until now, no such method has been readily available. Preferred methods would not require pre-labelled compounds, since the labelling process may severely limit chemical search capacity.

In a further aspect of the present invention a method is provided which can be used as a high through-put screening assay, which is not limited by the need to have pre-labelled test substances. In preferred embodiments the method employs the following steps:

1. the high capacity generation of tau proteins in a form which have undergone partial aggregation in the course of preparation;
2. using tau proteins prepared in this manner for testing putative ligands in the tau-tau binding assay provided in WO96/30766 to identify substances which have minimal or entirely absent activity as tau-aggregation inhibitors or enhance tau-tau binding at high concentrations;

3. testing putative ligands in the presence of an exemplary potent tau-aggregation inhibitor, such as DMMB, at an inhibitory concentration;
4. putative ligands can be identified by the property that they lack capacity to block tau-tau binding through the repeat domain, but block the inhibitory activity of a potent tau-aggregation inhibitor.

Thus the invention provides an in vitro method for identifying a ligand capable of labeling aggregated PHF tau protein, the method comprising the steps of:
(i) providing a first agent suspected of being capable of labeling aggregated PHF tau protein,
(ii) contacting (a) a tau protein or a derivative thereof containing the tau core fragment bound to a solid phase so as to expose a high affinity tau capture site (e.g. a truncated tau protein corresponding to the core fragment and terminating at Ala390-dGA), with (b) a liquid phase tau protein or derivative thereof capable of binding to the solid phase tau protein or derivative (e.g. dGAE which terminates at Glu-391), and (c) said selected first agent and (d) a second agent known to be tau-tau binding inhibitor,
(iii) selecting a first agent which fully or partially relieves the inhibition of binding of the liquid phase tau protein or derivative of (b) to the solid phase tau protein or derivative of (a) by the inhibitor (d).

Agents satisfying (iii) may be provided as ligands.

Preferably the method is carried out in conjunction with (before, during, after) the following steps:
(ibis) contacting (a) a tau protein or a derivative thereof containing the tau core fragment bound to a solid phase so as to expose a high affinity tau capture site, (b) a liquid phase tau protein or derivative thereof capable of binding to the solid phase tau protein or derivative, with (c) said first agent and,
(ibis.1) detecting inhibition of tau-tau binding as exhibited by inhibition of binding of the liquid phase tau protein or derivative of (b) to the solid phase tau protein or derivative of (a),
(ibis.2) selecting a first agent which has minimal or absent activity as tau-tau binding inhibitors and\or optionally enhance tau-tau binding.

Agents satisfying (iii) and (ibis.2) may be provided as ligands.

The inhibitor is preferably a diaminophenathiozine as described above (most preferably DMMB). The compounds selected for screening may be any compound, including SB-ligands.

In preferred forms the liquid phase tau protein or derivative is prepared in a form which has undergone partial aggregation prior to exposure to the solid phase. Apart from that, the assay may be carried out broadly as described in WO96/30766 and summarised in more detail in the Examples below. Preferably alkaline or physiological conditions (e.g. PBS) are used for the binding steps, and results are detected immunologically.

These and other aspects of the present invention will become more apparent on reading the ensuing non-limiting Examples, in which embodiments of the invention will be described by way of example only. Reference is made to the accompanying figures, in which:

(d) shows levels of SDS-insoluble beta-amyloid protein isolated from control cases and cases with Alzheimer's disease, as reported in Harrington et al., (Am J Pathol 1994; 145: 1472-1484). Although the mean level is higher in AD than in controls, 70% of AD cases overlap with levels of beta-amyloid found in control subjects.

Figure 1A:
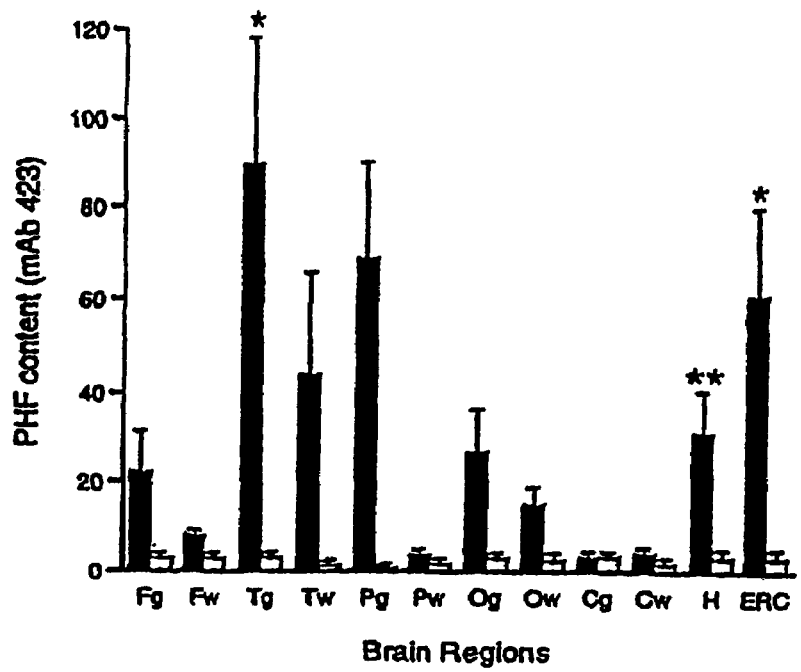
FIG. 1 shows the regional distribution of PHF-tau, measured using antibodies mAb423 (A) or mAb7.51 after formic acid treatment of the PHF fraction (B), for 18 cases of AD. Taken from Mukaetova-Ladinska et al., (1993), Am. J. Pathol. 143, 565-578.
Figure 1B:
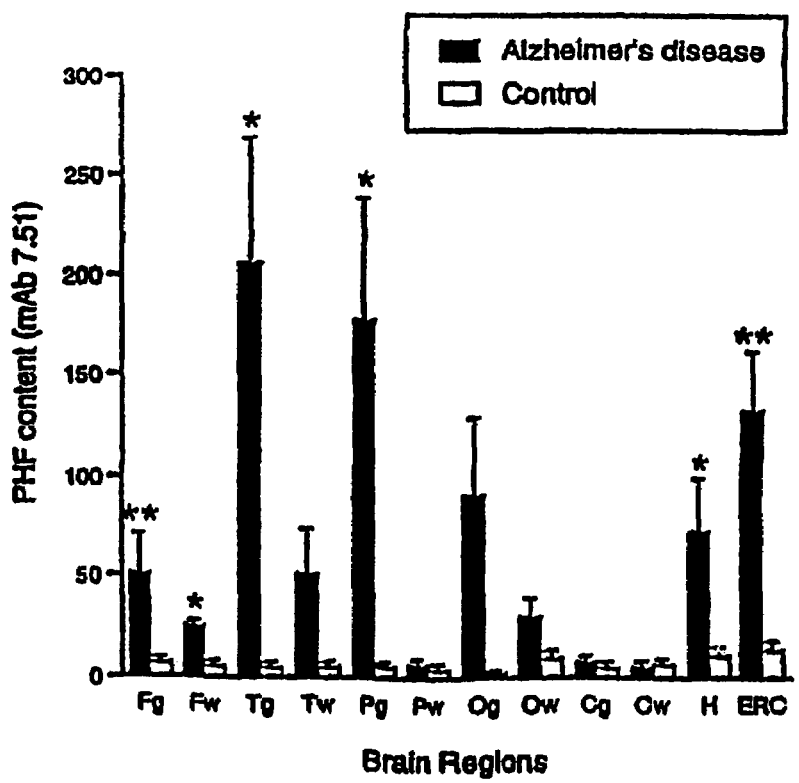
Figure 2A:
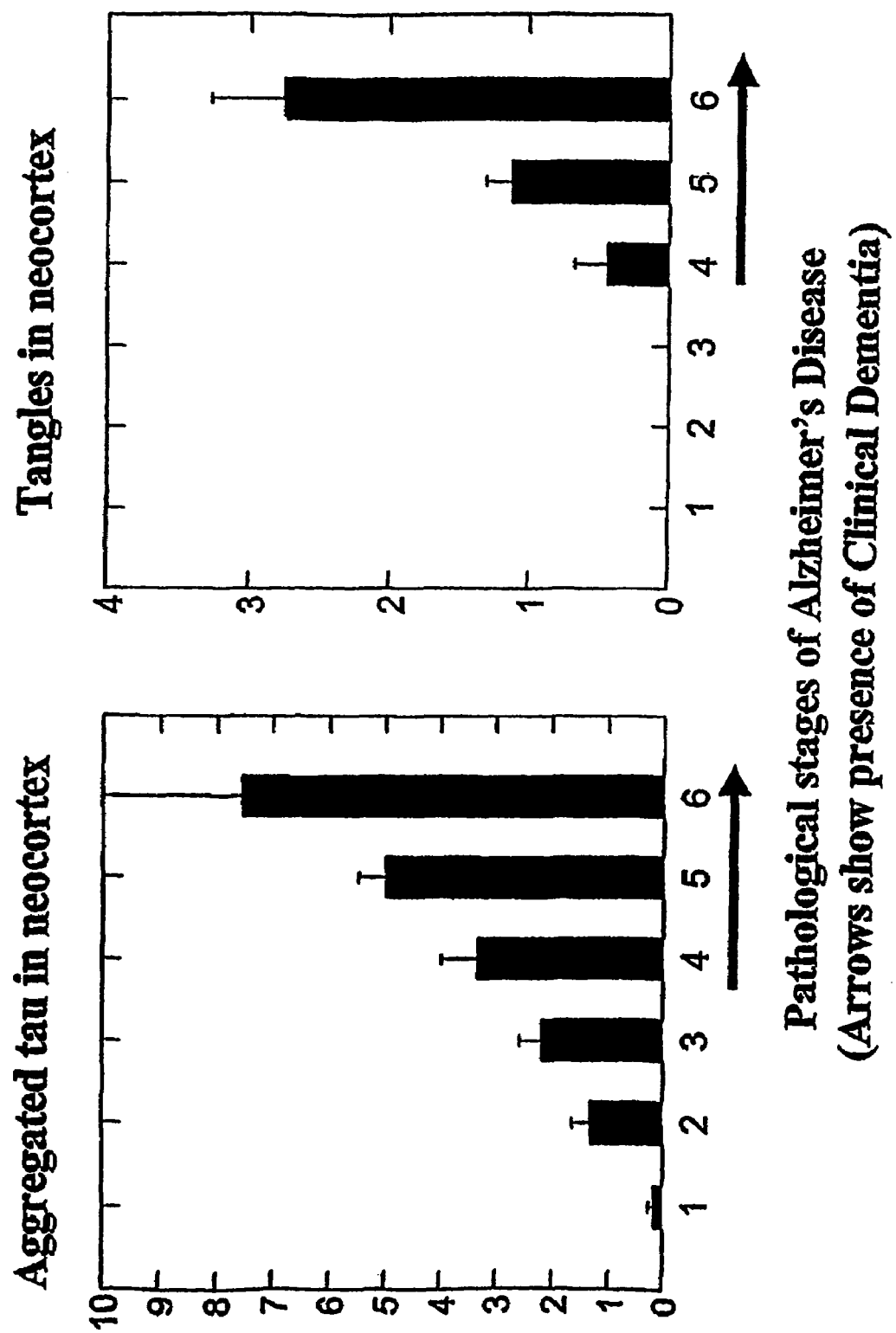
FIG. 2(a) shows the aggregation of tau molecules and the appearance of neurofibrillary tangles during the pathological stages of AD. Taken from (Mukaetova-Ladinska, E. B. et al. (2000) Am. J. Pathol. Vol. 157, No. 2, 623-636); (b) shows the neuropathological staging proposed by Braak; (c) shows that the appearance of clinical dementia by DSM-IV criteria appears to correspond statistically to the transition between stages III and IV.
Figure 2B:
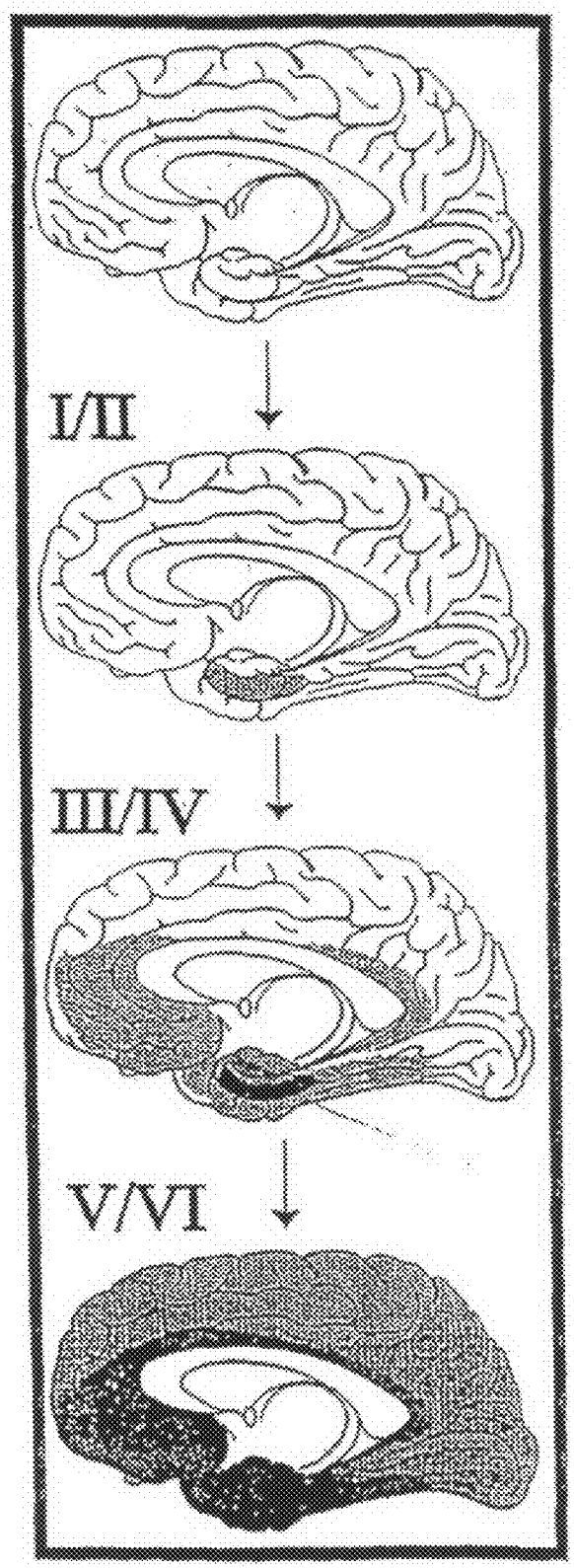
Figure 2C:
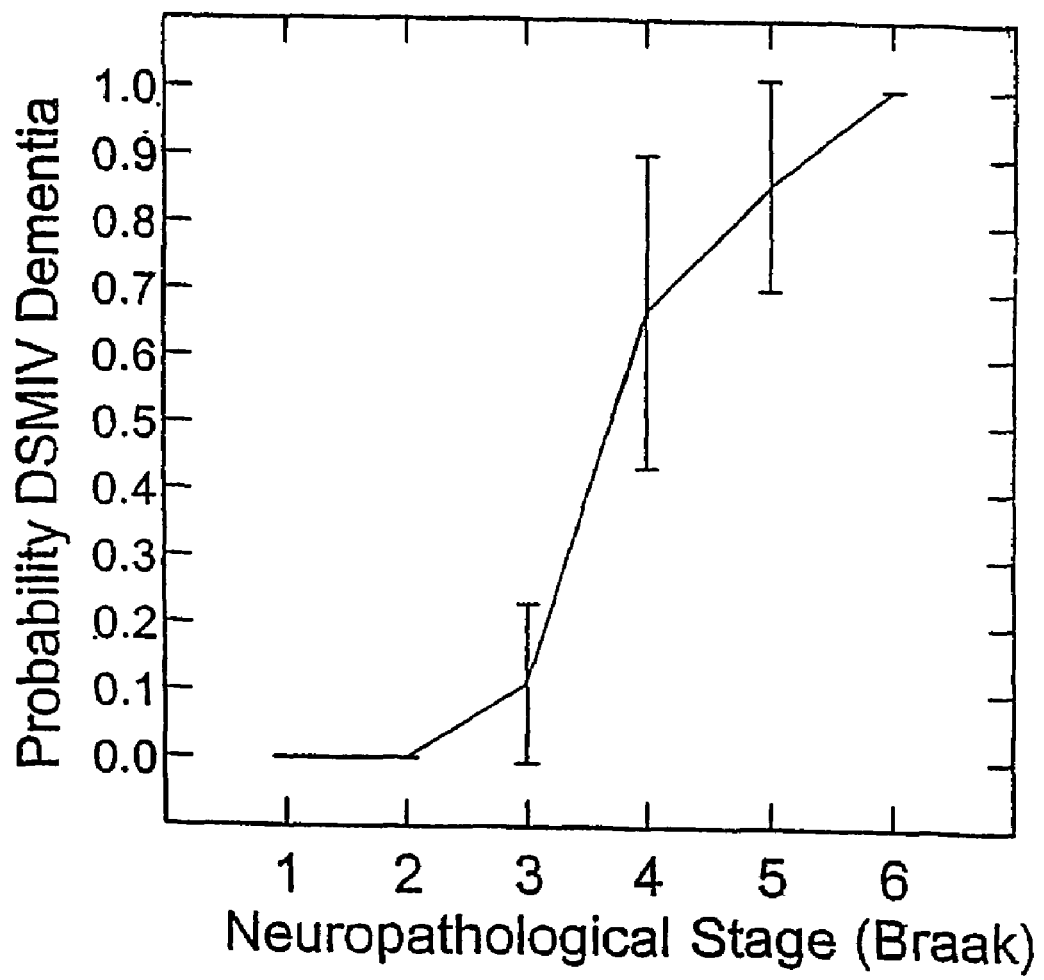
Figure 2D:
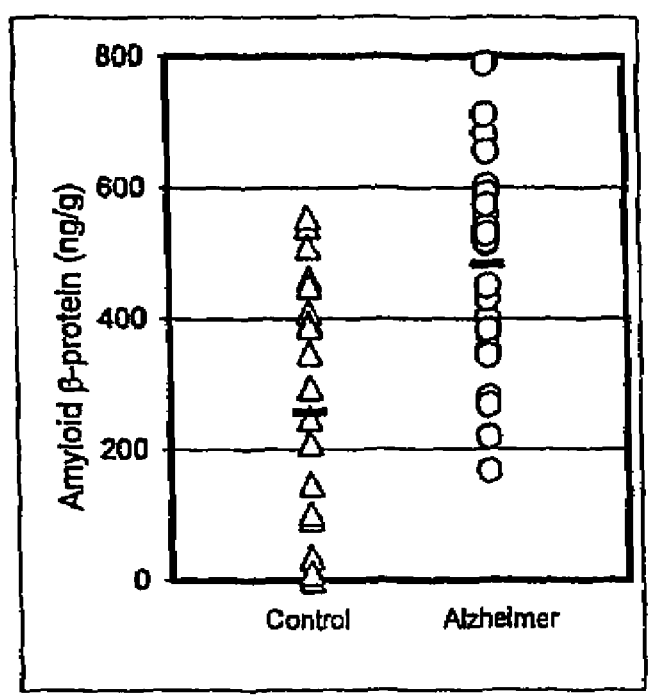
Figure 3:
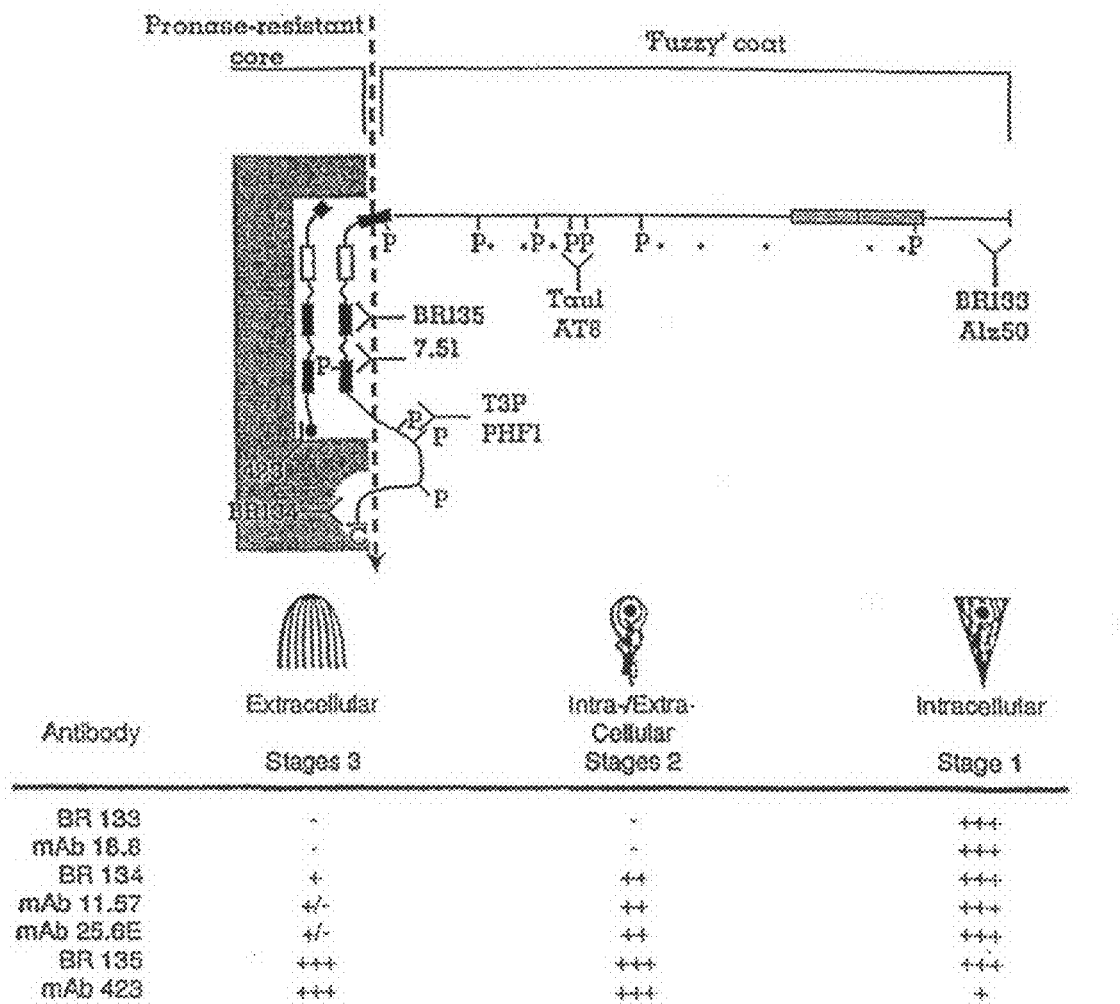

FIG. 3 shows a schematic representation of a neurofibrillary tangle (top), and the immunoreactivity changes that are observed during disease progression (bottom). Taken from Bondareff et al. (1994) J. Neuropathol. Exp. Neurol. 53, 2, 158-164.

Figure 4:
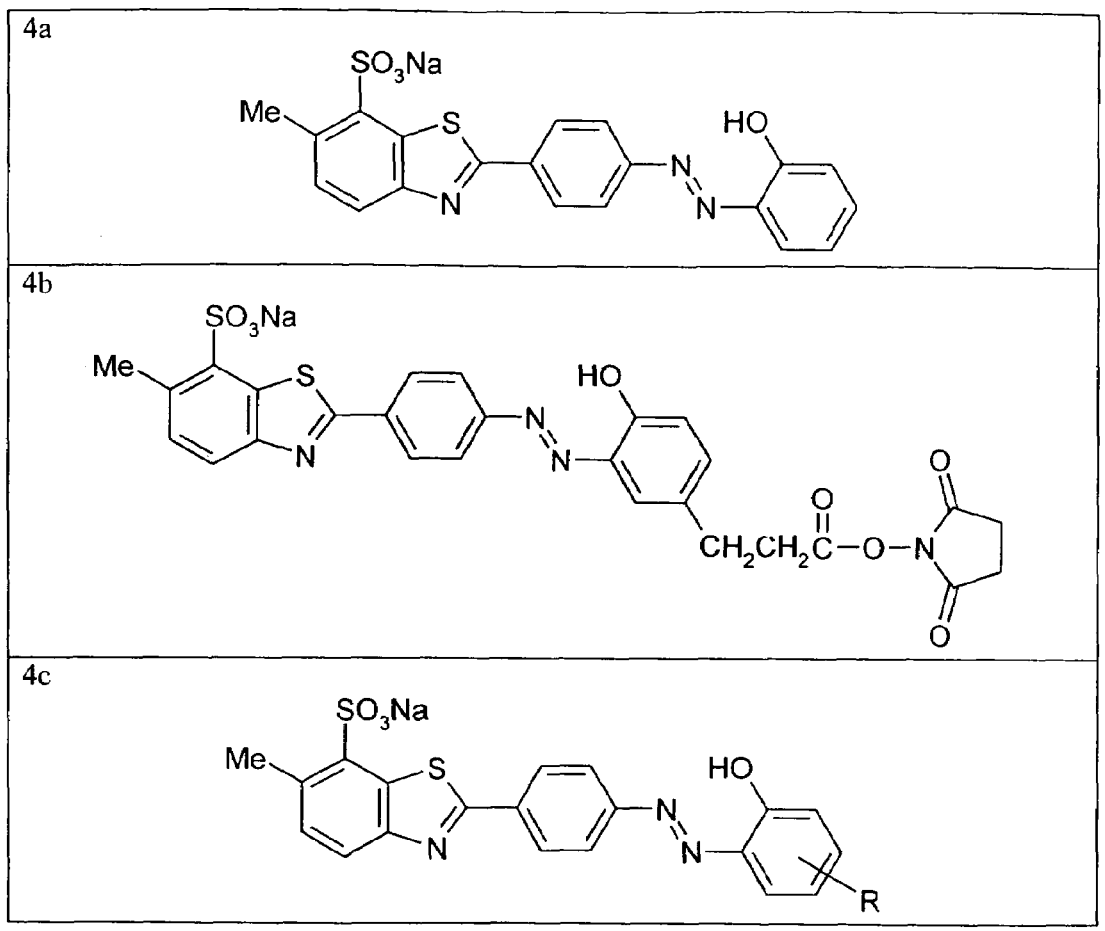

FIG. 4 shows the chemical structures of: the minimum critical structure which enables high affinity binding to aggregated tau molecules (compound 4a); a biotinylated version of compound 4a (compound 4b); and an R-substituted derivative of compound 4a (compound 4c), wherein R is any suitable substituent.

Figure 5:
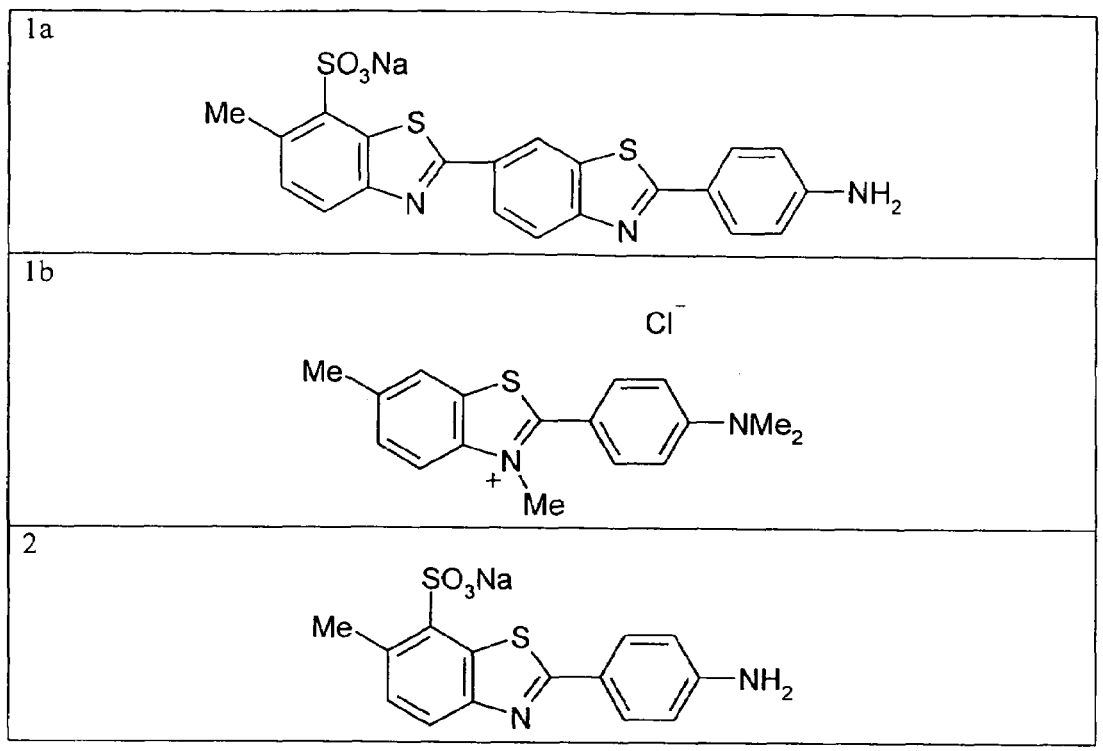
Figure 5:
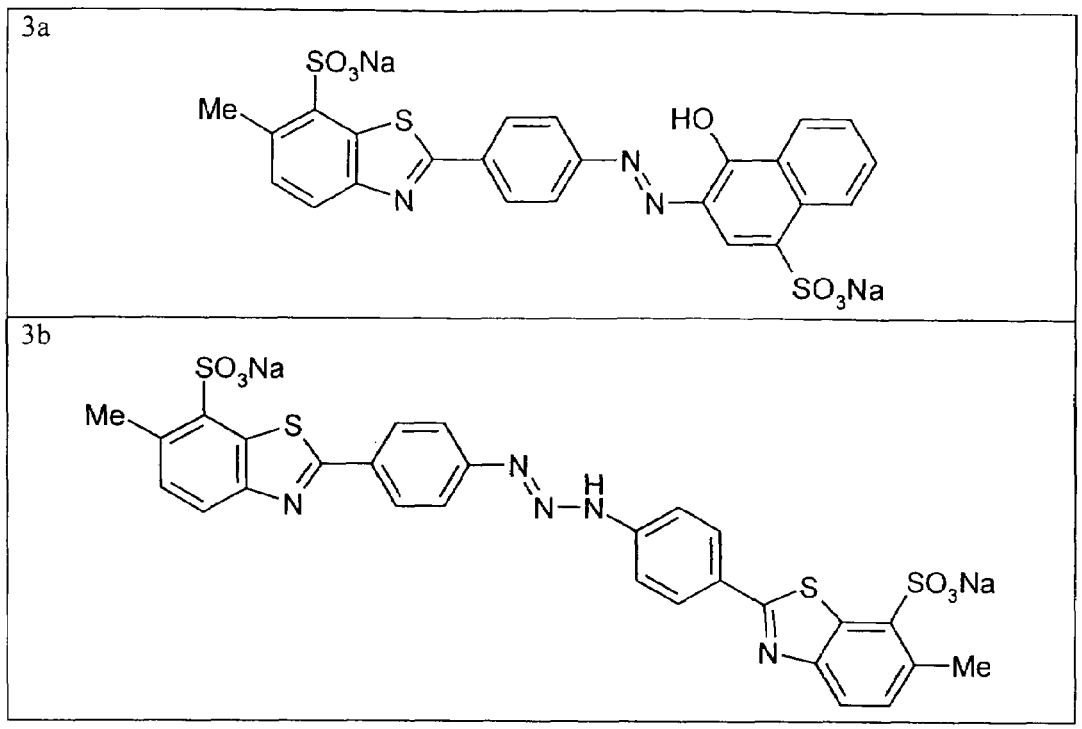

FIG. 5 shows the chemical structures of: primulin (compound 1a); thioflavin-T (compound 1b); 2-(4-amino phenyl)-6-methyl-7-sulphonate benzothiazole (compound 2); thiazin red (compound 3a); and thiazin yellow (compound 3b).

Figure 6:
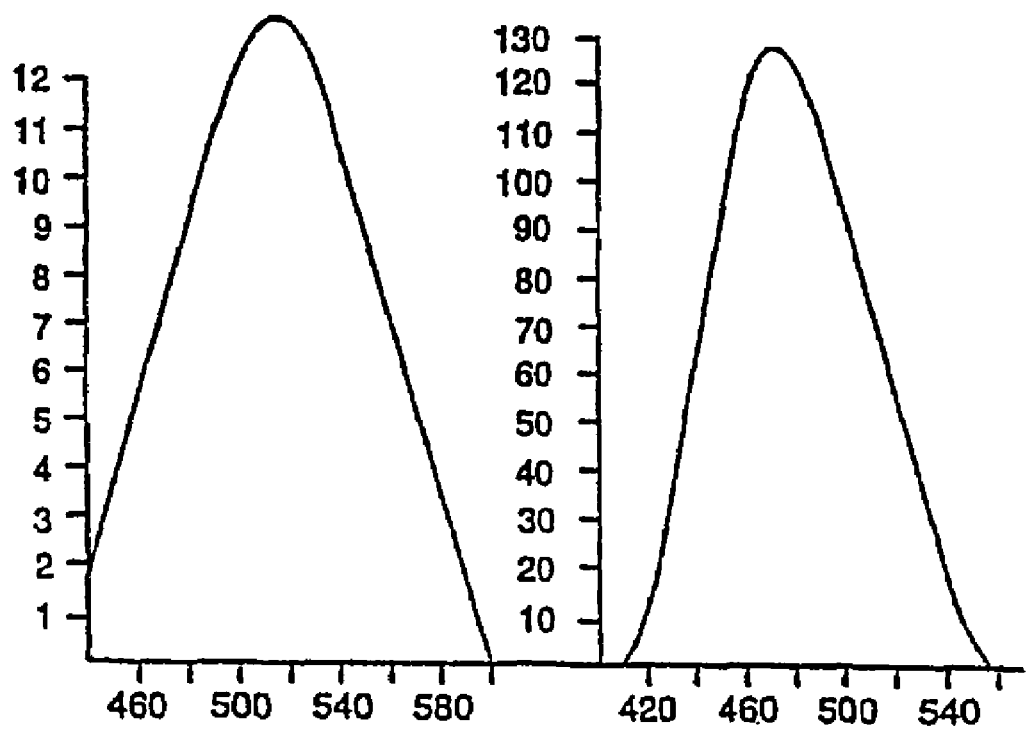

FIG. 6 shows the fluorescence peaks of primulin in solution (left), and when bound within a pure preparation of PHFs (right).

Figure 7:
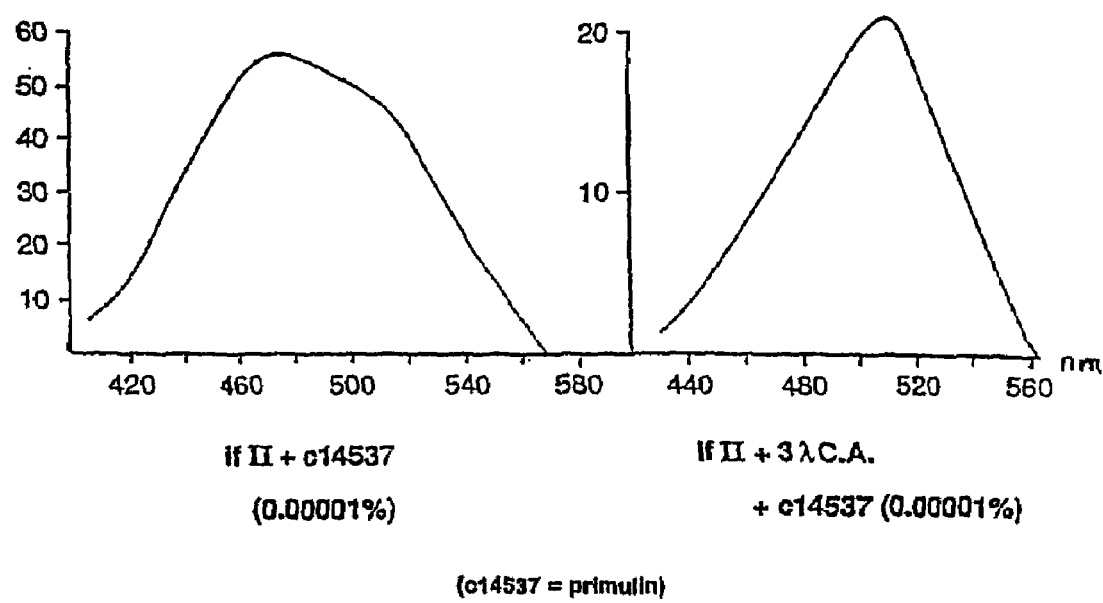

FIG. 7 shows the fluorescence peaks of primulin bound to PHFs, in the absence (left) and presence (right) of citraconic anhydride. As is shown, citraconic anhydride has the effect of disrupting the orderly structure of PHFs and releasing free tau and free unbound primulin. Citraconic anhydride also has the effect of reversing the charge on lysine residues and this may also play a role in releasing the primulin.

Figure 8A:
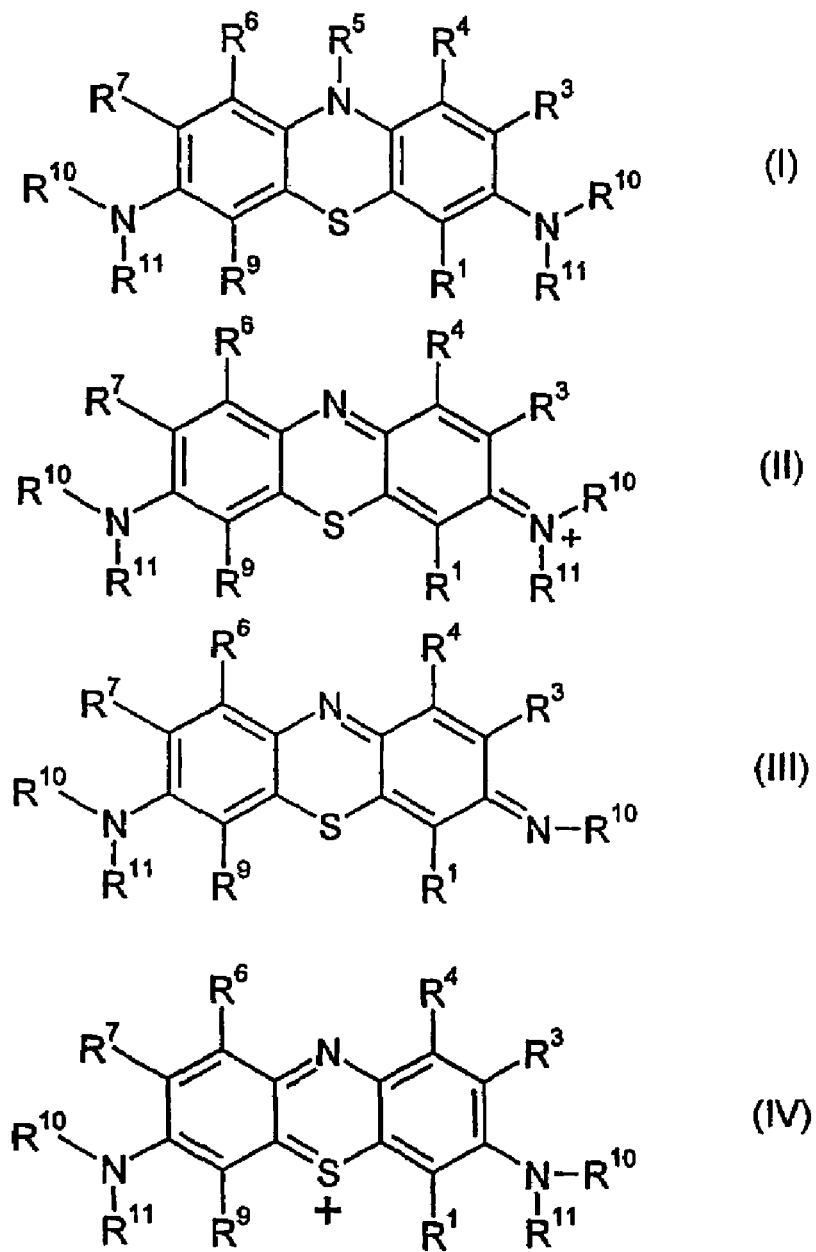
Figure 8B:
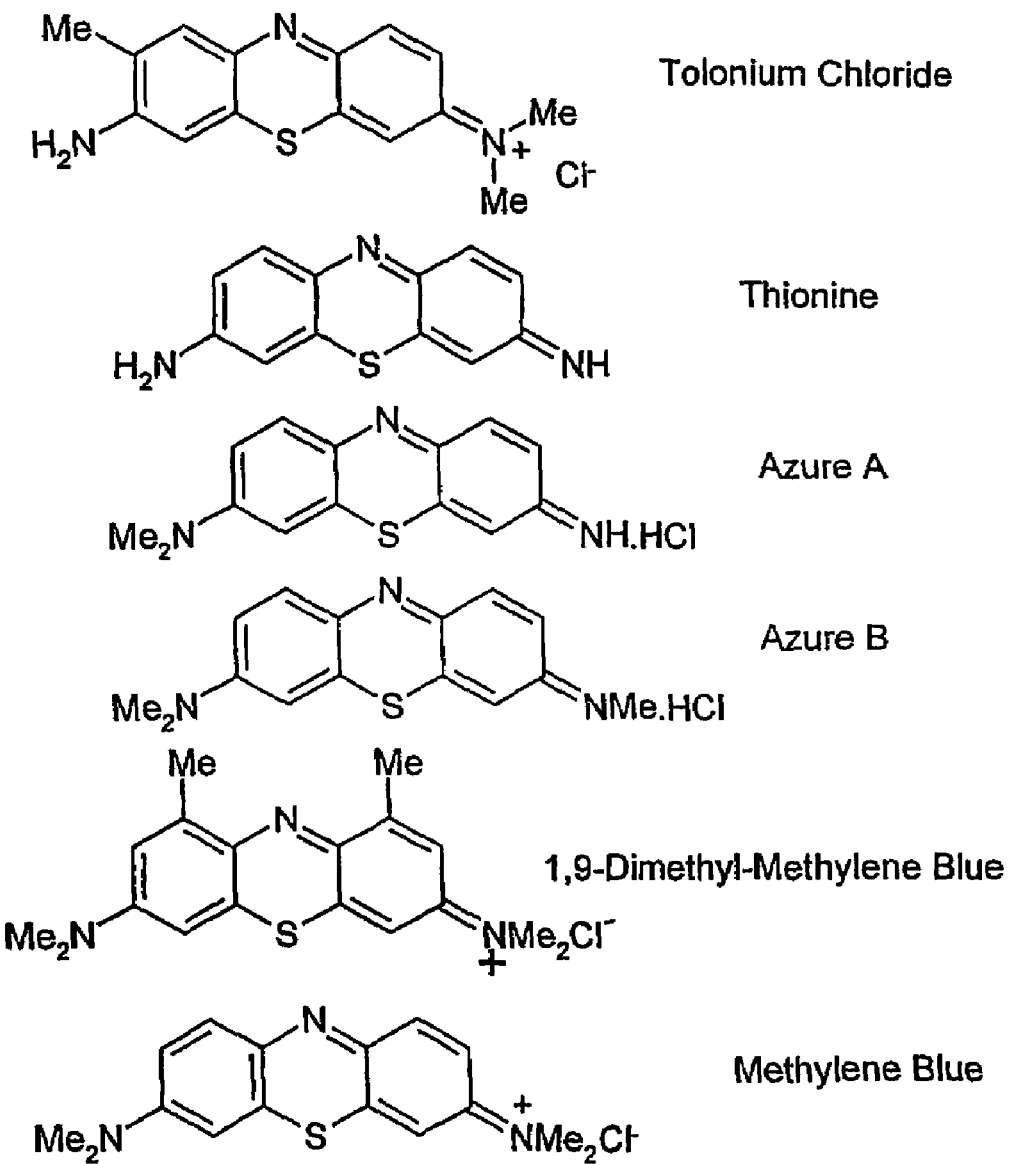

FIGS. 8a and 8b illustrate exemplary tau-tau binding inhibitors, as disclosed in WO 96/30766.

Figure 9:
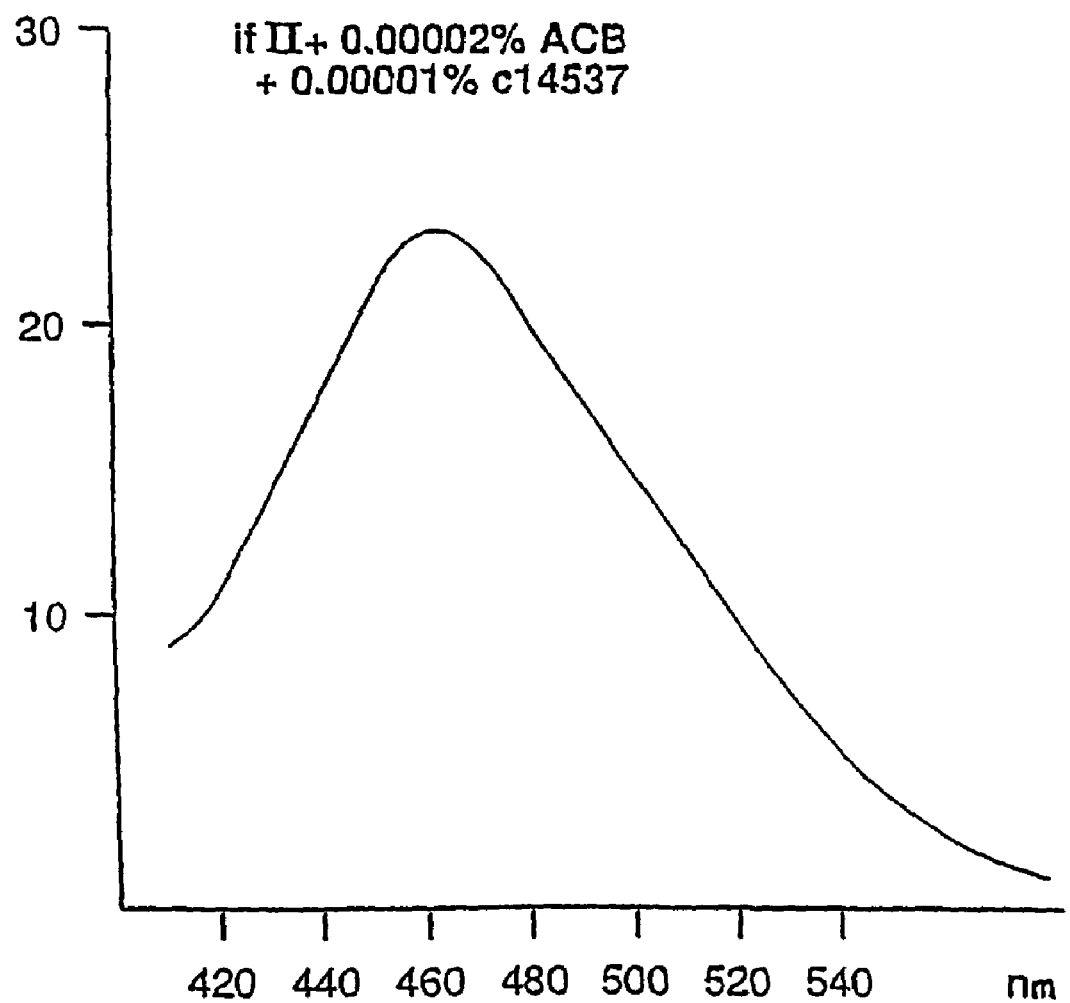

FIG. 9 shows the fluorescence of primulin bound to PHFs in the presence of alcian blue. The figure demonstrates that, in the presence of alcian blue, a disrupter of PHF structure (Ref 33), there is no disturbance of the characteristic bound primulin fluorescence peak at 460 nm.

Figure 10:
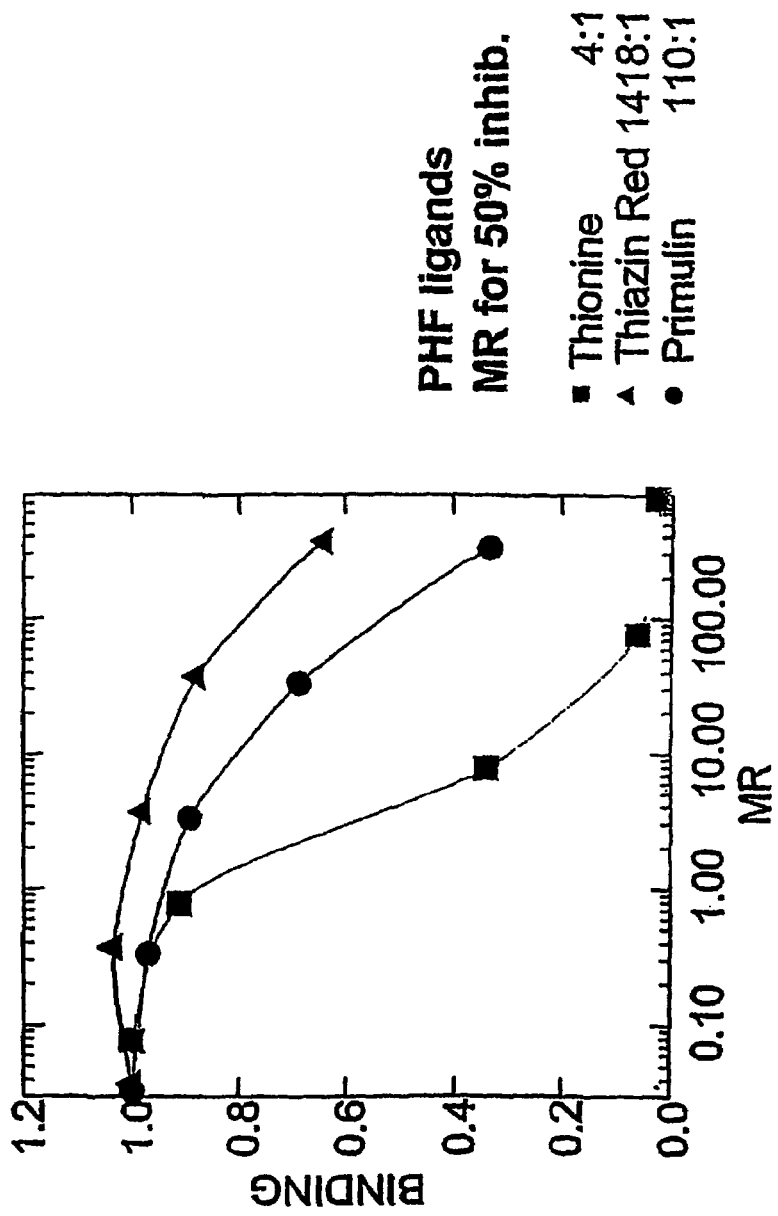

FIG. 10 shows the effect of various compounds ("MR", molar ratio of compound:tau) on tau-tau binding using tau proteins prepared according the method provided in WO96/30766 and referred to herein as "Preparation 1".

Figure 11A:
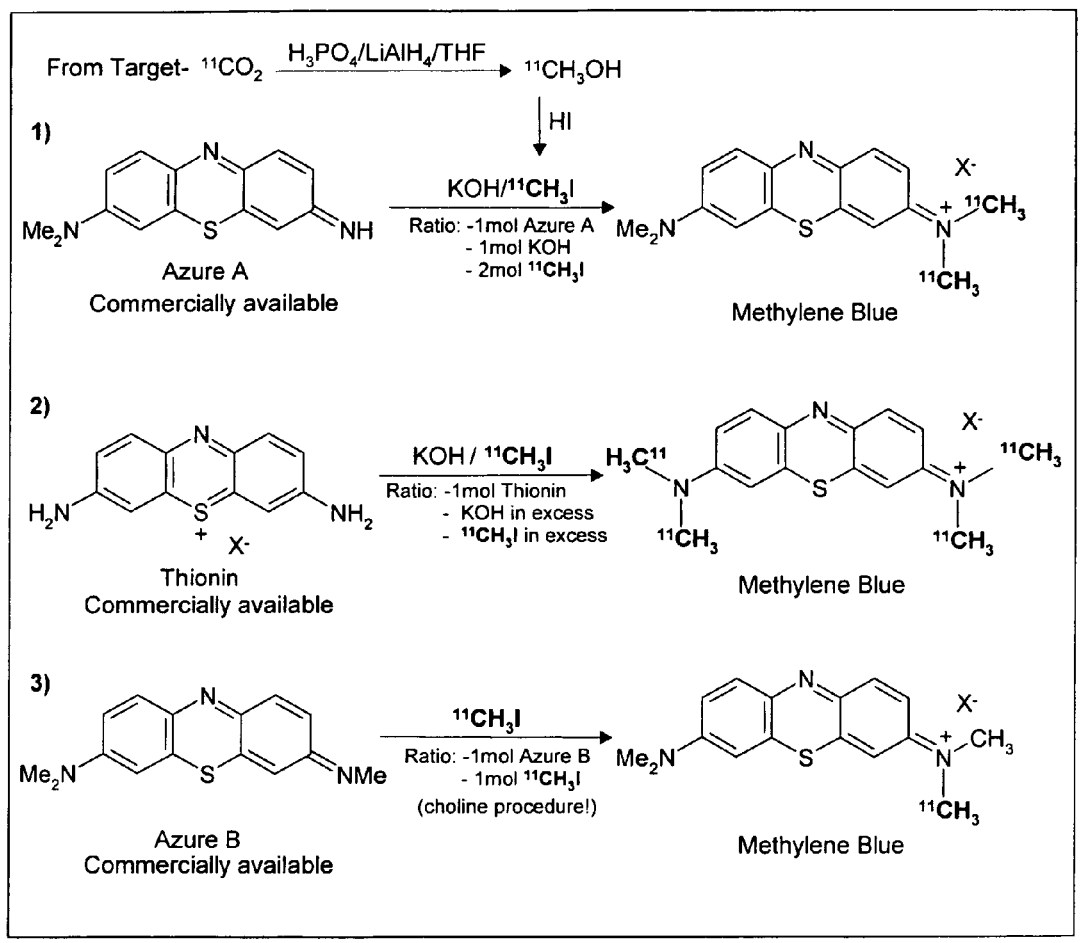
Figure 11B:
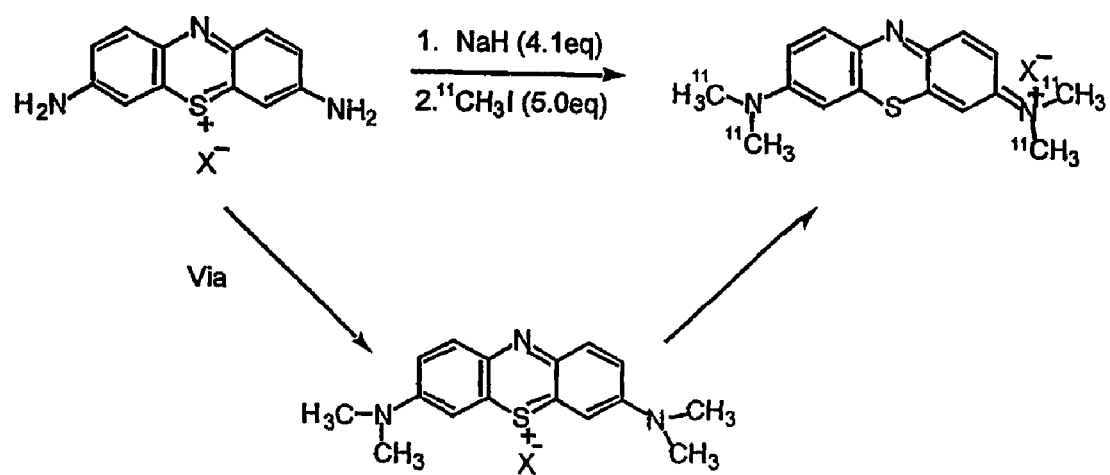

FIG. 11 show schematically the synthesis of [$^{11}$C]-labelled methylene blue. The reaction proceeds via N-methylation of the amines with [$^{11}$C]iodomethane. HPLC can be used to purify the desired product from any by-products. FIG. 11b shows a further synthesis based on thionin, NaH and $CH_3I$.

Figure 12:
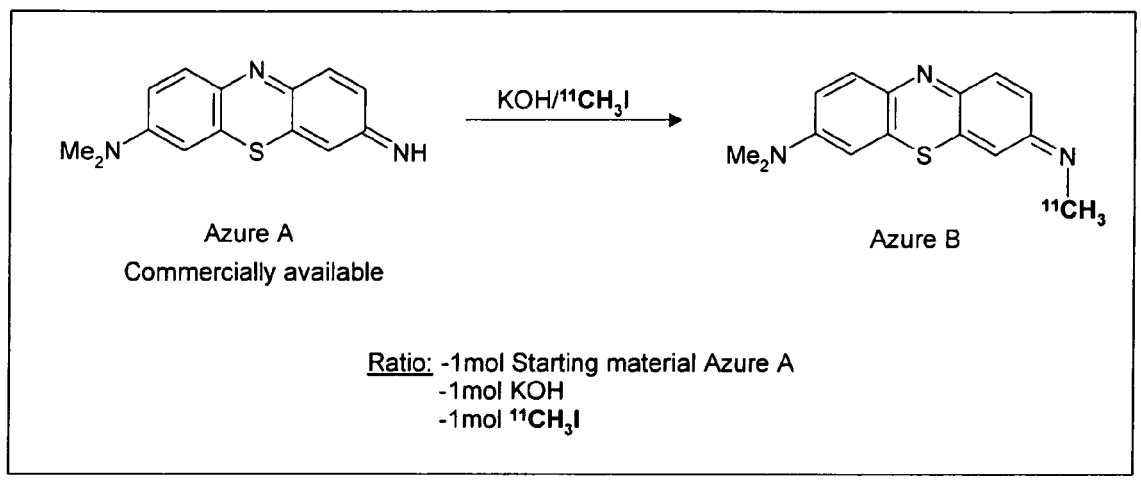

FIG. 12 shows schematically the synthesis of [$^{11}$C]-labelled Azure B. The reaction proceeds via N-methylation of the amines with [$^{11}$C]iodomethane. HPLC can be used to purify the desired product from any by-products.

Figure 13:
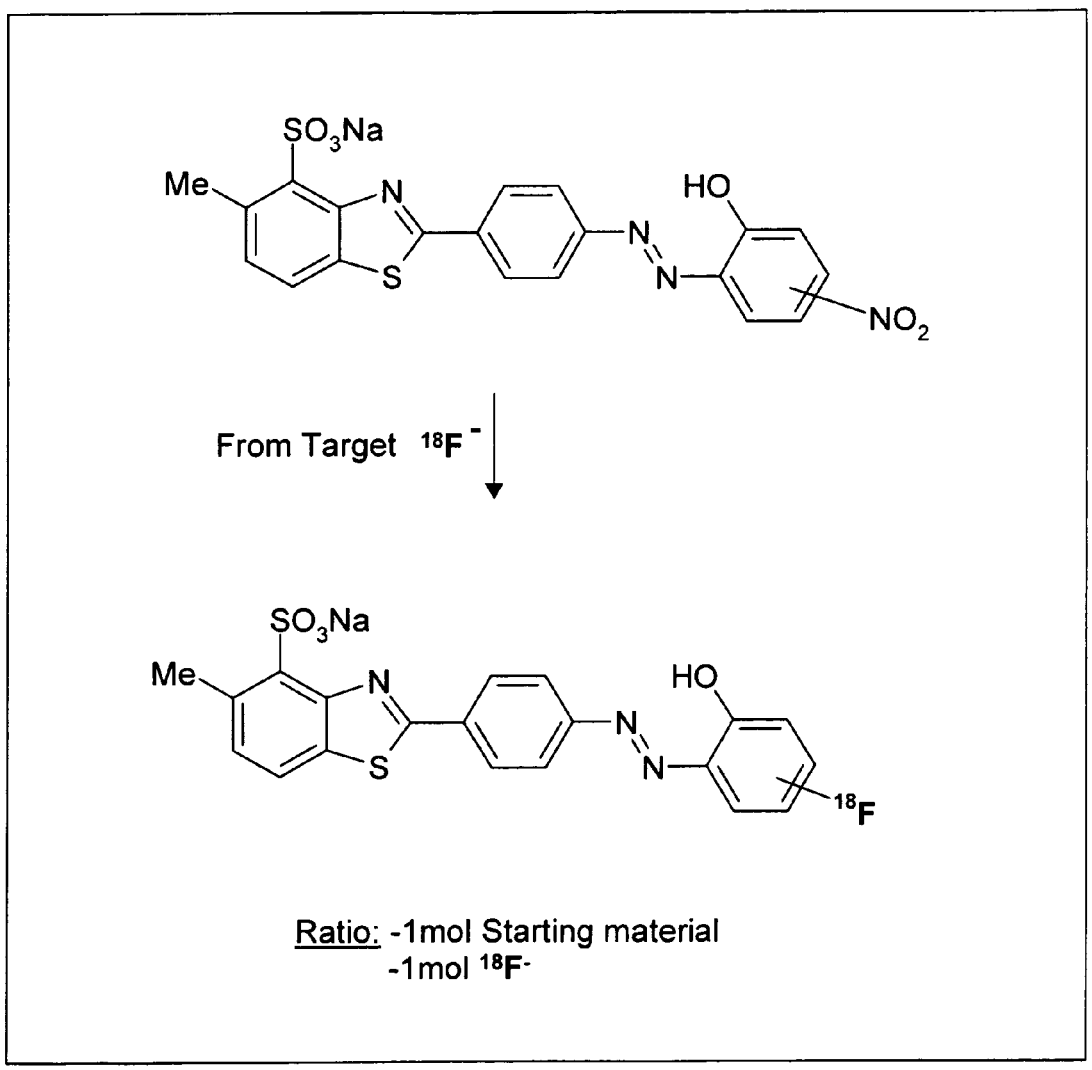

FIG. 13 shows schematically the synthesis of a [$^{18}$F]-labelled derivative of compound 4a of FIG. 4. The reaction proceeds via nucleophilic aromatic substitution whereby a nitro-group on a precursor compound is exchanged for a [$^{18}$F] fluoro group. HPLC can be used to purify the desired product from any by-products.

Figure 14:
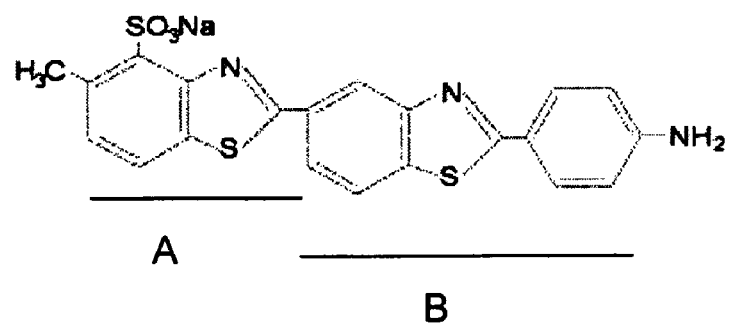
Figure 14:
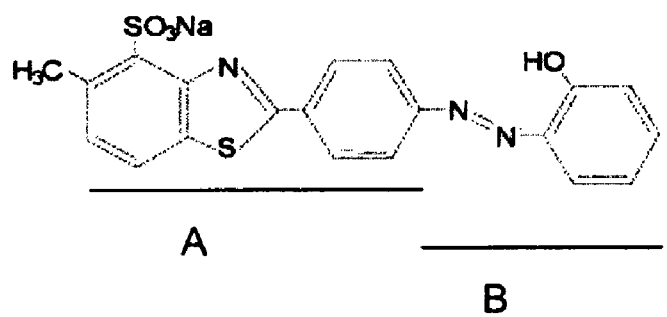
Figure 14:
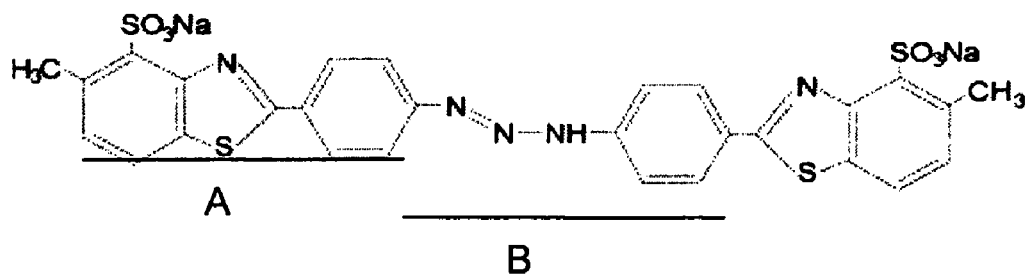

FIG. 14 shows the structures Primulin, Benthothiazole Analogue and Thiazin Yellow. The sizes of these molecules have been determined on the basis of C—C distances known from chrystal structures, and designated A and B for each molecule. The C—C lengths are as follows:

| Primulin | Minimum | 14.78 AU |
|---|---|---|
| | Maximum | 15.11 AU |
| | Mean | 14.95 AU |
| Analogue | Minimum | 15.05 AU |
| | Maximum | 15.26 AU |
| | Mean | 15.17 AU |
| Thiaz. Yellow | Minimum | 15.73 AU |
| | Maximum | 16.14 AU |
| | Mean | 15.93 AU |

Figure 15:
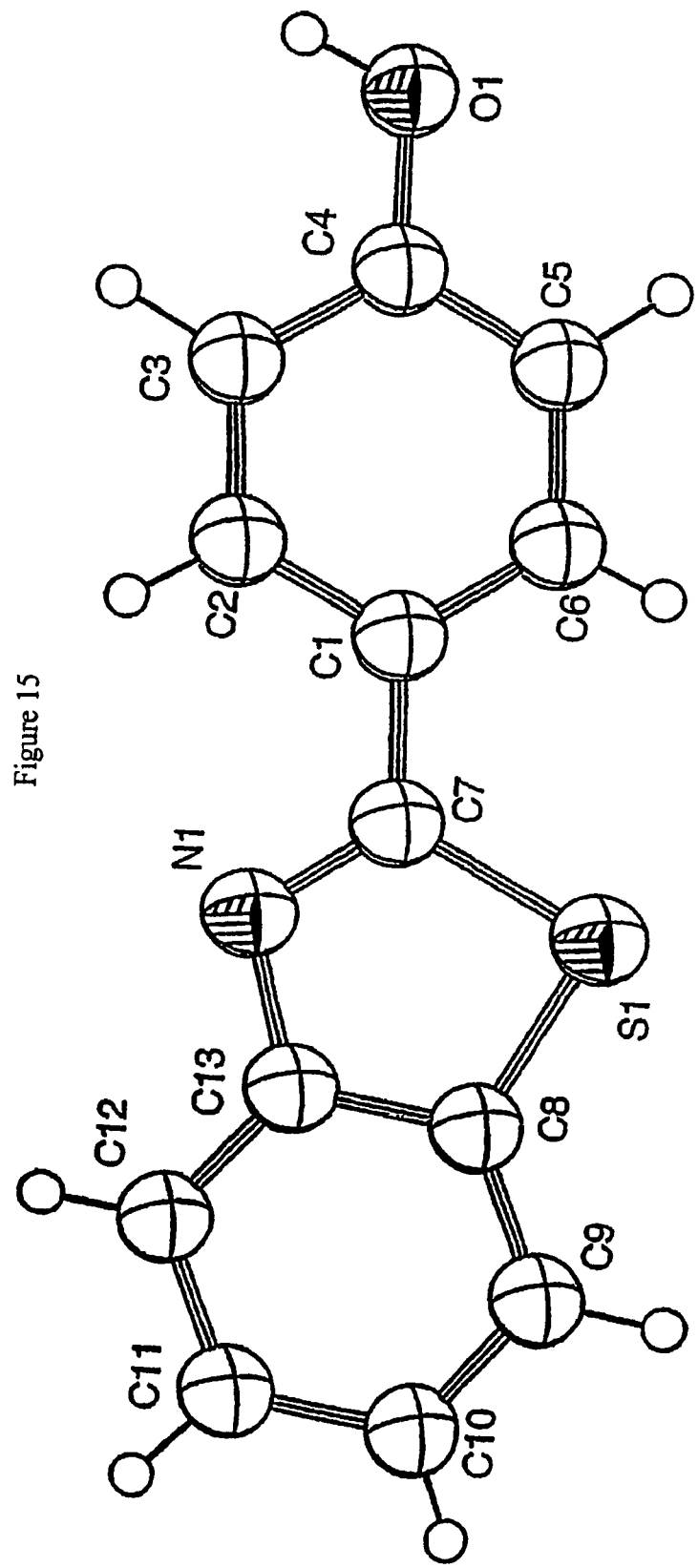
Figure 16:
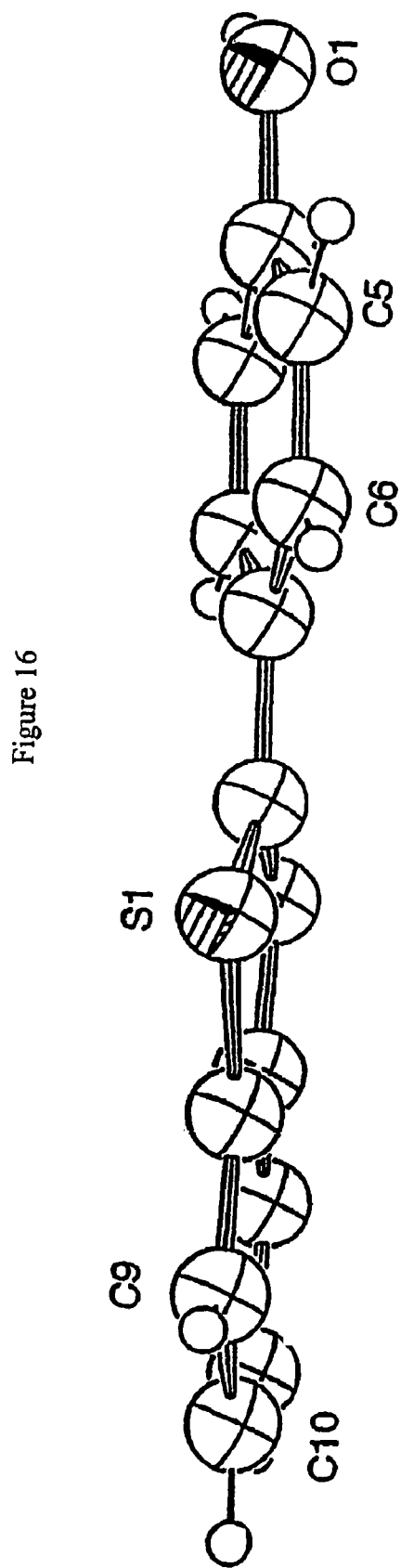

FIGS. 15 and 16 illustrate the crystal structure of the 'B' part of the primulin structure (Soon-Beng Teo et al., 1995, Acta Crystallogr., Sect. C, 591.

Figure 17:
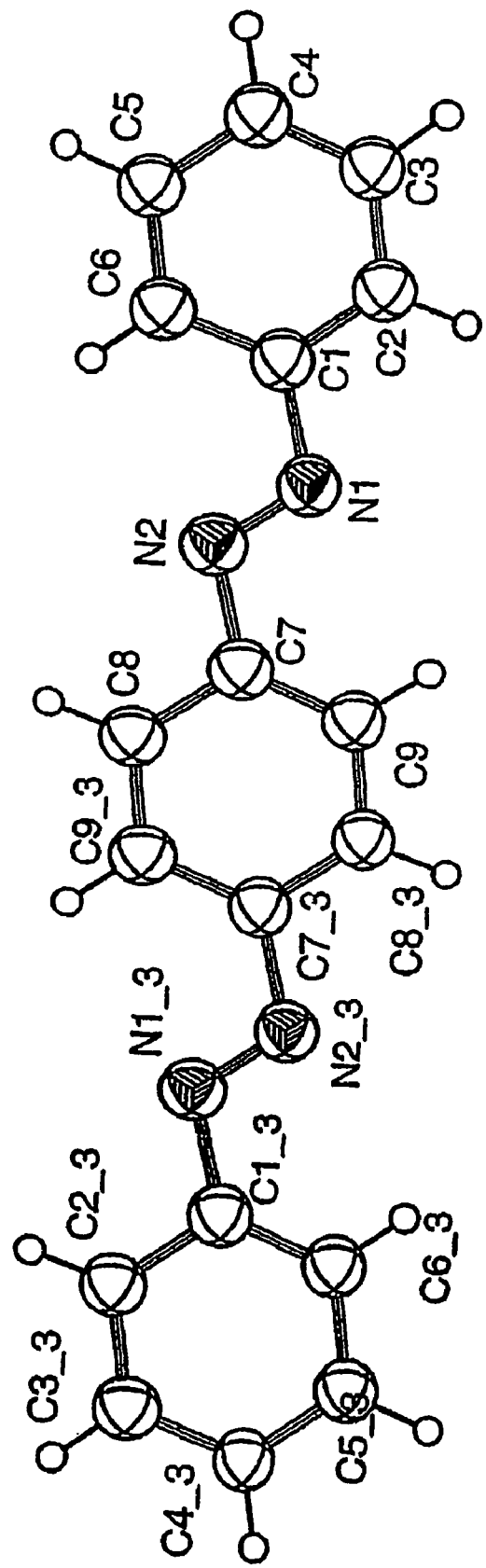
Figure 18:
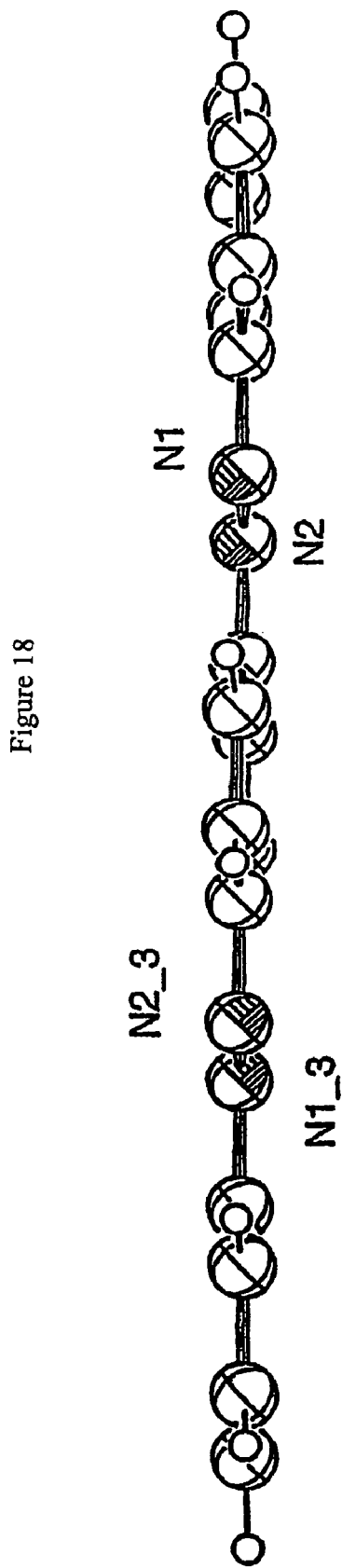

FIGS. 17 and 18 illustrate the crystal structure of a compound denoted N2A (Gilardi, R. D., 1972, Acta Chrystallogr., Sect. B, 107).

Figure 19:
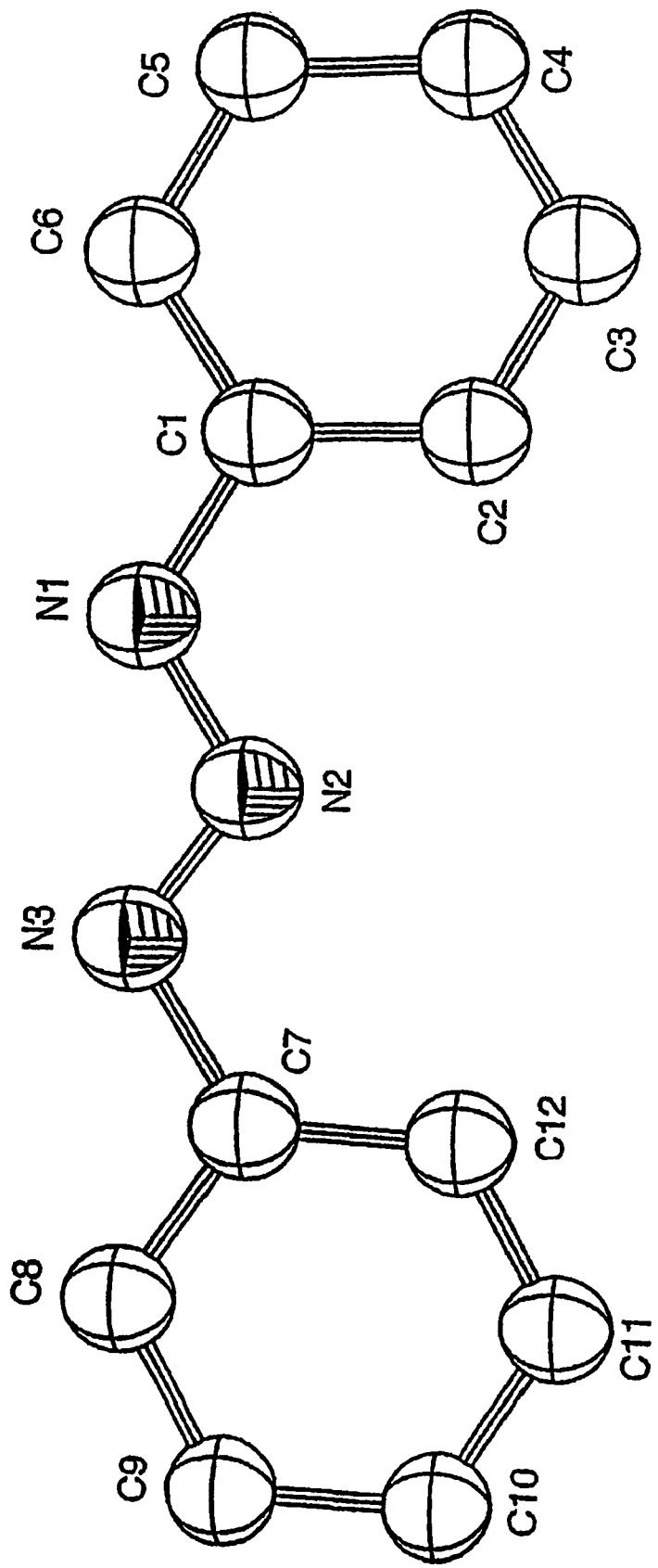
Figure 20:
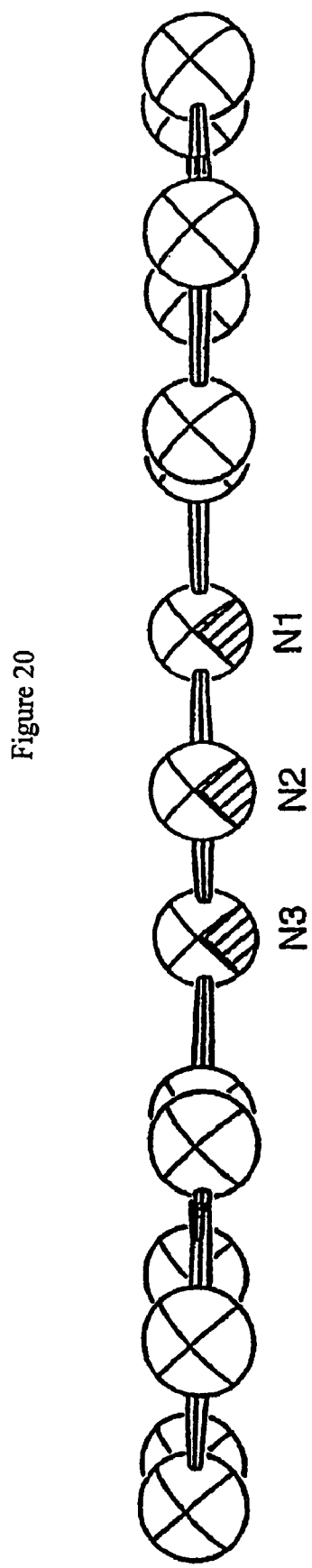

FIGS. 19 and 20 show the crystal structure of a diazoaminobenzene (Gladkova & Kondrashev, 1972, Kristallografiya (41) 17 33.

Figure 21:
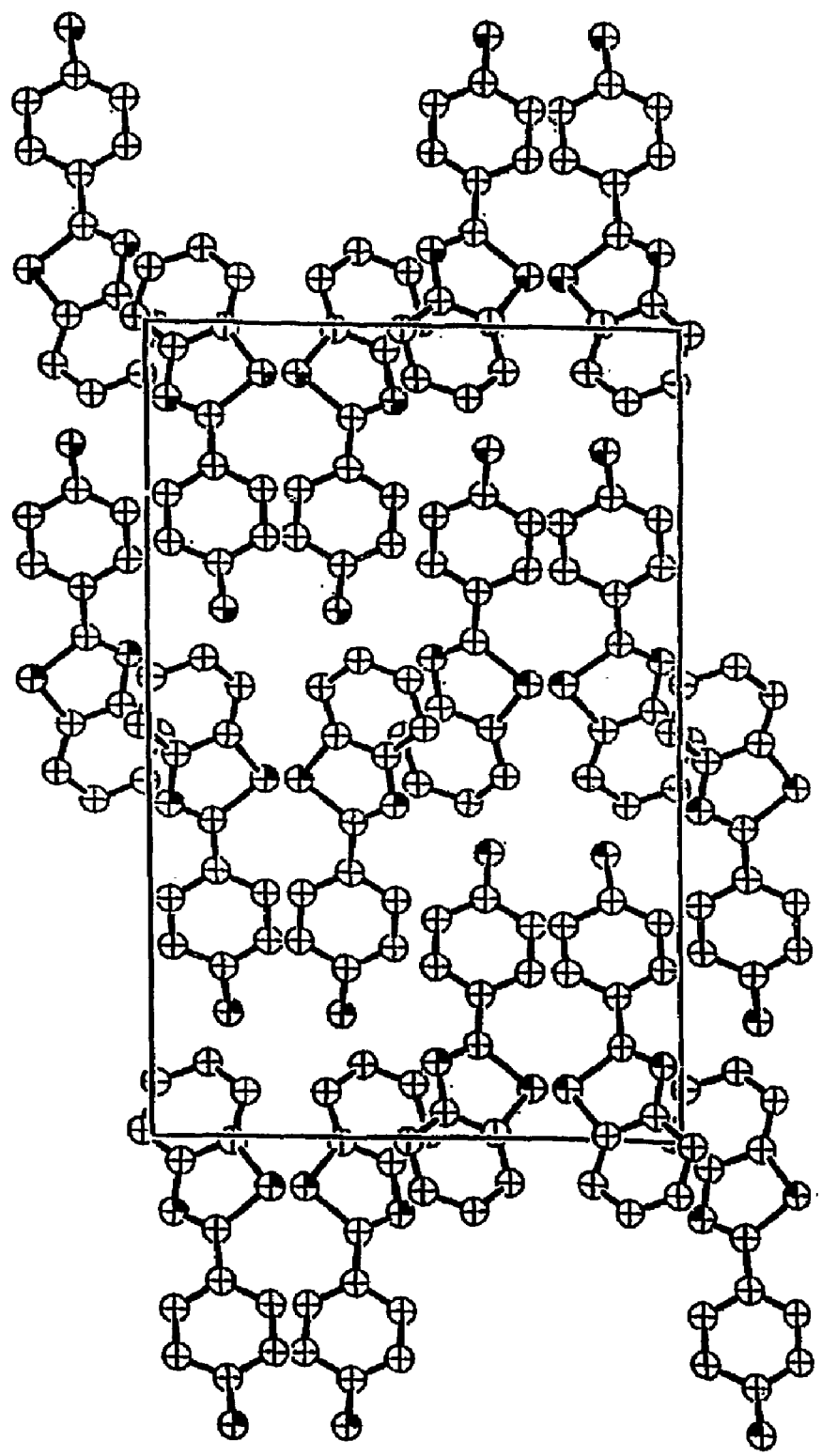
Figure 22:
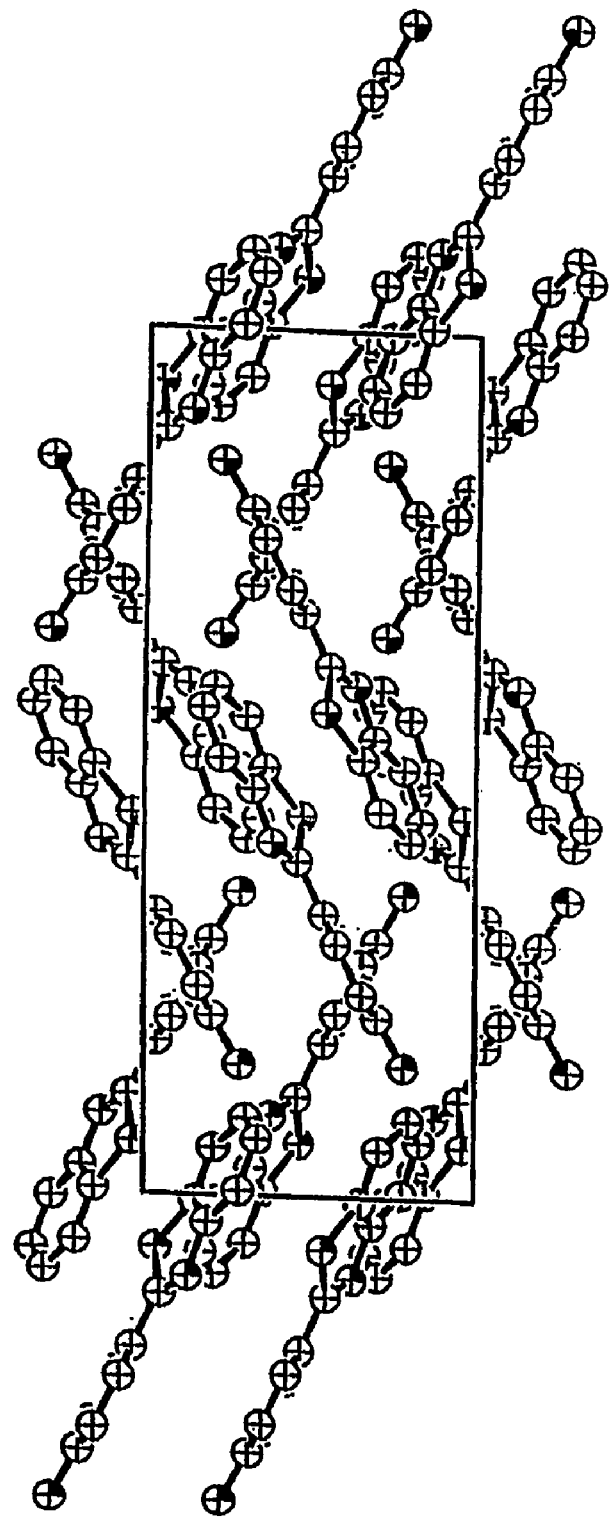

FIGS. 21 and 22 illustrate how the molecule of FIGS. 15 and 16 crystalises in space.

Figure 23:
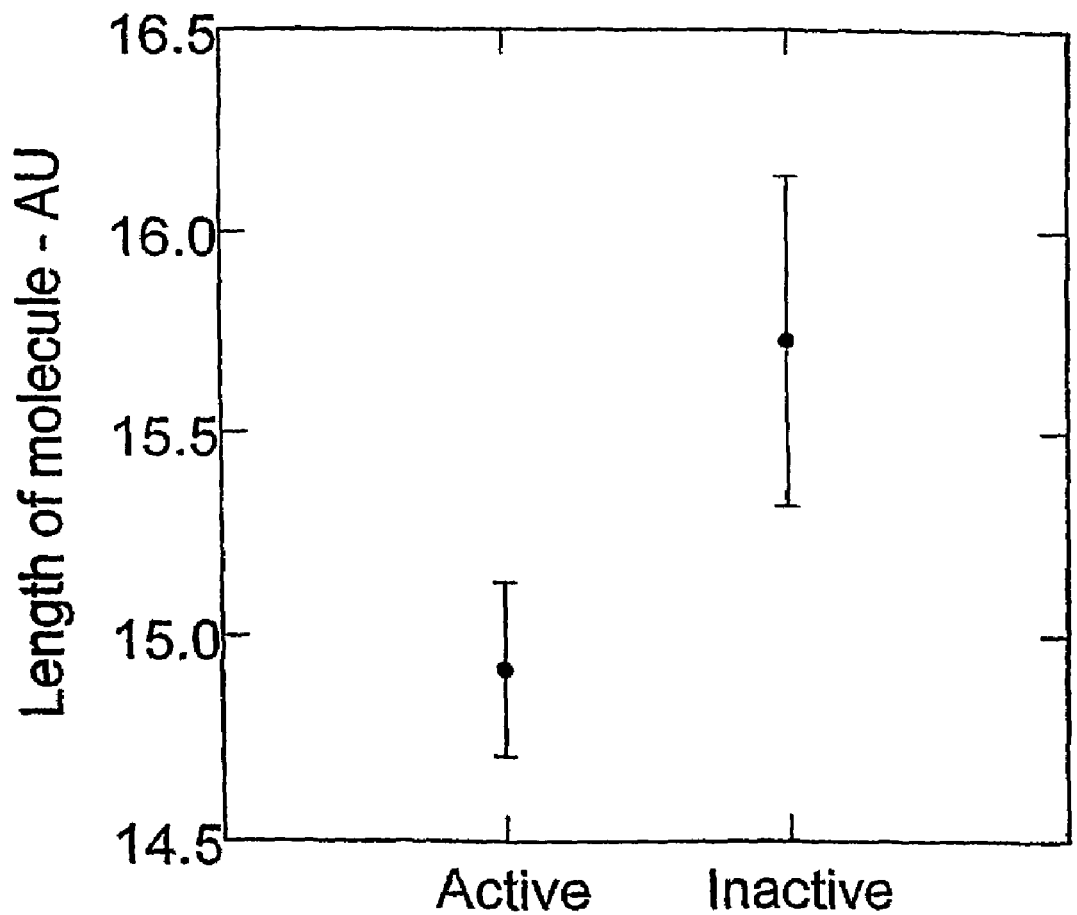

FIG. 23 shows a comparison of the mean, maximum and minimum extents of molecules which are active ligands (primulin and "analog"), and thiazin yellow (which is inactive as a ligand). The dimensions are given in angstrom units (AU).

Figure 24:
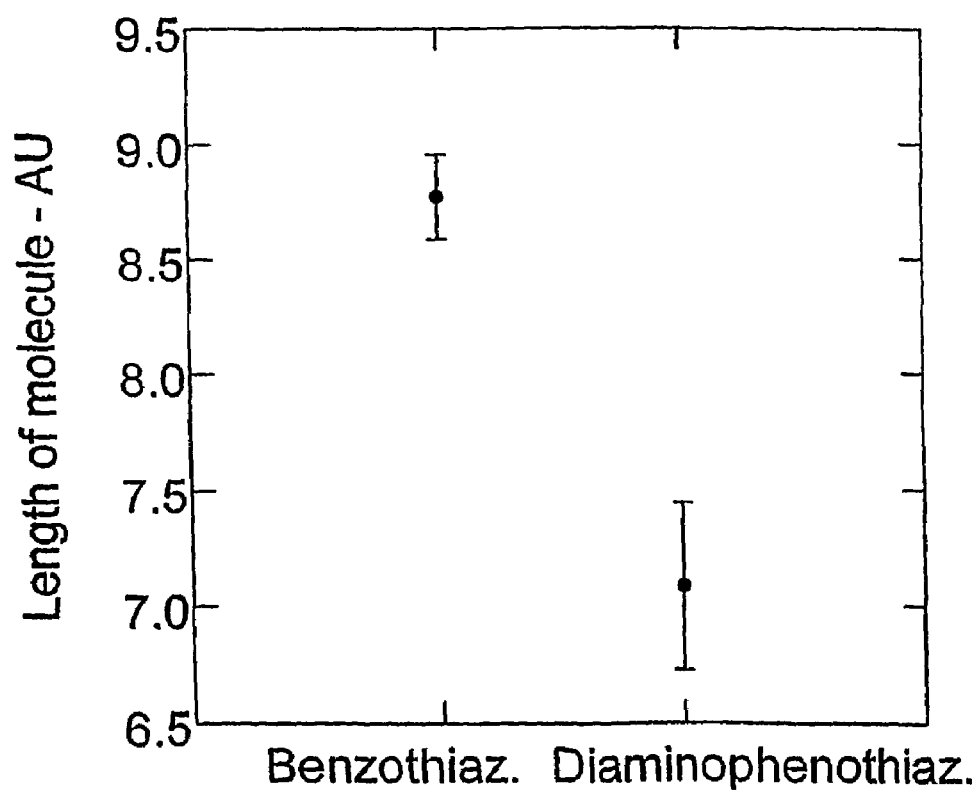

FIG. 24 shows a similar comparison for the basic benzothiazole nucleus (i.e. molecules 1b and 2 of FIG. 5) and the diaminophenothiazines. These distances are carbon-to-carbon distances.

Figure 25:
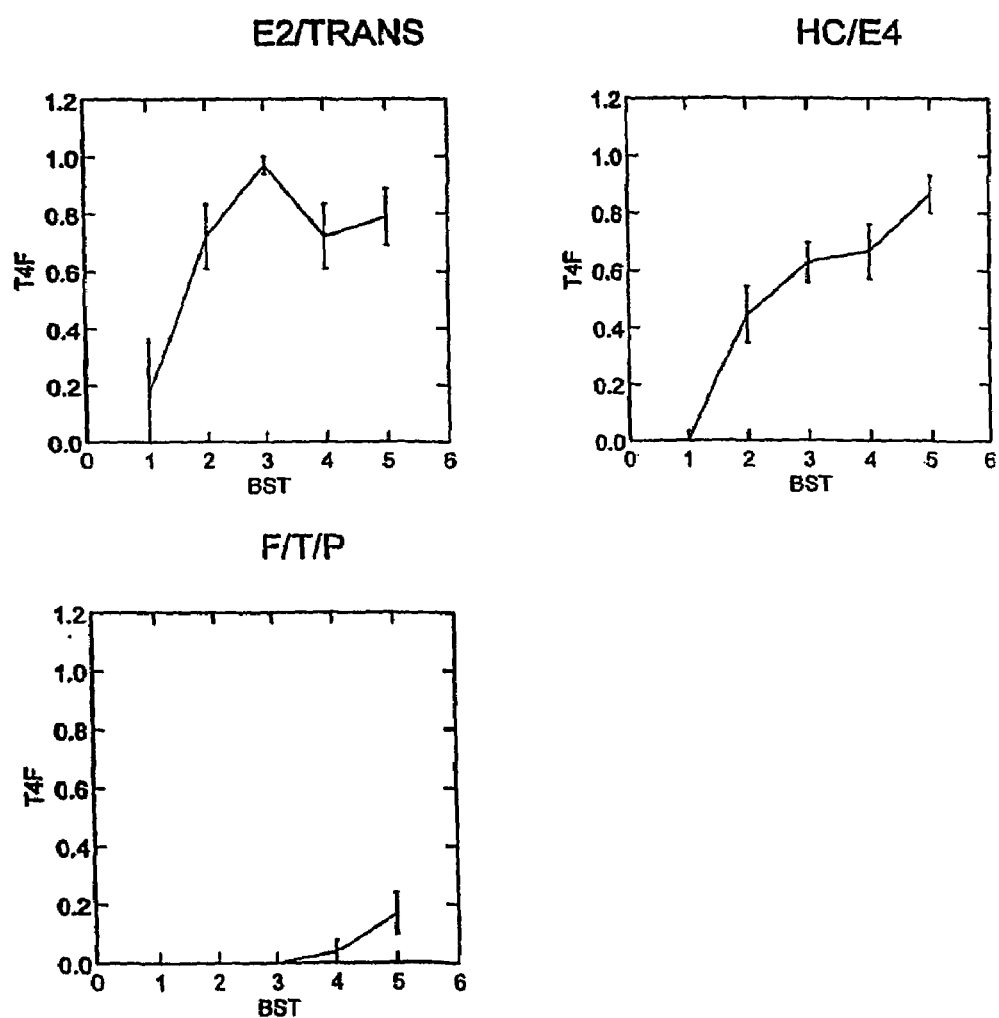

FIG. 25 shows probability of extracellular tangles as a function of Braak staging. Stages 2-4 can be clearly distinguished from stage 1 on the basis of probability of extracellular tangles in E2/Trans and E4/HC.

Figure 26:
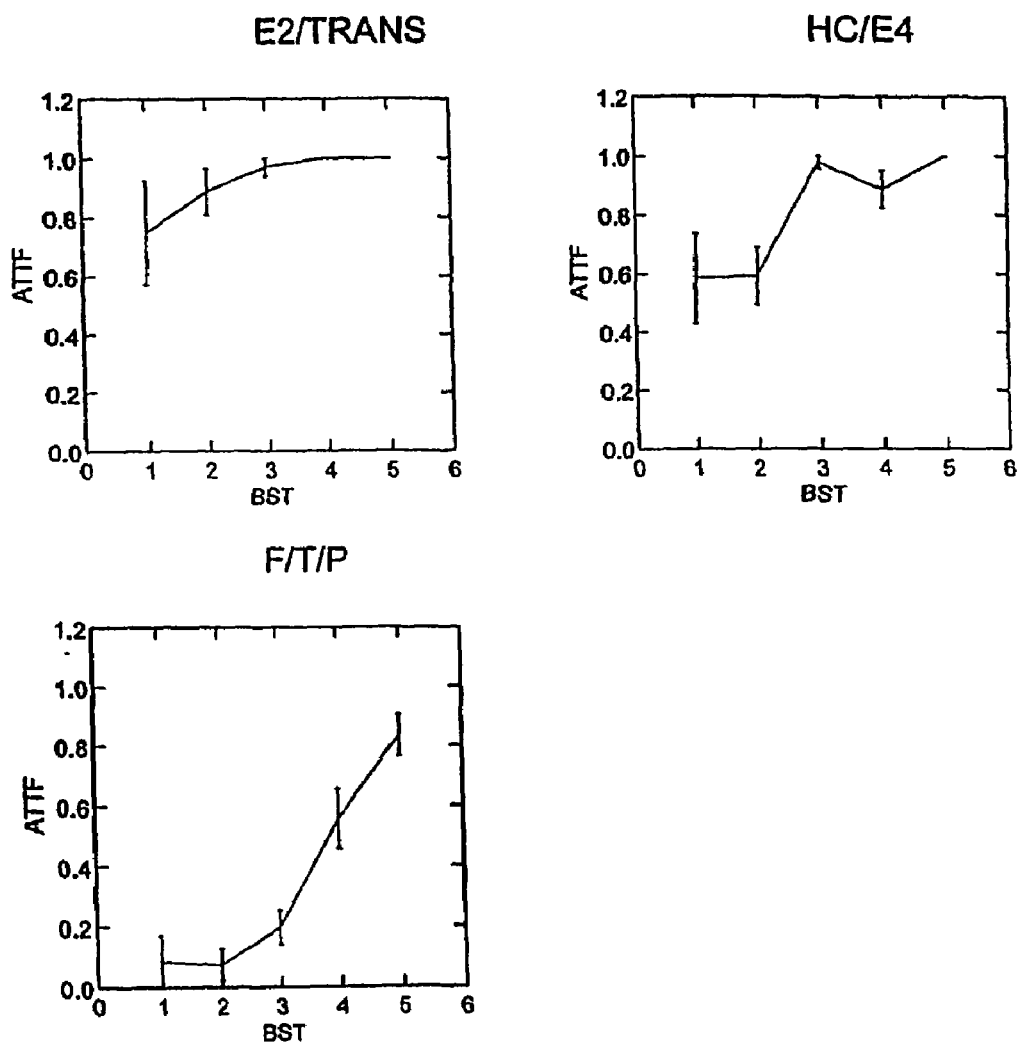

FIG. 26 shows probability of intracellular tangles as a function of Braak staging. Intracellular tangles provide a poor basis for discrimination of early stages in these regions, but a good basis for discriminating stages 4 and 5 using neocortical regions.

Figure 27:
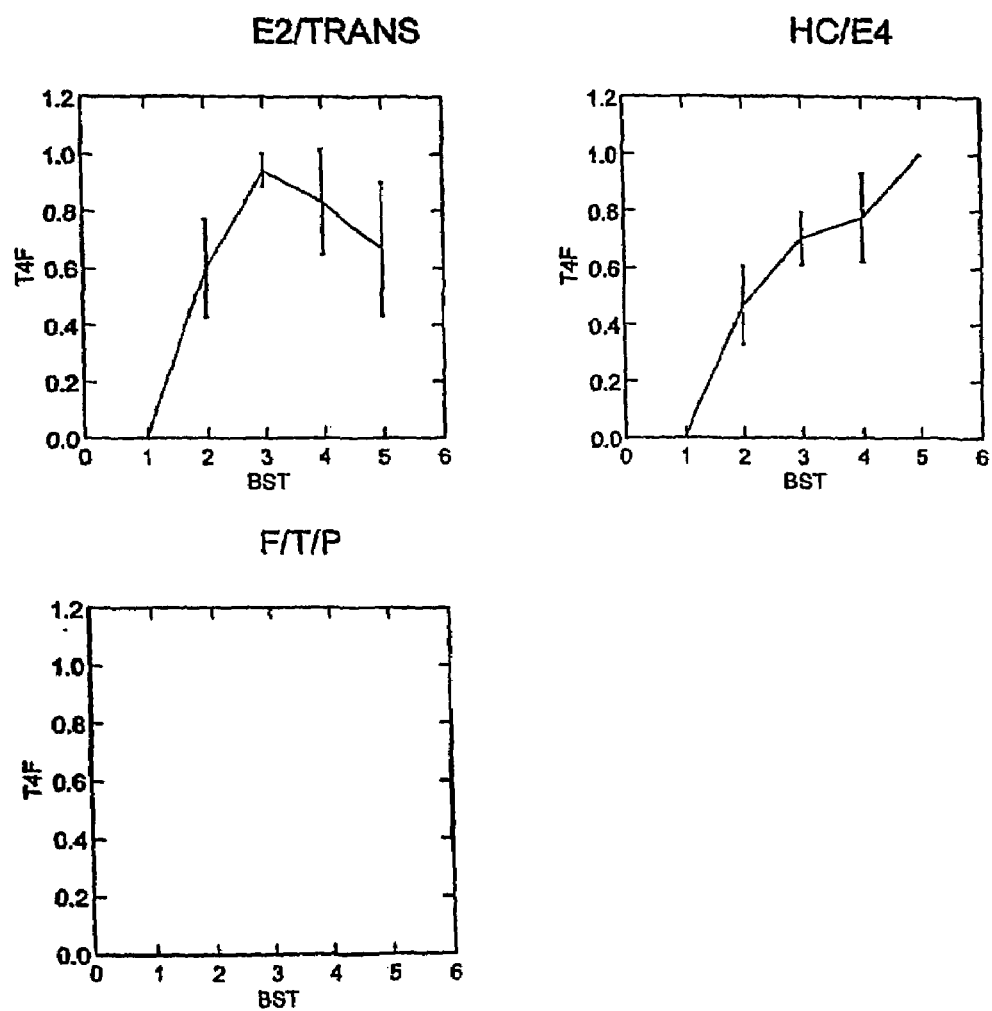

FIG. 27 corresponds to FIG. 25, but wherein cases with MMSE scores greater than 21 in the 12 months prior to death were selected. Similar results are obtained.

Figure 28:
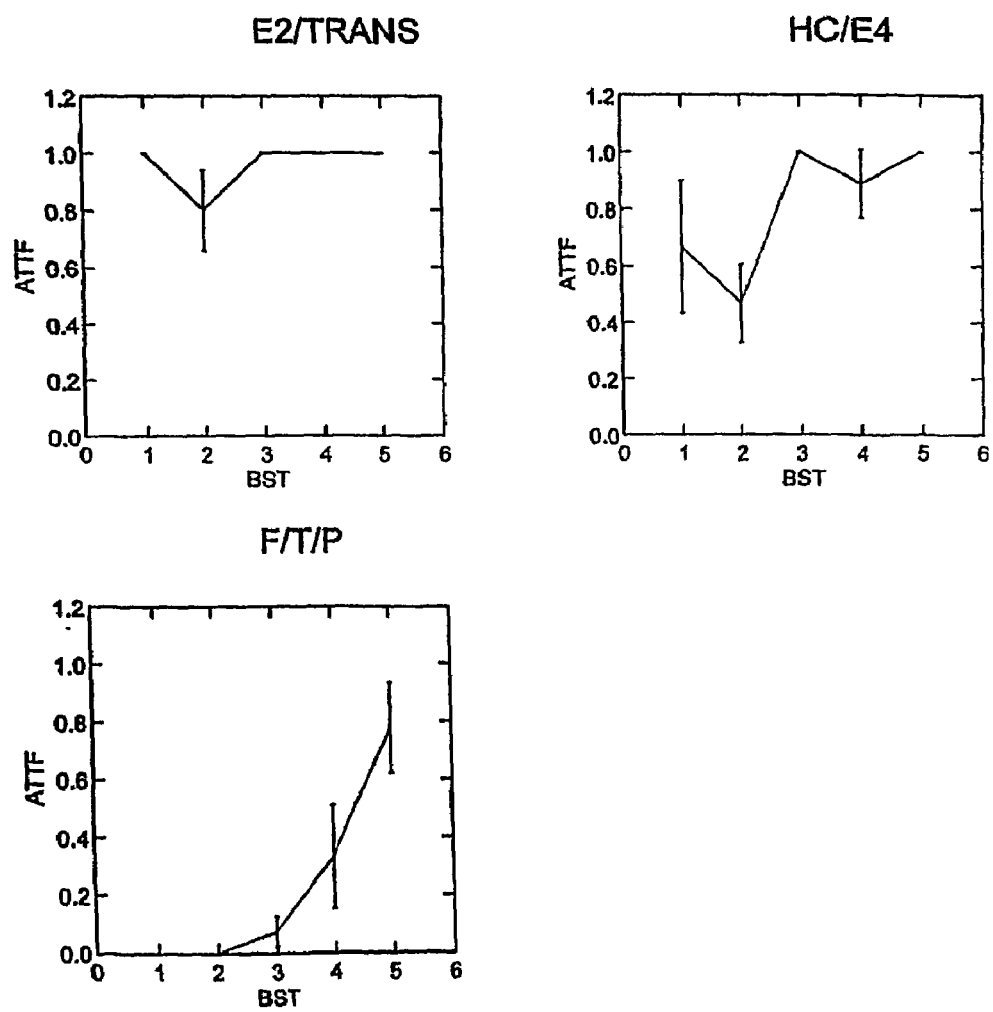

FIG. 28 corresponds to FIG. 26, but using cases with MMSE scores greater than 21 in the 12 months prior to death were selected. Similar results are obtained.

Figure 29:
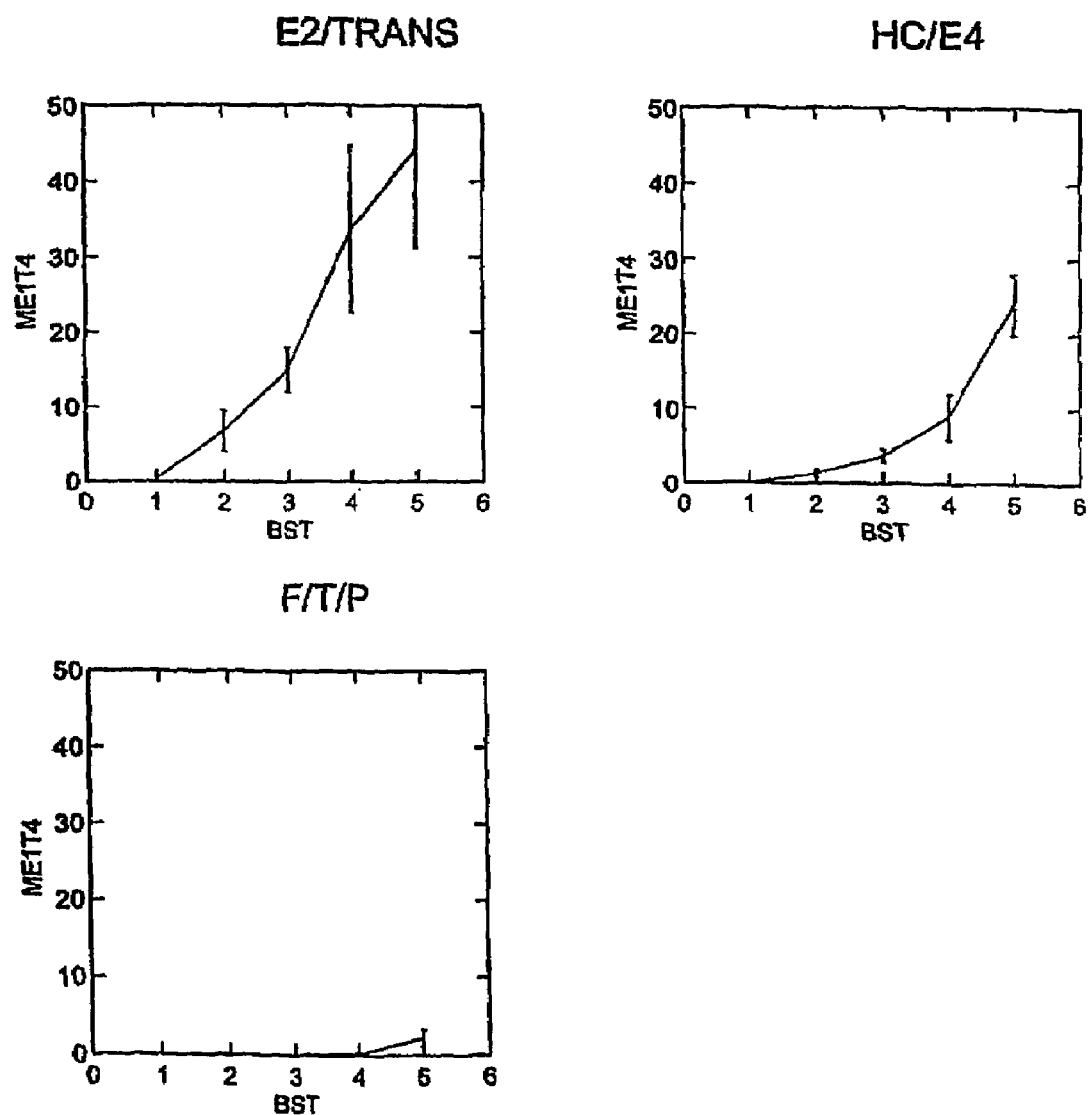

FIG. 29 shows extracellular tangle densities (counts per mm$^2$) as a function of Braak staging. Similar results are obtained to those shown in FIG. 25.

Figure 30:
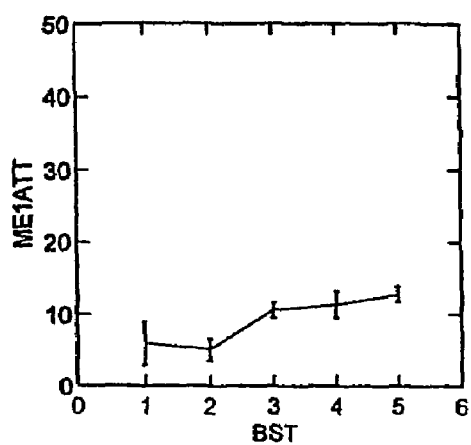
Figure 30:
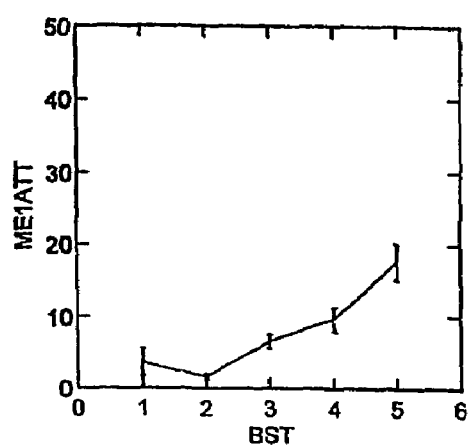
Figure 30:
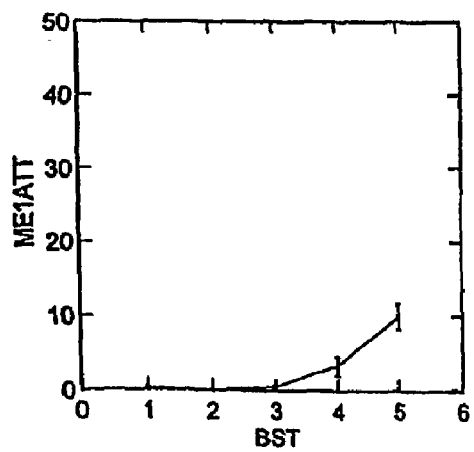

FIG. 30 shows intracellular tangle densities (counts per mm$^2$) as a function of Braak staging.

Figure 31A:
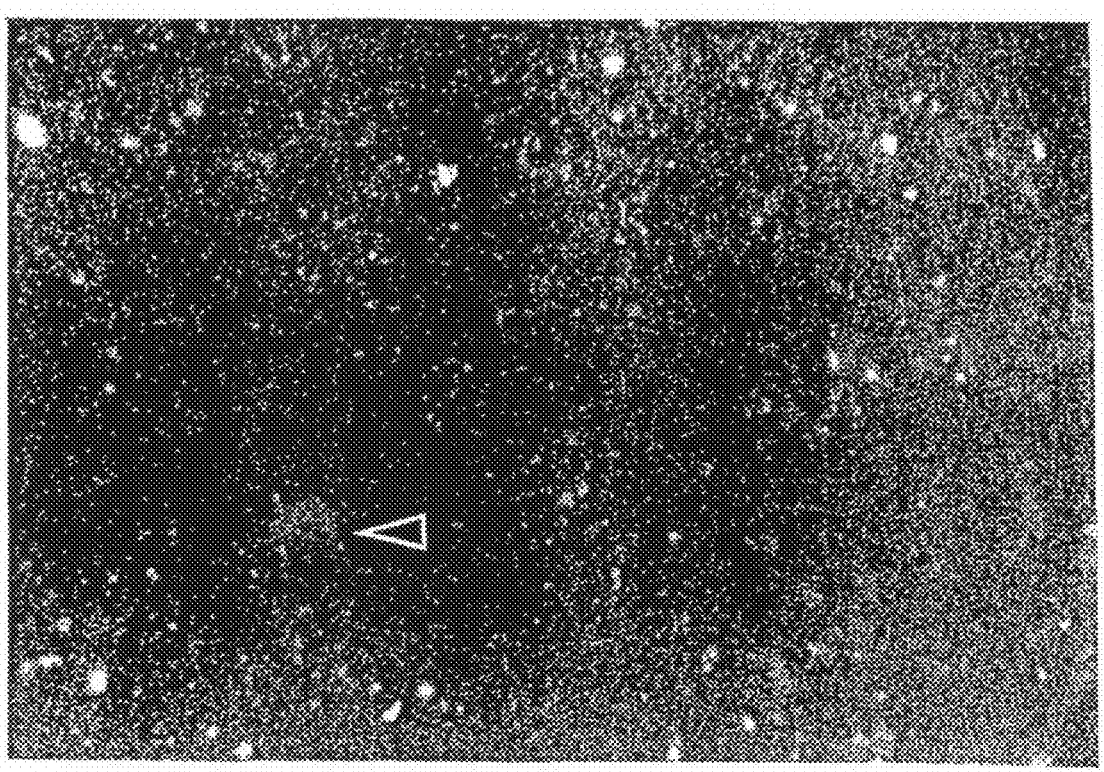
Figure 31A:
Figure 31B:
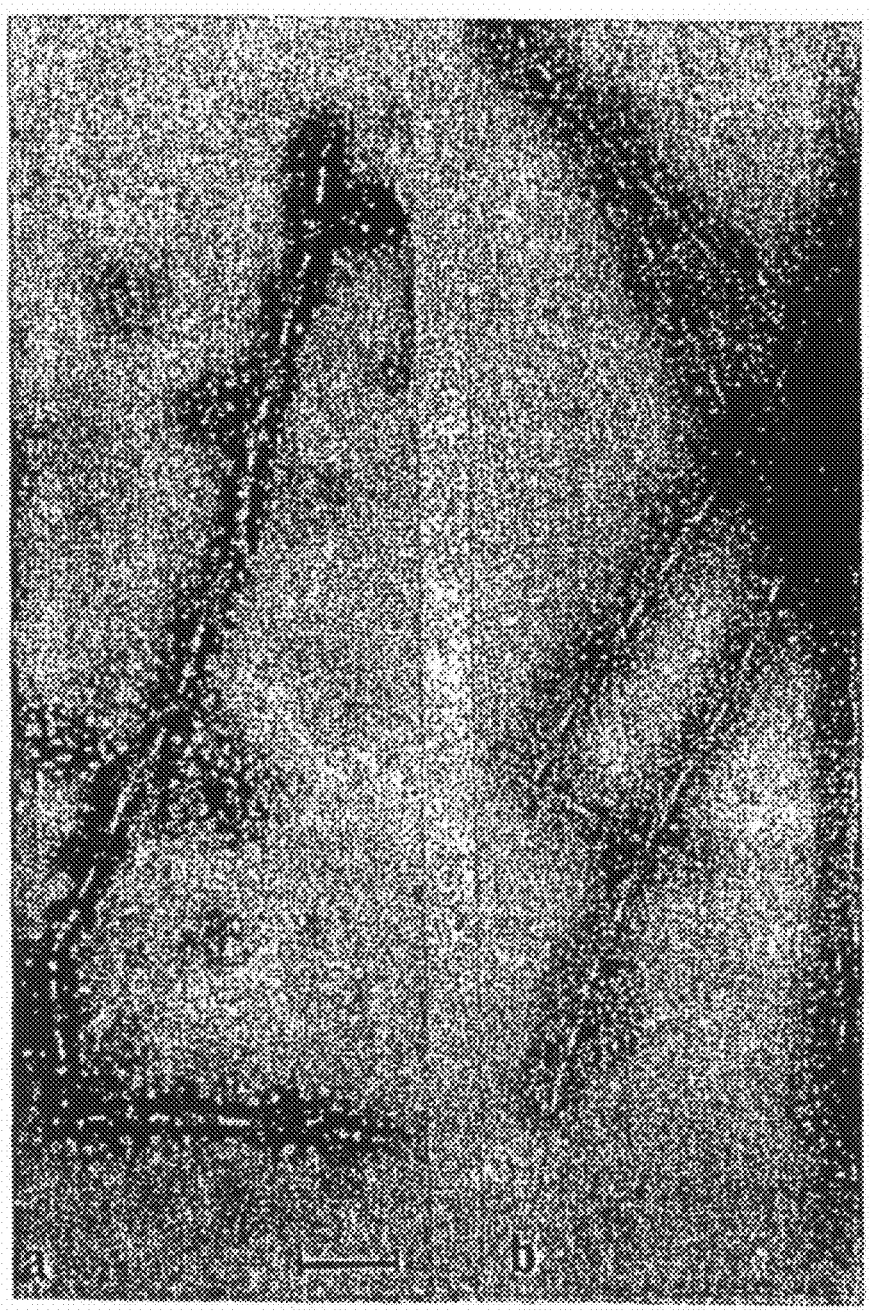

FIG. 31a shows a barely visible tangle visualised with thioflavin-T at 0.001% (arrowhead). In if1 suspensions such as this, tangles can be seen by blue fluorescence which is not distinct from that associated with binding of contaminants in the preparation. The bottom panel shows that blue tangle fluorescence produced by thioflavin-T at 0.001% is displaced by yellow tangle fluorescence produced by primulin at 0.001%. FIG. 31b shows Electron-microscopy of PHFs labelled after Pronase digestion. (a) Chemical labelling with the biotinylated benzothiazole analogue shown as 4b in FIG. 4. PHFs were deposited on a carbon-coated grid after Pronase digestion, and incubated briefly with compound 4b, and then incubated with an anti-biotin antibody preparation that had been conjugated with colloidal gold. Decoration of isolated PHFs establishes that the compound 4b binds to the proteolytically stable PHF structure. (b) mAb 423 immunolabelling of isolated PHFs after Pronase digestion, followed by incubation with a gold-conjugated goat anti-mouse second antibody as described in Novak et al. 1993 (Novak M, Kabat J, Wischik C M (1993) "Molecular characterisation of the minimal protease-resistant tau unit of the Alzheimers' disease paired helical filament", EMBO J. 12: 365-370). As shown in this paper, mAb 423 lables PHFs derived from intracellular tangles (which preserve N-terminal tau immunoreactivity in the fuzzy outer coat) poorly, but Pronase digested PHFs strongly. Likewise Mena et al. (1996) (Mena R, Edwards P C, Harrington C R, Mukaetova-Ladinska E B, Wischik C M, "Staging the pathological assembly of truncated tau protein into paired helical filaments in Alzheimer's disease", Acta Neuropathol 91: 633-641) shows that in intracellular tangles mAb 423 immunoreactivity is largely occluded, but can be exposed by formic acid pretreatment of sections.

Figure 32:
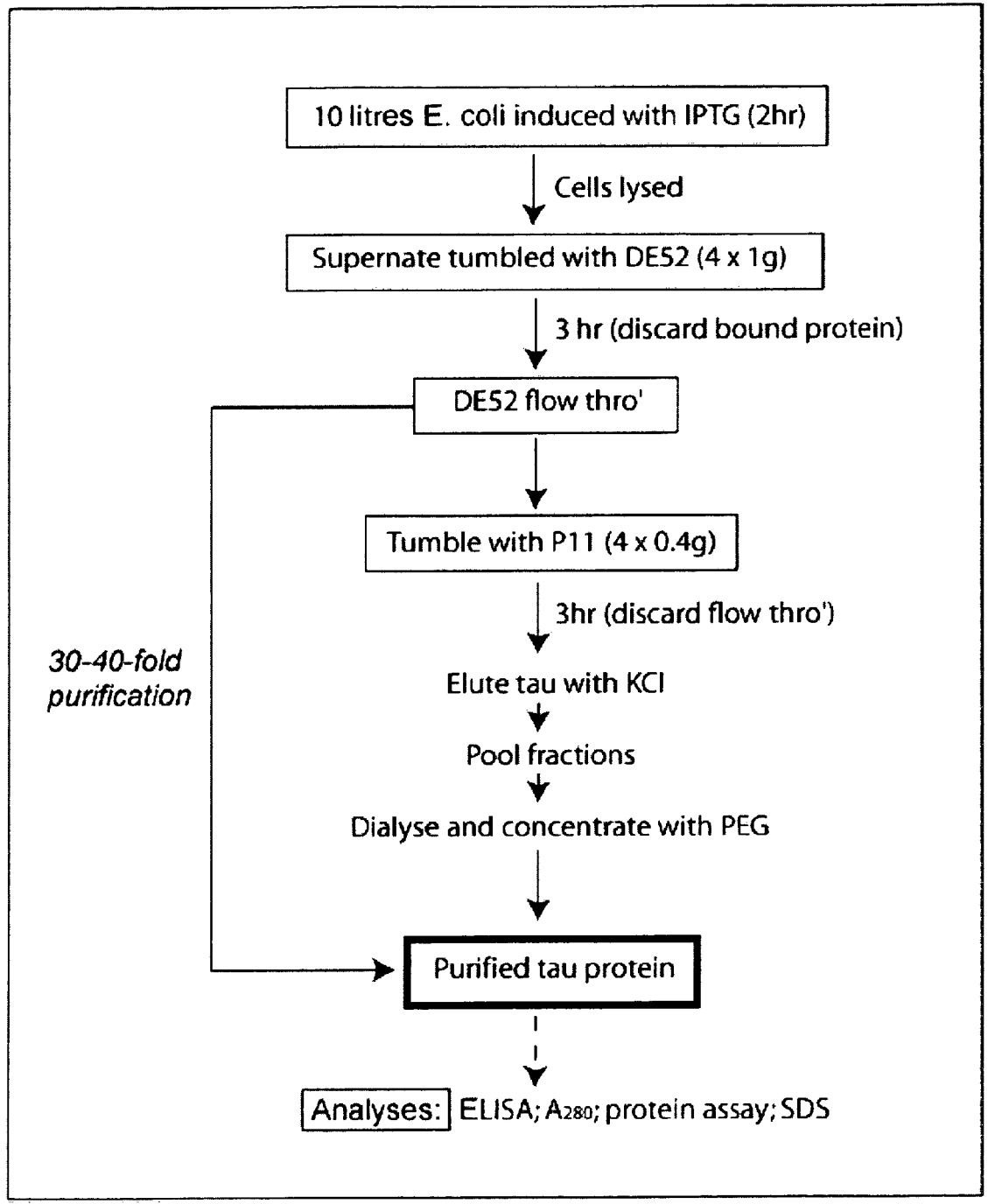

FIG. 32 shows "Preparation 2" of purified tau protein as described in Example 7 below.

Figure 33:
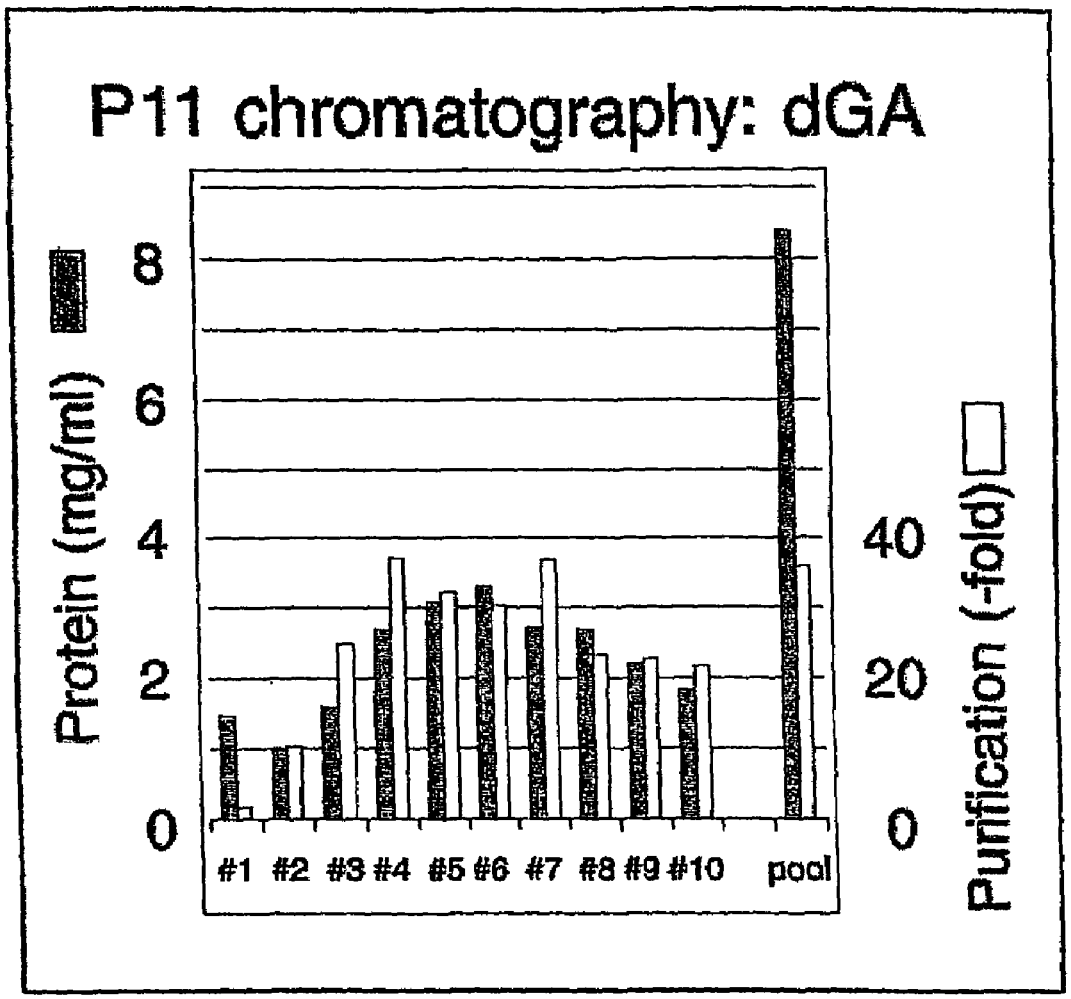

FIG. 33 shows a graphical plot of the results of a preparative run for dGA. "Purification-fold" is expressed as the ratio of specific immunoreactivity for each fraction (ie immunoreactivity/protein concentration) to specific immunoreactivity in the DE flow-through.

Figure 34:
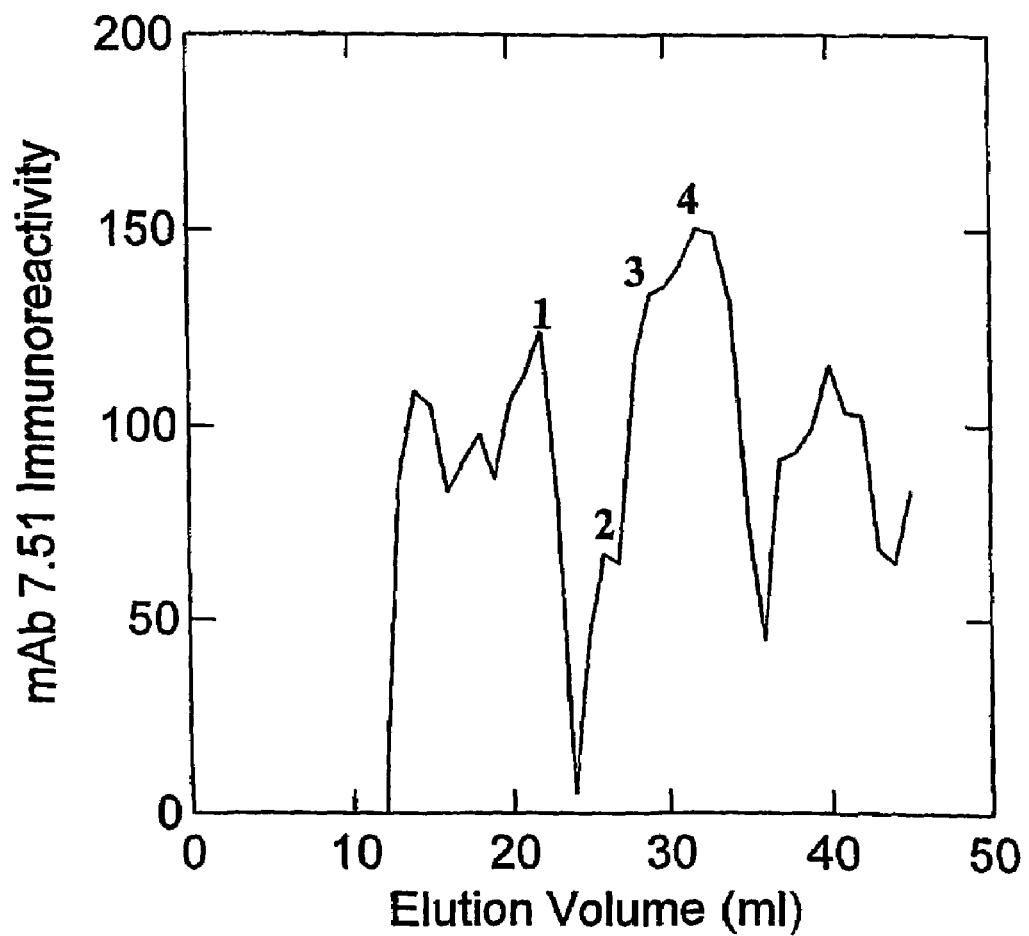

FIG. 34 shows gel filtration chromatography of purified dGAE. Apparent elution size in non-denaturing conditions:
  1-~320 kD; 2-~80 kD; 3-~30 kD; 4-~10 kD
About 64% of mAb 7.51 immunoreactivity elutes in fractions corresponding to species of size >15 kD.

Figure 35:
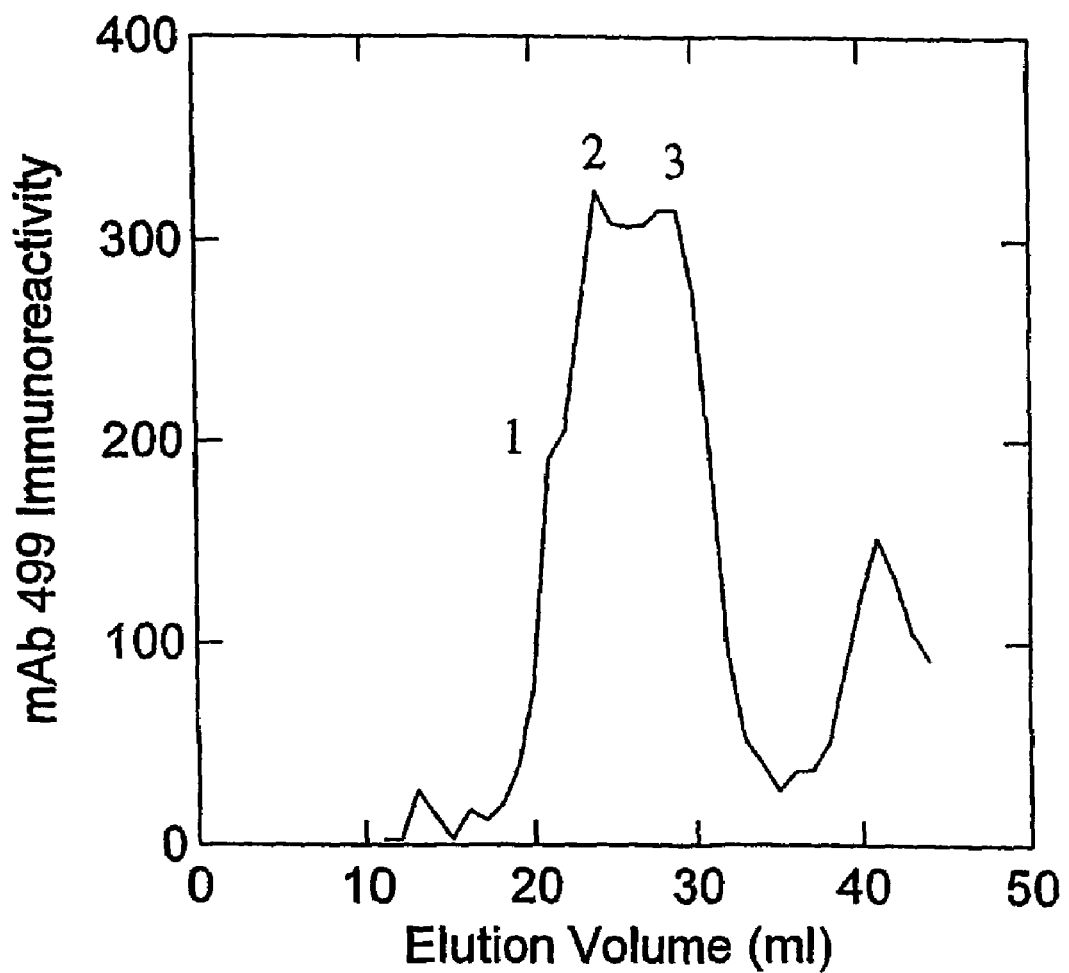

FIG. 35 shows gel filtration chromatography of purified T40. Apparent elution size in non-denaturing conditions:
  1-~450 kD; 2-~160 kD; 3-~55 kD.
About 50% of mAb 499 immunoreactivity elutes in fractions corresponding to species of size >60 kD.

Figure 36:
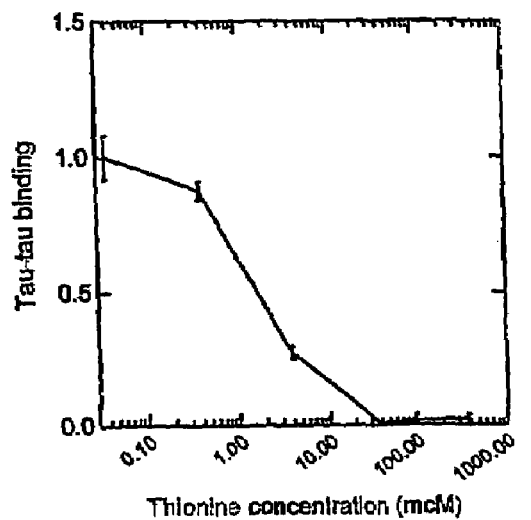
Figure 36:
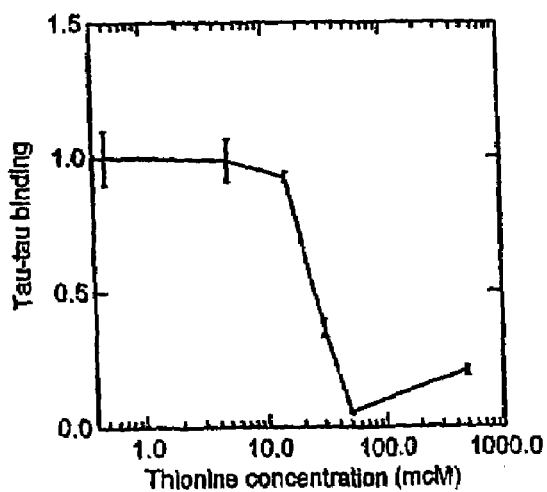

FIG. 36 shows thionine activity against tau-tau binding in Preparations 1 & 2.

Figure 37:
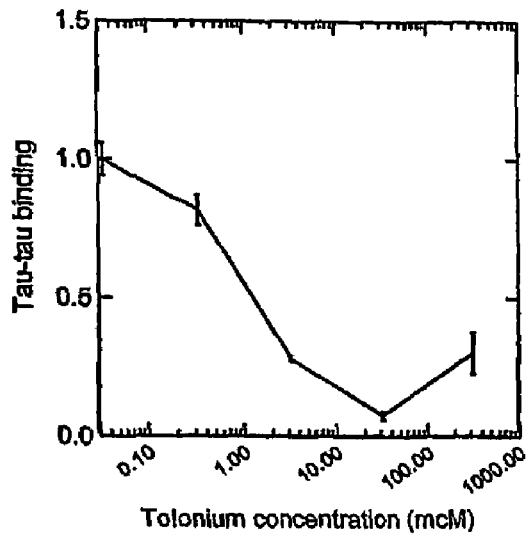
Figure 37:
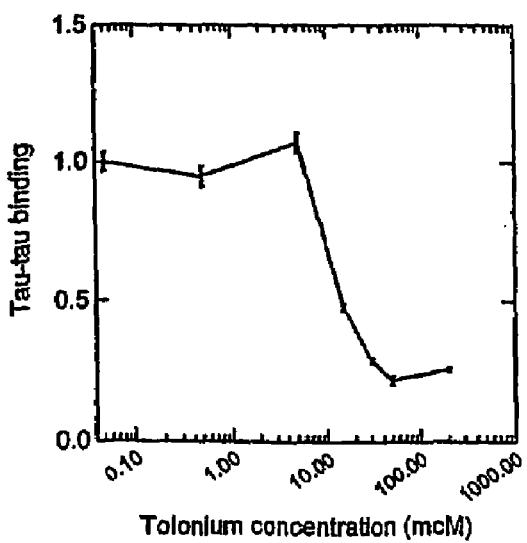

FIG. 37 shows tolonium chloride activity against tau-tau binding in Preparations 1 & 2.

Figure 38:
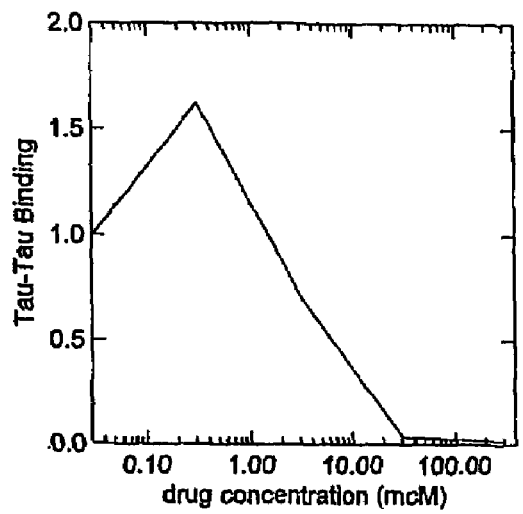
Figure 38:
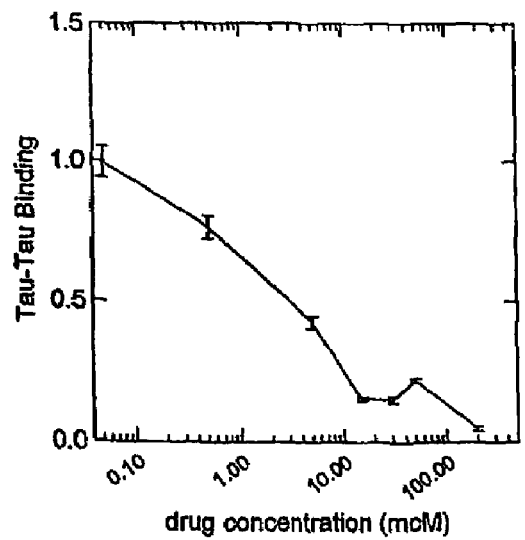

FIG. 38 shows DMMB activity against tau-tau binding in Preparations 1 & 2.

Figure 39A:
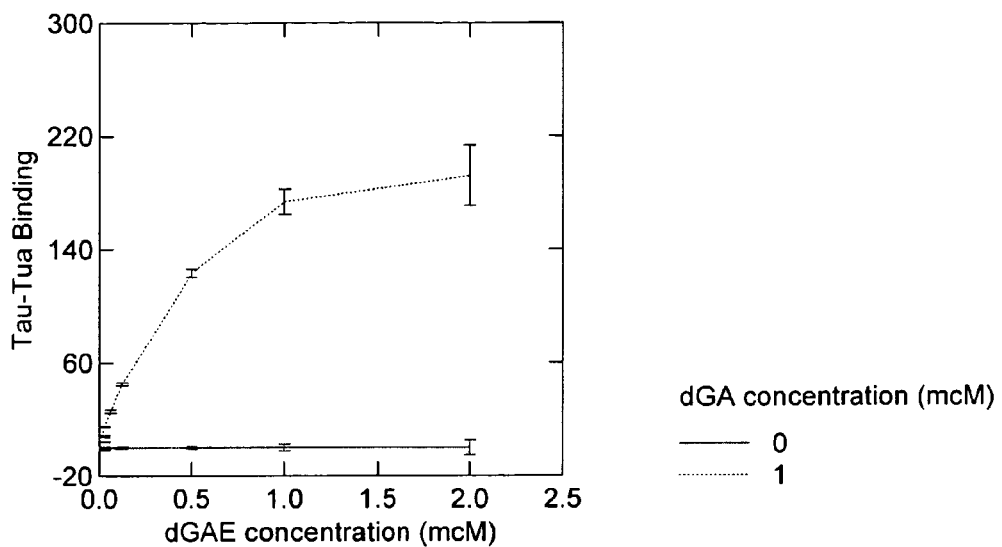
Figure 39B:
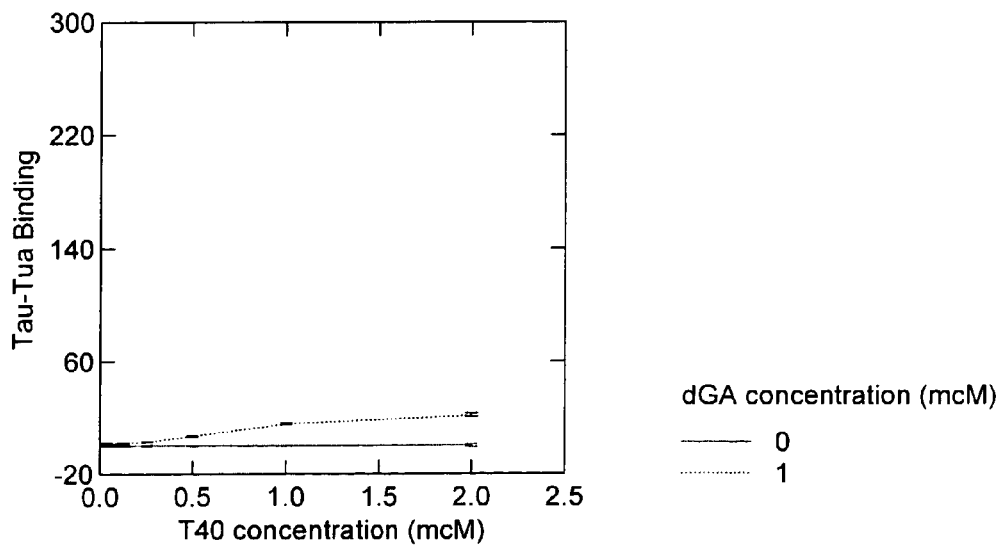
Figure 39C:
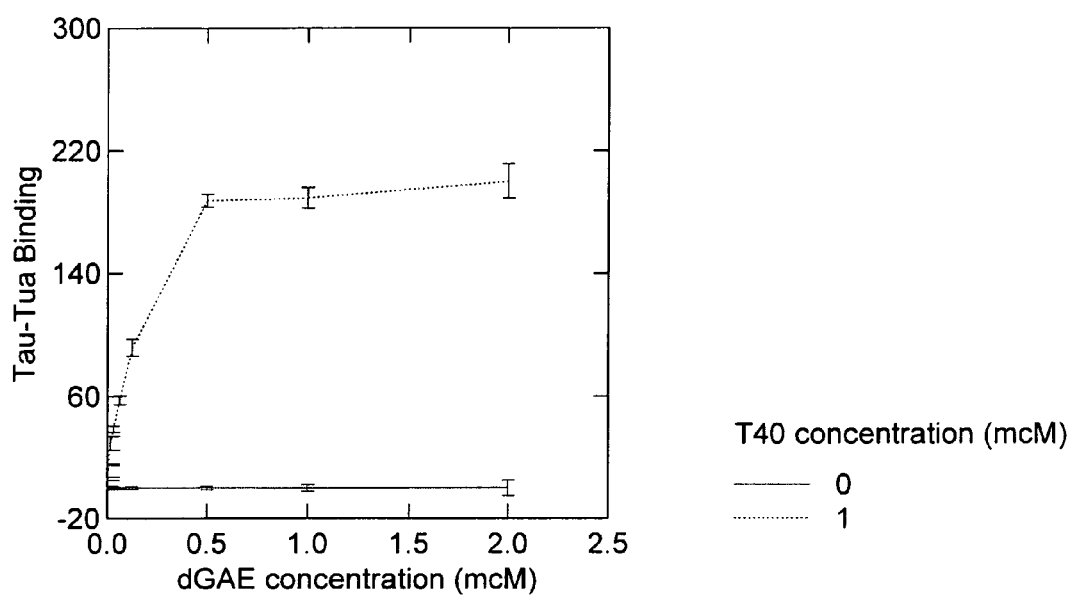

FIGS. 39a-c show that full-length tau protein (hT40) prepared according to the Preparation 2 protocol demonstrated minimal tau-tau binding activity when used in the aqueous-phase with dGA in the solid-phase (b). However, when hT40 was used in the solid-phase (c), binding of dGAE was similar to that obtained for binding of dGAE to dGA in the solid-phase (a).

Figure 40:
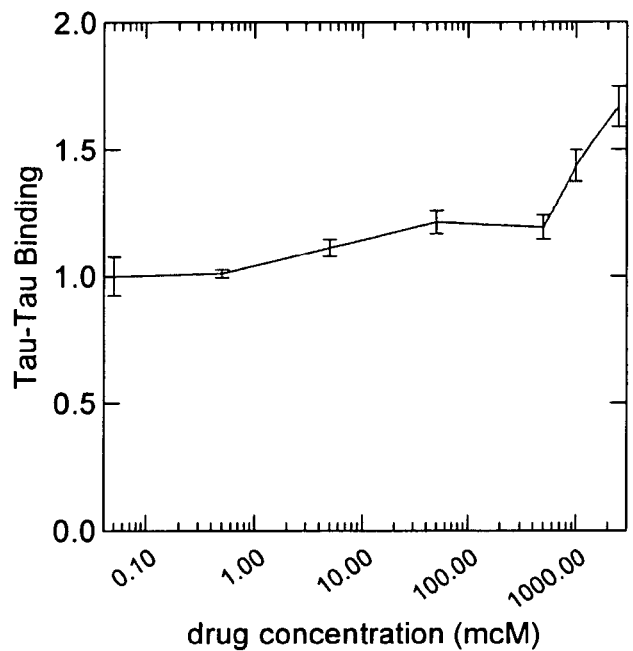
Figure 40:
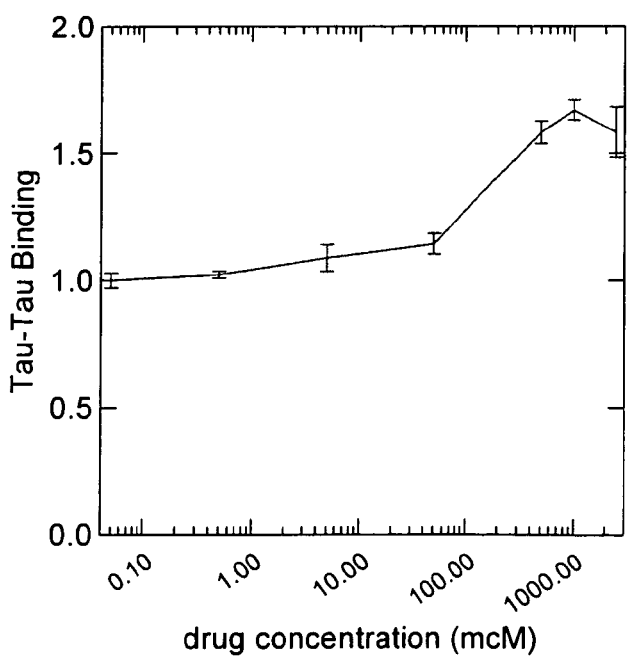
Figure 41A:
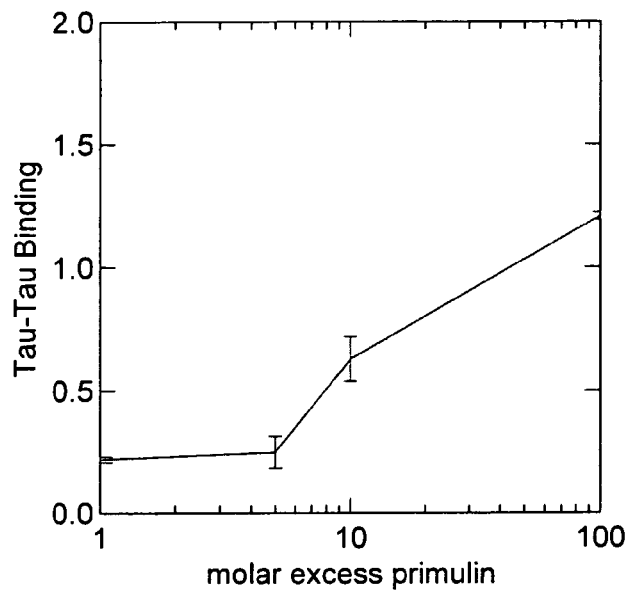
Figure 41B:
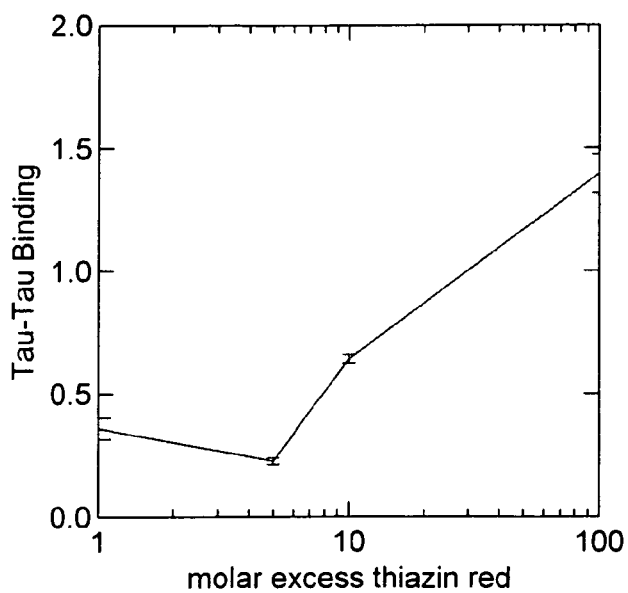
Figure 41C:
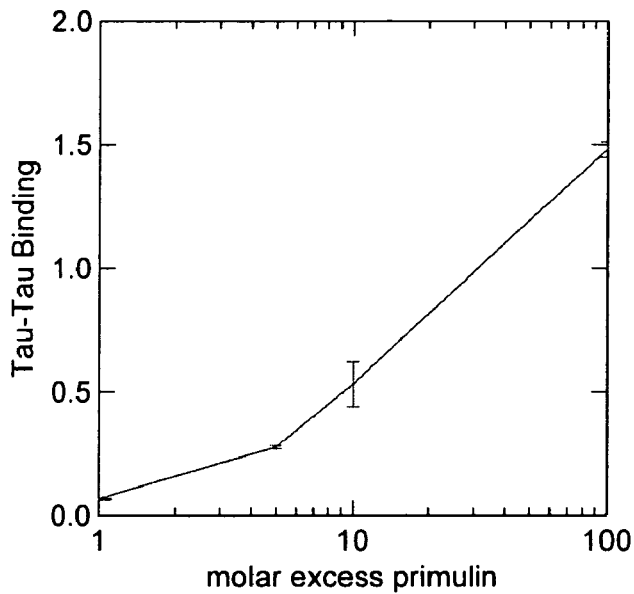
Figure 41D:
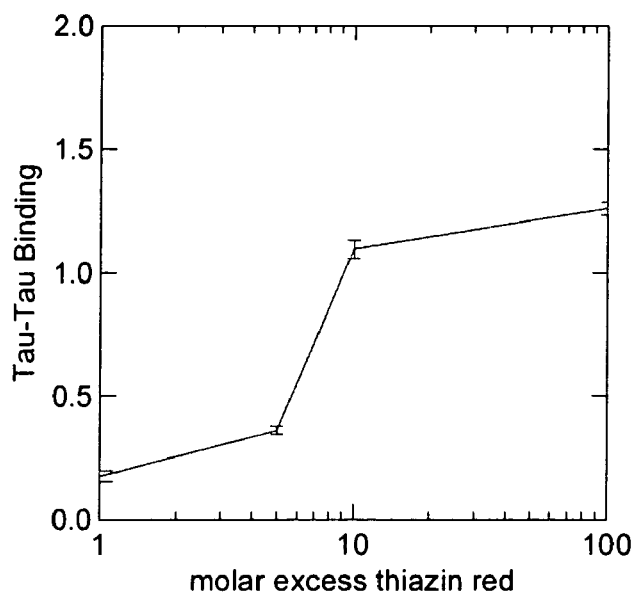

FIG. 40 shows primulin and thiazin red have no inhibitory activity against tau-tau binding in Preparation 2, and indeed enhance such binding at high concentrations.

FIG. 41 shows blocking of inhibitory effects of 5 µM DMMB on tau-tau binding in the presence of increasing concentrations of Primulin (a) and Thiazin Red (b), expressed as "molar excess" relative to DMMB. Similar results are shown for 15 µM DMMB in the presence of increasing concentrations of Primulin (c) and Thiazin Red (d).

Figure 42:
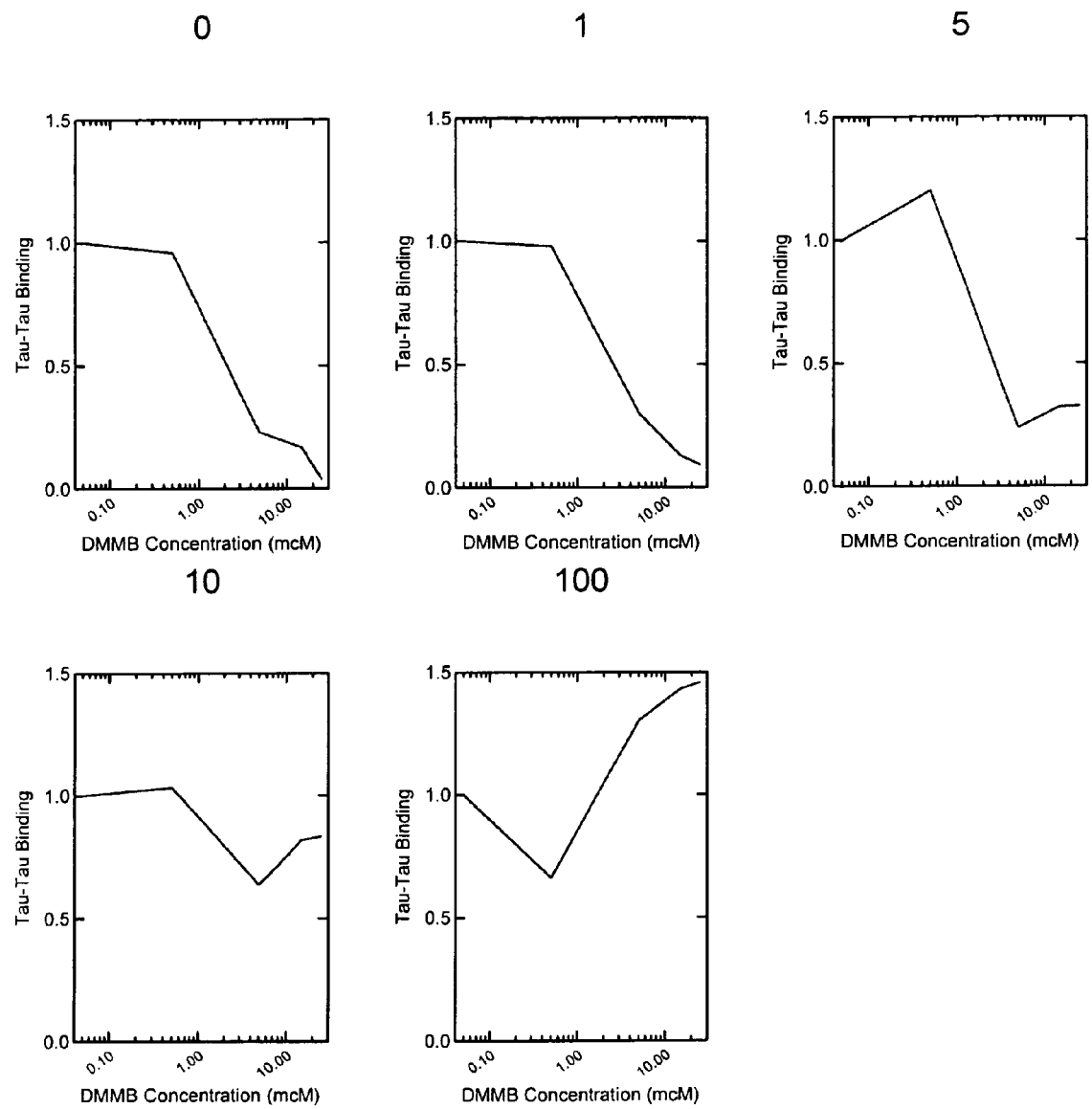

FIG. 42 shows attenuation and reversal of inhibition of Tau-Tau binding by DMMB in the presence of increasing molar excess of Primulin. For each graph, Tau-Tau binding is shown in the presence of constant concentrations of DMMB co-incubated with Primulin at 0×, 1×, 5×, 10×, 100× the DMMB concentrations shown. Inhibition of Tau-Tau binding produced by DMMB is progressively attenuated and reversed in the presence of increasing molar excess of Primulin.

Figure 43:
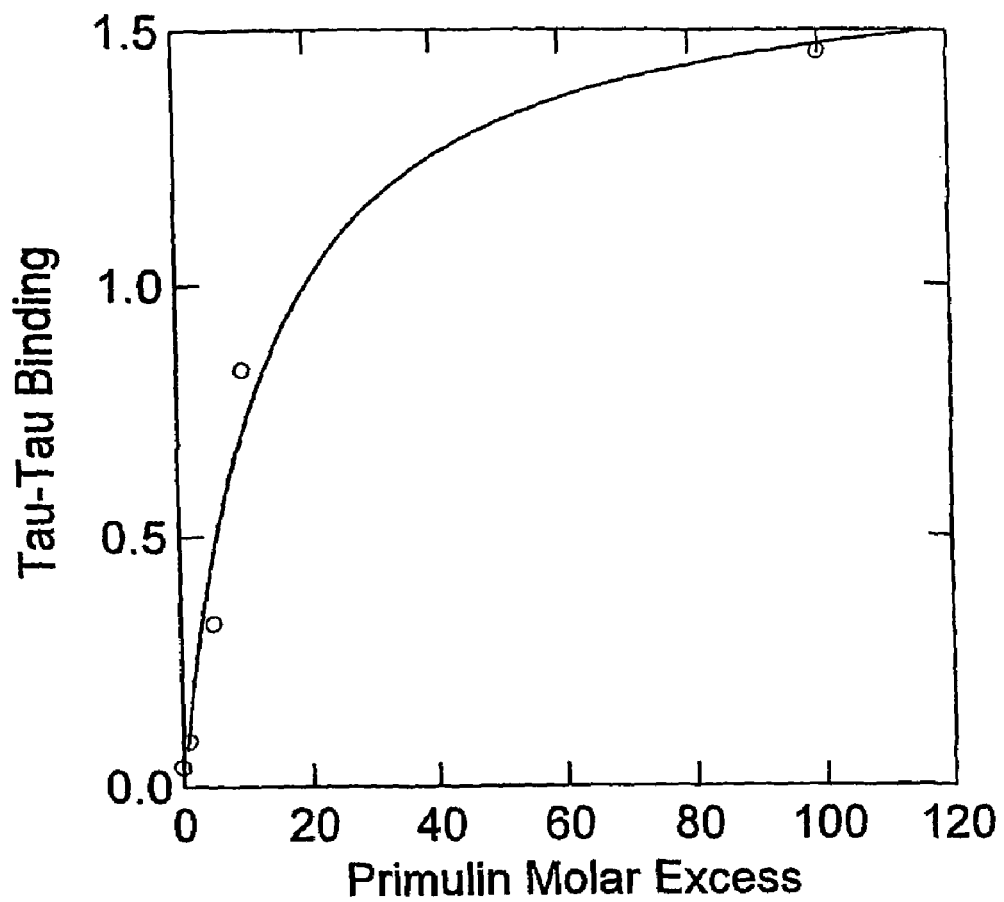

FIG. 43 shows a tau-Tau binding curve in the presence of 25 μM DMMB and increasing Primulin molar excess as shown. Tau-Tau binding can be modelled as follows:

$$\text{Binding}=(B\text{Max}\times[\text{Prim}])/(Kd+[\text{Prim}])$$

Where $B_{max}=1.67$
Kd=13.37
r=0.977 (observed vs predicted)

Figure 44:
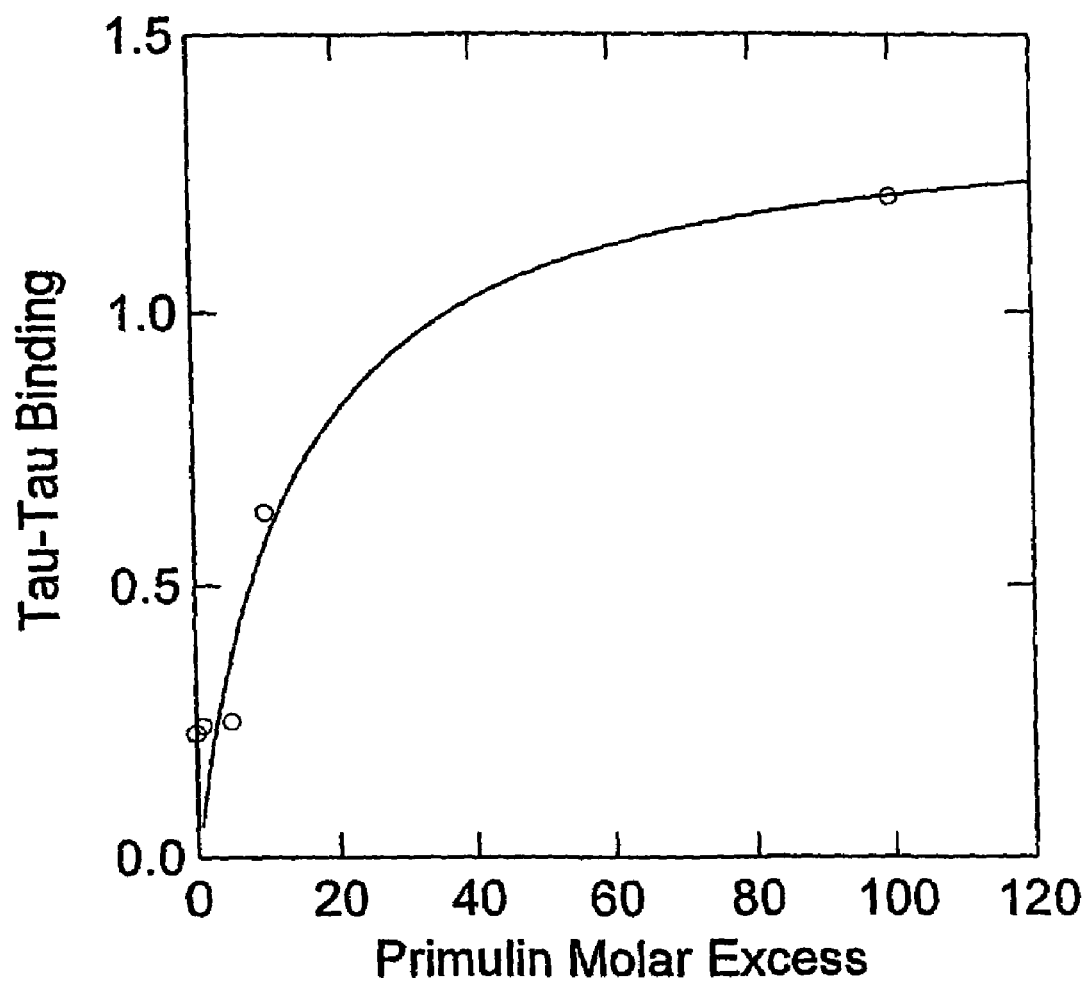

FIG. 44 shows a tau-Tau binding curve in the presence of 5 μM DMMB and increasing Primulin molar excess as shown. Tau-Tau binding can be modelled as follows:

$$\text{Binding}=(B\text{Max}\times[\text{Prim}])/(Kd+[\text{Prim}])$$

Where $B_{max}=1.38$
Kd=13.86
r=0.927 (observed vs predicted)

Figure 45:
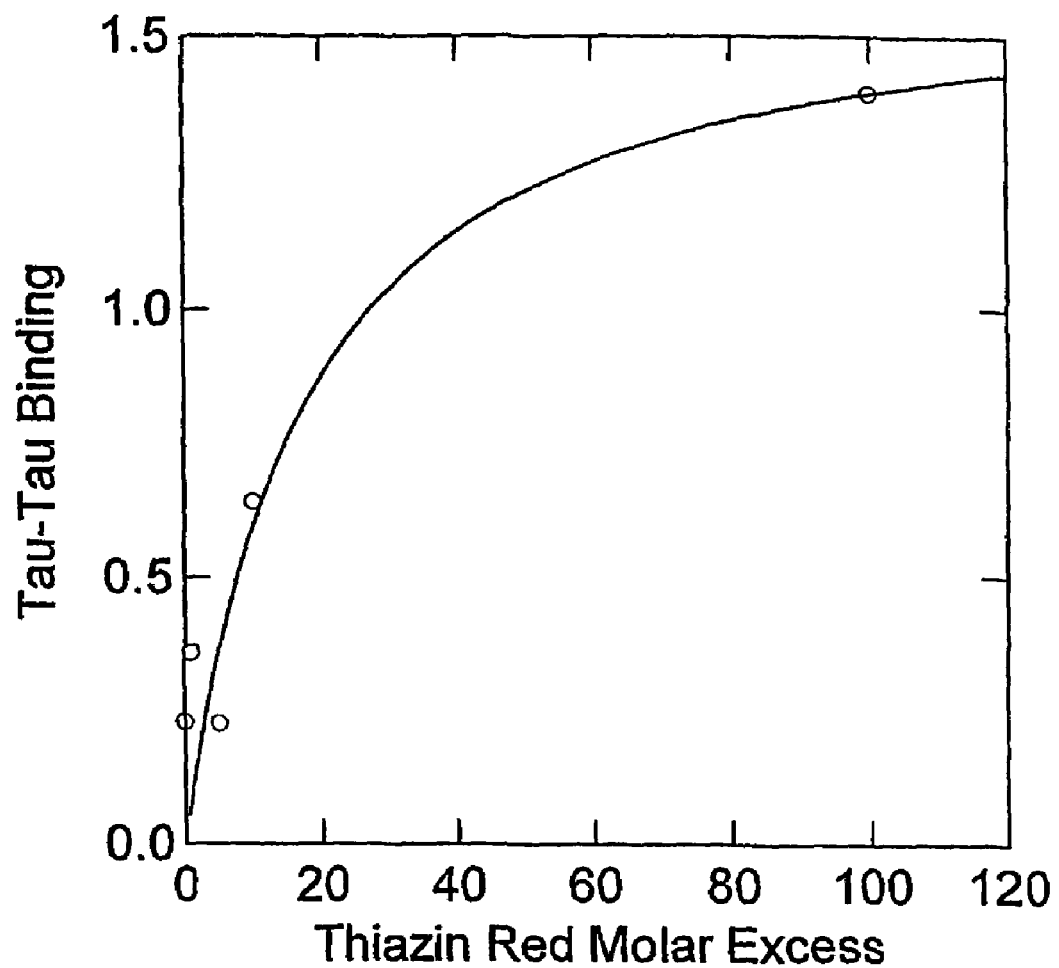

FIG. 45 shows a tau-Tau binding curve in the presence of 5 μM DMMB and increasing Thiazin Red molar excess as shown. Tau-Tau binding can be modelled as follows:

$$\text{Binding}=(B\text{Max}\times[TR])/(Kd+[TR])$$

Where $B_{max}=1.64$
Kd=17.45
r=0.915 (observed vs predicted)

EXAMPLES

Methods and Materials

PHF-binding Compounds

Compounds used herein were supplied by ICI Pharmaceuticals unless stated otherwise. Thioflavin-T and thiazine yellow were purchased from Fluka AG.

Quantitation of Fluorescence

Serial 16 μm sections are cut from the hippocampus of a case dying with clinically and neuropathologically confirmed AD. These sections were stained with thioflavin-S at concentrations 0.01%, 0.001% or 0.0001% in water for 5-10 min, then washed in water, and mounted in Apathe's aqueous medium. In a second series of experiments, sections were cut from the hippocampus and nucleus basalis of Meynert. These sections were stained with primulin at concentrations 0.1%, 0.01%, 0.001% and 0.00001% in water for 5-10 min, then washed in water, and mounted in Apathe's aqueous medium.

A Leitz fluorescence microscope fitted with a photo-multiplyer tube (Model MPV-2) was used to quantitate fluorescence emission. Three Leitz filter blocks were used as follows:
1. Filter block H2, code 513 417
   Excitation range Band pass 390-490 nm
   Mirror RKP 510 (i.e. transmit below 510 nm)
   Suppression filter LP 515 (i.e. reflect above 515 nm)
3. Filter block G, code 513 416
   Excitation range Band pass 350-460 nm
   Mirror RKP 510 (i.e. transmit below 510 nm)
   Suppression filter LP 515 (i.e. reflect above 515 nm)
4. Filter block A, code 513 410
   Excitation range UV band pass 340-380 nm
   Mirror RKP 400 (i.e. transmit below 400 nm)
   Suppression filter LP 430 (i.e. reflect above 430 nm)

Preparation of ifI and II

IfI material was prepared as described by Wischik et al (1985) J Cell Biol 100: 1905-1912.

IfII material was prepared as described by Wischik et al (1995) Neurobiol Aging 16: 409-431. For experiments involving non-pronase digested ifII an identical protocol was followed, omitting the pronase digestion step.

Spectrofluorimetry of IfII

These measurements were carried out in a Perkin-Elmer spectrofluorimeter (model MPF-3). A concentration of ligand of 0.00001% was routinely used for all measurements. Primulin was found to have an excitation peak at 370 nm and an emission peak at 515 nm. All measurements were therefore carried out at a standard excitation wavelength of 370 nm, and a constant slit width of 3 mm.

Competitive Binding Assay

IfI material was homogenised in a 0.2 ml glass homogeniser in PBS. To the suspension, test compounds were added to final concentrations ranging from 0.1% to 0.00001%. These were allowed to incubate for 5 min and primulin was added at equivalent or lower concentration. The suspensions were transferred to a glass slide, and examined by fluorescence microscopy across a range of fluorescence filter blocks, covering excitation and emission wavelengths between 380 nm and 570 nm. The end point sought in these observations was displacement of typical primulin fluorescence from tangle fragments.

Ligand Electronmicroscopy

PHFs derived from an ifI fraction were deposited on a carbon coated grid after pronase digestion, and incubated briefly with a preparation of biotinylated Primulin, and then incubated with an anti-biotin antibody that has been conjugated with colloidal gold by the method of Slot and Gueze (1981).

Succinylation and Chromatography of IfII

Washed ifII fractions were taken up in 8 M urea/50 mM borate (1 ml, pH 9) and sonicated, 1 ml succinic anhydride in acetone was added to a final concentration of 250 mM succinate in 4 ml, and the pH was maintained at 8.5 with sodium hydroxide. The solution was clarified by centrifugation and applied to a Sephacryl S200 column equilibrated bicarbonate. The column eluate was monitored at either 230 or 280 nm.

Because succinylated fractions could not be visualised by Coomassie staining or silver staining of gels, bands were detected by autoradiography after specific chemical labelling of ifII fractions with Bolton-Hunter reagent (Amersham).

For photoaffinity labelling of PHF derived peptides, ifI or ifII fractions were pre-incubated with an $I^{125}$-labelled photolabile derivative.

The photolabelled fraction running at a Kav of 0.21 was concentrated by ultrafiltration through an Amicon YM2 membrane (10 ml), digested with chymotrypsin (0.01 mg/ml) in 50 mM ammonium bicarbonate. Chymotryptic fragments for sequence analysis were isolated by Dr H. C. Thogersen by reverse phase HPLC using a C18 column, with a 0-100% acetyl nitrile gradient, with 0.1% trifluoroacetic acid. Chymotryptic peptides were sequenced.

Morphological Studies of PHFs in the Presence of Phenothiazines

For these experiments, ifII fractions were prepared as described above for electron microscopy. This material was either incubated directly with preparations of phenothiazines at final concentrations ranging between 0.1% and 0.0001% and then applied to carbon coated grids, and examined directly after LiPTA staining (1%). Alternatively, ifII suspensions were deposited on carbon coated grids, partially dried, and washed with solutions of phenothiazine. Such preparations were either stained directly with LiPTA or were processed further for immunoelectron microscopy using 6.423 as the primary antibody. Electron micrographs were recorded at nominal magnifications between 25,000 and 45,000.

Calculation of Aggregated Tau Protein in the Extracellular Space Expressed in µg/g of Brain Tissue as a Function of Braak Staging Previously reported PHF-tau levels in pmol/g (P) and tangle counts per mm$^2$ (T) in a clinically and neuropathologically staged cohort (R. Y. K. Lai, et al., *Neurobiol Aging* 16, 433 (1995)) were used to derive an estimate of PHF-tau level per affected pyramidal cell (PC) in pg/cell using the same ELISA in human brain. The tangle count per mm$^2$ provides an estimate of the number of affected pyramidal cells within a volume 1 mm×1 mm×0.1 mm (0.0001 cm$^3$), allowing that any tangle profile counted in a nominal 7 µm section could extend ~45 µm orthogonal to the section in either direction (S. M. Blinkov, I. I. Glezer, The human brain in figures and tables, a quantitative handbook; Plenum Press, NY, 1968, Table 204). The core PHF-tau level in pg/cm$^3$ is 10×P since the PHF-core tau fragment is 10 kD (C. M. Wischik, et al., *Proc. Natl. Acad. Sci. USA* 85, 4506 (1988)). From this, PC=(P×10)/(T/0.0001). At Braak stages 4-6 (H. Braak, E. Braak, *Acta Neuropathol.* 82, 239 (1991)), regional values for PC in grey matter were: frontal cortex, 0.13±0.05 pg/cell; hippocampus, 0.60±0.39 pg/cell; temporal cortex, 1.074±0.44; entorhinal cortex 1.56±0.63 pg/cell. These differences reflect anatomical differences, different regional rates of disease progression (C. Bancher, H. Braak, P. Fischer, K. Jellinger, *Neurosci. Lett.* 162, 179 (1993), also Gertz et al., *Acta Neuropathol.* 95, 154 (1988)), and the degree to which tangle counts underestimate PHFs accumulating in dystrophic neuritis at more advanced stages of pathology (Lai et al, 1995, loc cit). The overall means provide an approximation for the PHF-levels per cell which would be relevant to AD. These are 0.37±0.08 pg/cell for cases at Braak stages 1-3, and 1.08±0.28 pg/cell for cases at Braak stages 4-6.

For the purpose of estimating extracellular aggregated PHF tau, shown below in the Table, and in FIGS. 26, 27, 29 and 31, tangles were counted as extracellular if mAb 423 immunoreactivity could be demonstrated after treatment of glass-mounted sections with 98% formic acid for 5 minutes prior to incubation with mAb 423 for 1 hr. For the avoidance of doubt, this methodology differs from that reported in Mena et al. (1996) where free-floating vibrotome sections were incubated briefly with formic acid, and then overnight with mAb 423. As shown in that report, this latter overnight free-floating section protocol achieved maximal mAb 423 immunoreactivity in intracellular tangles, and showed that all intracellular tangles contain mAb 423 immunoreactivity, albeit in a state substantially occluded by the fuzzy outer coat of the PHF (see FIG. 3). The purpose of the present protocol was to ensure maximum labelling of the Stage 3 and Stage 2 tangles illustrated in FIG. 3. Some minor degree of labelling of intracellular tangles could not be entirely excluded, and counting attempts have also been made where a subjective discrimination has been attempted. However, the latter estimates do not agree with density or probability of labelling of tangles by mAb AT8 (FIGS. 28, 30, 32), which is solely intracellular, and shows completely different profiles with respect neuropathological stage from those revealed using mAb 423. For the purposes of the present calculations, therefore, counts of mAb 423-immunoreactive tangles were taken as substantially or entirely representative of extracellular tangle pathology at Stages 2 and 3 as shown in FIG. 3, but substantially not Stage 1 of FIG. 3. For the avoidance of doubt, the Stages referred to in FIG. 3 are not Braak stages, but stages of degeneration of a single neurone containing a tangle.

The specific data shown in Table 1 was based on the following:

| Number | BST | ME1T4 | PC | PT4 | REG3B | SE1T4 |
|---|---|---|---|---|---|---|
| 1 | 1.0000 | 0.3982 | 1.5600 | 0.6212 | 1.0000 | 0.3982 |
| 2 | 2.0000 | 6.7259 | 1.5600 | 10.4924 | 1.0000 | 2.7047 |
| 3 | 3.0000 | 14.9646 | 1.5600 | 23.3448 | 1.0000 | 2.9836 |
| 4 | 4.0000 | 33.6297 | 1.5600 | 52.4624 | 1.0000 | 10.9883 |
| 5 | 5.0000 | 44.3102 | 1.5600 | 69.1240 | 1.0000 | 13.0298 |
| 6 | 1.0000 | 0.0 | 0.6000 | 0.0 | 2.0000 | 0.0 |
| 7 | 2.0000 | 1.3865 | 0.6000 | 0.8319 | 2.0000 | 0.4531 |
| 8 | 3.0000 | 3.7169 | 0.6000 | 2.2302 | 2.0000 | 0.8060 |
| 9 | 4.0000 | 8.9384 | 0.6000 | 5.3630 | 2.0000 | 3.0048 |
| 10 | 5.0000 | 23.9479 | 0.6000 | 14.3687 | 2.0000 | 4.0567 |
| 11 | 1.0000 | 0.0 | 0.6000 | 0.0 | 3.0000 | 0.0 |
| 12 | 2.0000 | 0.0 | 0.6000 | 0.0 | 3.0000 | 0.0 |
| 13 | 3.0000 | 0.0 | 0.6000 | 0.0 | 3.0000 | 0.0 |
| 14 | 4.0000 | 0.1293 | 0.6000 | 0.0776 | 3.0000 | 0.1293 |
| 15 | 5.0000 | 2.2007 | 0.6000 | 1.3204 | 3.0000 | 1.0634 | wherein:
BST is Braak Stage
ME1T4 is the extracellular tangle count
PC is an estimate of the PHF-tau concentration per cell (calculated as above)
PT4 is the PHF content ascribed to extracellular tangles (PC× MEIT4)
REG3B is the grouping of brain regions into 3 groups as per FIGS. 26 and 27 of the SE1T4 is the standard error of the extracellular tangle count Example 1

Aggregated Tau in Braak Staging

Based on immunochemical properties (Refs 26, 27, 30), it is possible to distinguish intracellular tangles from extracellular tangles. Both frequency of cases with tangles in these categories (ie probability) and their quantity (ie counts per mm$^2$) were determined in a prospective case series and grouped into the regions known to represent stages in the progression of pathology according to the system of Braak and Braak As shown in FIG. 25, stages 2-4 can be clearly distinguished from stage 1 on the basis of probability of extracellular tangles in E2/Trans and E4/HC. Also shown are the figures for F/T/P regions (neocortical regions—frontal, temporal, parietal).

Conversely, intracellular tangles provide a poor basis for discrimination of early stages in these regions, but a good basis for discriminating stages 4 and 5 using neocortical regions. Similarly, when cases with MMSE scores greater than 21 in the 12 months prior to death were selected, similar results were obtained. Again, similar results were obtained when tangle densities were determined.

These results can be converted into approximations for the quantity of aggregated tau protein in the extracellular space expressed in µg/g of brain tissue as described in Materials and Methods above. The results are shown in Table 1. These are underestimates, as the tangle counts underestimate the quantity of aggregated tau protein.

TABLE 1

ESTIMATE PHF-TAU CONTENT IN ECT'S BY REGION AND STAGE

| REGION   | BST | PHF/TAU (µg/g) |
|----------|-----|----------------|
| E2/TRANS | 1   | 0.62           |
|          | 2   | 10.49          |
|          | 3   | 23.34          |
|          | 4   | 52.46          |
|          | 5   | 69.12          |
| HC/E4    | 1   | 0              |
|          | 2   | 0.83           |
|          | 3   | 2.23           |
|          | 4   | 5.36           |
|          | 5   | 14.36          |
| F/T/P    | 1   | 0              |
|          | 2   | 0              |
|          | 3   | 0              |
|          | 4   | 0.08           |
|          | 5   | 1.32           |

Table 1 shows quantity of aggregated tau protein in the extracellular space expressed in µg/g of brain tissue as a function of Braak staging. The data was calculated as described in the materials and methods.

In summary, these results demonstrate that extracellular deposits of PHF-tau in medial temporal lobe structures provide a basis for empirical staging of the neurofibrillary degeneration of AD. Such staging could only be accomplished by radio-imaging methods provided suitable ligands could be created.

Example 2

Assessment of Compounds Binding within the Aggregated Repeat Domain of PHF-core Tau Protein A prototype compound was obtained as one component of the crude, commercially-available preparation of thioflavin-S was separated into ~20 distinct constituents by analytical thin-layer chromatography, and preparative chromatography. Tests showed that not all of the constituents were able to act as effective tangle ligands. Specifically, pure primulin (FIG. 5, compound 1a) was found to label tangles, but the benzothiazole thioflavin-T (FIG. 5, compound 1b) was much less effective, although it labelled amyloid preferentially.

Furthermore, compound 1a was found to displace compound 1b at tangles when the latter was introduced at 10-fold excess into crude tangle extracts.

A possible difference was postulated to be the sulphonate group at position 1 (FIG. 5, compound 2 [2-(4-amino phenyl)-6-methyl-1-sulphonate benzothiazole]). However, primulin (compound 1a) was found to displace this from tangles (though not amyloid). Therefore, tangle labelling is not due solely to the sulphonated benzothiazole structure, indicating that a longer aromatic structure is required.

Purified thiazin red (FIG. 5, compound 3a) was found to compete with primulin at equivalent concentrations, whereas the compound 3b (thiazin yellow, FIG. 5) did not. Therefore, an extended aromatic benzothiazole structure does not, per se, determine high binding affinity within tangles.

In order to define a minimum critical requirement for competitive binding, the sulphonated benzothiazole was extended by addition of a single phenyl group across a diamino-linkage. This compound (FIG. 4, compound 4a), although not fluorescent, was found to compete out thiazin red and primulin fluorescence at equivalent concentrations. Compound 4a therefore defines the minimum critical structure required for high affinity binding within the tangle.

In order to prove that the binding site within the tangle was in fact the PHF itself, compound 4a was further extended with addition of a biotin group (FIG. 4, compound 4b). Since this was still found to compete primulin and thiazin red, compound 4b preserved high affinity binding within the tangle. Furthermore, immunogold-conjugated anti-biotin antibody was found to label isolated PHFs pre-incubated with compound 4b, whereas no labelling was demonstrated without pre-incubation or pre-incubation with biotin alone (FIG. 31b). Finally, when a photo-activated conjugate of the compound was prepared, it was possible to identify and sequence the labelled protein. This was found to be the same core tau fragment as that isolated from the core of the PHF, which comprises the repeat region of the tau protein.

In summary, these results demonstrate unequivocally that the binding site for compounds 4a and 4b is within the aggregated repeat domain of the tau protein of the PHF-core. Furthermore, they demonstrate that compound 4a can be used as a chelate for addition of functional groups without disturbing ligand activity within the PHF core. Therefore, compound 4a could be used as chelate for addition of technetium or other imaging moiety to generate a ligand suitable for detecting e.g. extracellular tangles in AD.

Example 3

Determination of Optimum Dimensions of Ligand Molecules

FIG. 14 shows three of the structures described above, along with their dimensions as indicated. For example, the C11-C1 distance and C10-C1 distance are shown for primulin, a benzothiazole analogue (denoted 'analog'), and 'thiazin yellow'.

FIGS. 15 and 16 illustrate the crystal structures of the 'B' part of the primulin structure (Soon-Beng Teo et al., 1995, Acta Crystallogr., Sect. C, 591. As can be seen from FIG. 16, which is a 'side-on' view, the molecule is essentially flat, although it has a slight twist. The 'A' part of primulin can be computed from the same molecule. From this, one can derive measures of A+B, which provide an indication of the actual length of one of the active species of the present invention.

To compute the size of the "analog" shown in FIG. 14, measurement A was used from the data of FIG. 15, and measurement B was determined from a molecule denoted N2A and shown in FIGS. 17 and 18 (Gilardi, R. D., 1972, Acta Chrystallogr., Sect. B, 107). As can be seen from the side-on view in FIG. 18, this part of the molecule is completely flat. The same measurements apply to thiazin red, which is identical in its dimensions to the "analog".

The size of thiazin yellow (shown in FIG. 14) was determined as follows. The 'A' part comes from the molecule of FIG. 15 which was used for primulin, while the 'B' part comes from the molecule shown in FIGS. 19 and 20 (Gladkova et al., 1972, Kristallografiya 41). Again, part B of the molecule is completely flat, and the only difference with respect to the molecule shown in FIG. 17 is the distance between the aromatic groups.

FIGS. 21 and 22 illustrate how the molecule of FIG. 15 crystallises in space. As can be seen, the molecule forms an alternating 'herring-bone' pattern, and does not stack. In comparison, the crystal structure of methylene blue indicates that the molecules form stacks with alternating sheets of water molecules between the pi-bonded stacks.

Table 2 tabulates the minimum, maximum and mean dimensions for primulin ("PRIM"), the analog ("ANAL"), thinazin yellow, and the benzothiazole unit alone (i.e. structures 1b and 2 as shown in FIG. 5). The corresponding methylene blue dimensions are given as 'MBCC' (carbon to carbon) and 'MBNN' (nitrogen to nitrogen):

|  | 1 PRIM | 2 ANAL | 3 THIAZY | 4 BENZTHIA | 5 MBCC | 6 MBNN |
|---|---|---|---|---|---|---|
| Minimum | 14.7830 | 15.0500 | 15.7270 | 8.7700 | 7.0849 | 9.9600 |
| Maximum | 15.1120 | 15.2610 | 16.1380 | 8.9550 | 7.4443 | 9.9600 |
| Mean | 14.9475 | 15.1680 | 15.9273 | 8.8625 | 7.3031 | 9.9600 |

FIG. 23 shows a comparison of the mean, maximum and minimum extents of molecules which are active ligands (primulin and "analog"), and thiazin yellow (which is inactive as a ligand). The dimensions are given in angstrom units (AU). In FIG. 24, a similar comparison is made for the basic benzothiazole nucleus (i.e. molecules 1b and 2 of FIG. 5) and the diaminophenothiazines. These distances are carbon-to-carbon distances.

The above results illustrate that the molecules provided herein are substantially flat. There is, however, a fundamental difference in activity between ligands according to the present invention and other molecules discussed above. As is shown in the Figures, suitable ligands according to the invention comprise long, flat molecules with dimensions between 14.783 and 15.261 AU. On the other hand, a longer molecule, such as thiazin yellow, which exceeds these dimensions (mean 15.927 AU) does not serve as an effective ligand, even though it is flat. However, certain shorter, flat, molecules bind preferentially to amyloid.

Example 4

PET Using Ligand Molecules and Inhibitors

FIGS. 11 to 13 indicate typical synthesis methods which could be used to convert either the diaminophenothiazines or the "analog" into positron emitting species.

FIG. 11b in particular shows a method whereby thionin is treated with NaH followed by labelled methyl iodide to give methylene blue. A similar procedure can be adopted for the synthesis of methylene blue starting from Azure A and Azure B. Other strong bases may also be used.

Other methods that may be used include HCl and labelled MeOH; labelled trimethyl phosphoric acid; labelled dimethylsulphoxide and Labelled formaldehyde. The chemistry of the syntheses and general methodology are all familiar to persons skilled in the art. These examples are given without any implied restriction as to ultimate methodology.

Example 5

Blocking Ligands

Compounds such as thioflavin-T and -S strongly stain amyloid deposits. However FIG. 31 demonstrates that such compounds can be displaced from tangles by primulin. Therefore these compounds may be used as blocking reagents to saturate binding sites which are not of interest without inhibiting the binding of ligands to aggregated tau.

Example 6

Comparison of Ligand Molecules and Inhibitors

There appears to be a fundamental difference in activity of the molecules which are effective ligands, compared with those which are effective inhibitors of tau-tau binding. The benzothiazole molecule does not disrupt PHFs, nor indeed do any of the ligands, whereas the diaminophenothiazine series constitute PHF-disrupters and tau aggregation inhibitors.

Further investigations into the relationship between aggregation-dependent tau ligands and tau aggregation inhibitors were carried out using primulin. Primulin in solution has a fluorescence peak at 520 nm. This shifts to 470 nm when primulin is bound within a pure preparation of PHFs (FIG. 6). Treatment of PHFs with citraconic anhydride, which has been shown to disrupt the structure of the PHF and liberate free tau (as well as reversing the charge on lysines), was found abolish the 470 nm fluorescence peak (FIG. 7). Therefore, binding by such compounds is dependent on the polymerised state of tau found in the PHF, but is not present in free tau.

Compounds have been identified which disrupt the structure of the PHF and reverse the proteolytic stability of the PHF core (see WO 96/30766). Examples of such compounds are shown in accompanying FIG. 8. The present inventors have now identified that these compounds bind to tau at a specific binding site within the high affinity tau-tau binding domain. However, it is found that such compounds may not disrupt the binding of primulin to tau in aggregated tau molecules, as shown by the retention of the fluorescence peak of primulin at 470 nm in the presence of alcian blue (FIG. 9).

Thus it appears that although alcian blue can inhibit tau-tau interactions, either the site of the inhibition, or perhaps the order of binding interaction at which it acts, are such as to leave binding site for SB-ligands extant. Thus compounds which act as ligands of aggregated tau do not appear to bind at the same site(s) as compounds which are tau-aggregation inhibitors, although they may still affect the inhibitory properties of those inhibitors (see Example 7 below).

This point was further examined by studying the potency of typical aggregated tau ligands as tau-aggregation inhibitors. It has been shown previously that tau aggregation inhibitors (e.g. diaminophenothiazines) can be identified on the basis of inhibition of tau-tau binding in a solid-phase assay (WO 96/30766). When tested in the same assay, primulin and thiazin red were found to be weak inhibitors of tau-tau binding (FIG. 10). Thus, although these compounds are potent ligands for tau within the PHF-core, they are at most weak inhibitors at the site required for inhibition of tau-tau binding.

Demonstration that compounds of the diaminophenothiazine-like class bind tau in the aggregated state is provided by the direct demonstration of disruption of PHF structure in the presence of sufficiently high concentrations, particularly of compounds such as methylene blue. Thus, compounds of the diaminophenothiazine-like class which are inhibitors of tau-tau binding can serve as aggregated-tau ligands at lower concentrations.

In summary, the inventors have found that it is possible to define two classes of binding site within the core-PHF tau aggregate. Both are potentially useful for the development of radiological imaging ligands:
(i) Sulphonated benzothiazole-like sites: compounds of this type, associated with suitable chelates such as technetium, may serve as ligands for extracellular tangles, due to their size and charge.
(ii) Diaminophenothiazine-like sites: such compounds, when suitably labelled with a positron-emitting functional group, would serve as ligands for all tau aggregates, and would be capable of crossing the blood-brain-barrier (Ref 36) and entering cells. Thus these compounds, and derivatives thereof, have potential use in the labelling of intracellular tangles, e.g. those present in the brains of AD patients, or intracellular tangles when used at lower concentration.

Example 7

Example Assays for Identifying Further Diagnostic Ligands Based on Relief of Inhibition (i) Preparation of Tau Protein in which Partial Aggregation has Occurred.

The preparation ("Preparation 2") is shown schematically in FIG. 32, and differs from earlier described methods (e.g. in WO96/30766—"Preparation 1"—shown in (ii) below).

The recombinant cDNA plasmids are those described in WO96/30766 the disclosure of which is herein incorporated by reference.

Briefly, tau cDNA was generated using standard protocols (Sambrook, Fritsch & Maniatis "Molecular cloning. A Laboratory Manual" (1989) Cold Spring Harbor Laboratory, N.Y.) from mRNA isolated from brain tissue of an Alzheimer patient whose tissue was obtained 3 h after death. The cDNA library was screened with synthetic 17-mer oligonucleotide probes derived from the sequence from part of a PHF core protein (Goedert et al. (1988) Proc. Natl. Acad. Sci. USA, 85, 4051-4055). Full length cDNA clones were subcloned into the EcoRI site of M13 mp19 and site-directed mutagenesis used to introduce a NdeI site in the context of the initiator codon. Following cleavage with NdeI and EcoRI, the resulting cDNA fragments were subcloned downstream of the T7 RNA polymerase promotor into NdeI/EcoRI-cut expression plasmid pRK172 (McLeod et al. (1987) EMBO J., 6, 729-736). PRK172 is a derivative of pBR322 that is propagated at very high copy number in *E. coli* due to removal of the pBR322 copy number control region. The plasmid carries an ampicillin resistance gene for selection of recombinant clones.

cDNA constructs coding for truncated forms of tau were prepared from mRNA as described in Novak et al. (1993) EMBO J., 12, 365-370. The mRNA was used as a template for polymerase chain reaction (PCR) using specific oligonucleotide primers. The sense primer contained an NdeI site and the anti-sense, an EcoRI site. PCR fragments were subcloned into pRK172 as described above. The primers used for construction of dGAE are given in FIG. 22. The authenticity of all DNA fragments used for expression was confirmed by full length sequencing of both strands.

Details for the construction of htau40 ("T40") cDNA are described in (Goedert et al. (1989), Neuron 3: 519-526). This sequence is the largest form of tau found in the CNS and encodes tau protein that contains both the 2 N-terminal inserts of 29 amino acids each and an extra 31 amino acid repeat in the tubulin-binding domain. The DNA sequence and its predicted amino acid sequence are shown in FIG. 21 (SEQ ID NO: 4).

Recombinant plasmids were used to transform *E. coli* BL21 (DE3) a strain used for prokaryotic expression which carries a chromosomal copy of the bacteriophage T7 RNA polymerase gene under control of the lac UV5 promotor (Studier and Moffat (1986), J. Mol. Biol. 189, 113-130). Exponentially growing cultures were induced with IPTG (iso-propyl thiogalactodise) for 3 h.

Large-scale purification (1 liter bacterial culture) of tau fragments was carried out as described by Goedert and Jakes (1990, EMBO J., 9, 4225-4230), with minor modifications. Cells were disrupted by rapid freezing of the cell pellet in liquid nitrogen. The pellets were then suspended in buffer containing 50 mM PIPES, 1 mM dithiothreitol (DTT) (pH 6.8). The thermostable proteins in the supernatant were dialysed against PIPES/DTT, then applied to a column containing phosphocellulose equilibrated in the same buffer. Tau protein was eluted with a gradient of NaCl (0-0.5M) in the above buffer. Fractions were analysed by SDS-PAGE and both Coomassie staining and immunoblotting. Those fractions containing tau were pooled, dialysed against 25 mM MES, 1 mM DTT (pH 6.25) and stored at −20° C. at approximately 5 mg/ml. Protein concentrations were measured by the Lowry method (Harrington C R (1990), "Lowry protein assay containing sodium dodecyl sulphate in microtitre plates for protein determinations on fractions from brain tissue", Analytical Biochemistry 186: 285-287).

Preparation 2 differs from Preparation 1 above in the following respects: (1) The concentration of cells at the sonication stage is increased by 5-fold. (2) A batchwise adsorption of non-tau proteins to DE52 is included. (3) The proteins are not subjected to heat treatment. (4) The final step involves concentration using polyethylene glycol.

*Escherichia coli* is grown in 2×TY medium (Oxoid) supplemented with ampicillin (50 micrograms per ml) to late-logarithmic phase. Cells from 5 liters of culture are harvested by centrifugation and the cell pellets frozen rapidly over liquid nitrogen. The pellets are taken up with 50 mM PIPES (pH 6.8) containing 1 mM EDTA, 1 mM dithiothreitol and 1 mM phenylmethylsulphonylfluoride (PMSF) and bacteria lysed by sonication (2×3 min) at 4C. The mixture is centrifuged at 10,000 rpm for 20 min. The supernatant is rotated with 1 gram of Whatman DE52 for 3 hr at 4C. The mixture is separated on a column and the flow-through material that fails to bind to DE52 is incubated for 3 hr at 4C, with rotation, with 0.4 g of Whatman P11 (freshly regenerated according to manufacturer's recommendations). The column is washed with column buffer (50 mM PIPES, pH 6.8 containing 1 mM EGTA, 5 mM EDTA, 0.2 mM MgCl₂, 5 mM β-mercaptoethanol and 1 mM PMSF). Tau protein is eluted stepwise with a 0.1 to 1 M gradient of KCl in column buffer. Fractions containing tau (determined by immunoassay) are pooled and dialysed against 80 mM PIPES (pH6.8) containing 1 mM EGTA, 1 mM MgCl₂ and 5 mM β-mercaptoethanol, using dialysis tubing with a molecular weight cut-off of 1,000. The dialysate is concentrated by applying polyethylene glycol 8000 to the outside of the sac for 2-3 hr. The final concentration of tau ranged from 3 to 10 mg per ml.

In a typical large scale preparative run, the specific immunoreactivity of tau is purified approximately 30- to 40-fold from the material that fails to bind to DE52. Approximately 60% of the tau is recovered in the final product with 10% failing to bind to P11 and the remainder in fractions ignored from the column.

Table 3 shows details of a preparative run for dGA. "Purification-fold" is expressed as the ratio of specific immunoreactivity for each fraction (ie immunoreactivity/protein concertration) to specific immunoreactivity in DE flow-through.

|  |  | Vol (ml) | mg/ml | AU/ml | AU | AU/mg | Purif'n (-fold) | Recovery (% AU) |
|---|---|---|---|---|---|---|---|---|
| Total cells |  | 200 | 26 | 40000 | 8000000 | 1538 |  |  |
| DE flow thro' |  | 240 | 20 | 40000 | 9600000 | 2000 | 1.00 | 100% |
|  |  |  |  |  |  |  |  | 11% in P11 flow thro' |
| P11 flow thro' |  | 220 | 19 | 5000 | 1100000 | 263 |  |  |
| Fractions | #1 |  | 1.48 | 5000 | 3000 | 3388 | 2 |  |
| (6 ml each) | #2 |  | 0.98 | 20000 | 120000 | 20492 | 10 |  |
|  | #3 |  | 1.60 | 8000 | 480000 | 50000 | 25 |  |
|  | #4 |  | 2.69 | 200000 | 1200000 | 74294 | 37 |  |
|  | #5 |  | 3.09 | 200000 | 1200000 | 64767 | 32 |  |
|  | #6 |  | 3.31 | 200000 | 1200000 | 60459 | 30 | 62% in pooled fractions |
|  | #7 |  | 2.71 | 200000 | 1200000 | 73746 | 37 |  |
|  | #8 |  | 2.70 | 125000 | 750000 | 46296 | 23 |  |
|  | #9 |  | 2.20 | 100000 | 600000 | 45537 | 23 | 20% in discarded fractions |
|  | #10 |  | 1.83 | 80000 | 480000 | 43764 | 22 |  |
| Pure dGA |  | 14.5 | 8.4 | 600000 | 8700000 | 71429 | 36 |  |

FIG. 33 is a graphical plot of the data from Table 3.

Table 4 summarises yields from typical preparative runs for the tau protein species: dGA, dGAE and hT40.

| Tau preparation | Protein concentration (mg/ml) based on: | | Immunoreactivity (mAb 7/51; AU/ml) | Protein yield (per 10 litres) |
|---|---|---|---|---|
|  | abs at 280 nm | Protein assay (BSA ref) |  |  |
| dGAE (711) | 3.3 | 3.8 | 300,000 | 100 mg |
| dGA (1511) | 8.1 | 8.4 | 600,000 | 122 mg |
| T40 (1311) | 3.5 | 3.1 | 125,000 | 120 mg |
|  | based on extinction coefficients | | abs at 280 nm | |
| BSA (reference) |  | 10 mg/ml | 6.6 | |
| Tau protein |  | 10 mg/ml | 14.7 | |

Proteins were separated by running down a 50×1 cm sepharose CL-6B gel filtration column equilibrated with PBS buffer and run at room temperature. A molecular weight standard curve was prepared for the column by running molecular weight markers over the range 12,400 to 200,000 down the column. A standard curve was prepared by plotting the $\log_{10}$ of the Mr in Kd against Ve/Vo for each protein standard, where Ve is the elution volume for the standard and Vo is the void volume for the column determined with blue dextran.

T40 or dGAE were loaded in 0.5 ml buffer containing 5% glycerol and collected in 1 ml fractions. Presence of protein in the fractions was determined spectrophotometrically by the absorbance at 280 nm. Presence of dGAE or T40 was detected by ELISA with monoclonal antibody 7/51 or 499 respectively. ELISA assay was carried out in 96 well PVC plates as follows:

50 µl samples of each fraction incubate 1 hr at 37 C, wash plate in 0.05% tween-20 and then block binding sites with 200 µl PBS+2% non fat milk powder for 1 hr at 37 C. Wash plate in 0.05% tween-20, incubate with 50 µl primary antibody diluted 1:10 in PBS+2% non fat milk powder for 1 hr at 37 C. Wash plate in 0.05% tween-20, incubate with 50 µl secondary antibody (goat anti-mouse IgG:HRP conjugate) diluted in PBS+2% non fat milk powder for 1 hr at 37C. Wash plate in 0.05% tween-20 then rinse in deionised water, add 50 µl freshly prepared substrate (TMB [tetramethylbenzidine] in sodium acetate buffer pH5.0 with $H_2O_2$, freshly prepared) and read rate of change in OD 650 over 2 minutes.

The elution profile of purified dGAE and purified T40 is shown in FIG. 34 (dGAE) and 35 (hT40). Although both these fragments typically run at about 12 kD and 55 kD respectively, about 64% of mAb 7.51 immunoreactivity (dGAE) elutes in fractions corresponding to species of size >15 kD and about 50% of mAb 499 immunoreactivity (hT40)eluted in fractions corresponding to species of size >60 kD. Thus the tau proteins are present, at least in part, in pre-aggregated form.

(ii) Effect of Tau Aggregation Inhibitors Measured Using Different Preparations of Tau Protein When the proteins dGA and dGAE were prepared as indicated above ("Preparation 2"), the properties of the tau-tau binding assay were altered relative to the properties obtained using the preparative method described in WO96/30766 ("Preparation 1").

The assay is performed using 96 well PVC plates (Falcon Cat. No. 353912 are used), and the following steps:

1. 50 μl dGA (~10 pg/ml) in carbonate buffer, incubate 1 h at 37° C.
   (Carbonate buffer: 50 mM carbonate bicarbonate, pH 9.6 ($Na_2CO_3$ 1.59 g/l, $NaHCO_3$ 2.93 g/l))
2. Wash plate in 0.05% Tween-20.
3. 200 μl PBS+2% Marvel, incubate 1 h at 37° C.
4. Rinse plate 2× in deoinised water, then wash in 0.05% Tween-20.
5. 50 μl dGAE (~10 μg/ml) plus drug in PBS+1% fish skin gelatin+0.05% Tween-20, incubate 1 h at 37° C.
6. Wash plate in 0.05% Tween-20.
7. 50 μl antibody 423 (1:10 dilution in PBS+2% Marvel), incubate 1 h at 37° C.
8. Rinse plate 2× in deionised water, then wash in 0.05% Tween-20.
9. 50 μl HRP-anti-mouse (1:1000 dilution in PBS+0.05% Tween-20), incubate 1 h at 37° C.
10. Wash plate in 0.05% Tween-20, then rinse 1× with deionised water.
11. 50 μl substrate solution, read immediately initial rate over 2 min in plate reader at OD650.
    (Substrate solution: 50 mM sodium acetate, pH 5.0+TMB (1 ml/100 ml of a 10 mg/ml solution in DMSO)+$H_2O_2$ (10 μl/100 ml)).

The compounds thionine and tolonium chloride were found to require higher concentrations to exert inhibitory effects in Preparation 2 than in Preparation 1. This is shown in FIGS. 36 and 37. Furthermore, the compound dimethyl methylene blue (DMMB) was found to have a higher inhibitory potency in Preparation 2 than in Preparation 1. This is Shown in FIG. 38.

As similar differences could be seen in Tau protein prepared by the Preparation 1 method, but which had been allowed to aggregate in vitro over time, the interpretation of this effect is as follows. Higher concentrations of compounds such as thionine and tolonium chloride are required since two effects have to be achieved in order to achieve maximal inhibition of tau-tau binding:

1. disruption of pre-existing aggregates in the aqueous-phase;
2. inhibition of binding of aqueous-phase species to the solid phase.

The greater potency of DMMB in the Preparation 2 assay can be explained by greater binding affinity at the site of action required for both inhibitory effects.

Full-length tau protein (hT40) prepared according to the Preparation 2 protocol demonstrated minimal tau-tau binding activity when used in the aqueous-phase with dGA in the solid-phase. However, when hT40 was used in the solid-phase, binding of dGAE was similar to that obtained for binding of dGAE to dGA in the solid-phase (see FIG. 39a-c). The interpretation is that in hT40 aggregates formed in the aqueous-phase tau-tau binding has already occurred in or through domains required for the binding interaction with dGA in the solid-phase. When hT40 is first plated in the solid-phase, the binding to PVC unfolds the protein/aggregates in such as manner as to make the critical tau-tau binding sites available.

(iii) Effect of Tau Aggregation Inhibitors Measured Using Different Preparations of Tau Protein In the Preparation 2 assay format, potent ligands of the kind typified by Primulin and Thiazin Red have no inhibitory activity on tau-tau binding. This is shown in FIG. 40 (cf. FIG. 10). Indeed in this assay, these compounds enhance tau-tau binding at concentrations greater than 100 μM (i.e. 100-fold molar ratio with respect to tau protein).

DMMB typically reduces tau-tau binding (with tau present typically at 1 μM) to 23% at DMMB 5 μM and 17% at DMMB 15 μM relative to that seen in the absence of DMMB.

Unexpectedly, this inhibitory effect can be completely reversed by co-incubation in the presence of increasing concentrations of high affinity ligands typified by Primulin and Thiazin Red. This is shown in FIG. 41.

Therefore, aggregated-tau ligands may be characterised functionally as compounds which do not themselves inhibit tau-tau binding, but block the inhibitory effects of potent inhibitors of tau-tau binding.

As can be seen in FIG. 42, inhibition of Tau-Tau binding produced by DMMB is progressively attenuated and reversed in the presence of increasing molar excess of Primulin. A similar effect can be shown for Thiazin Red. This indicates that the maximum inhibitory effect of DMMB is reduced by these compounds, and hence that they are acting as non-competitive inhibitors of DMMB. One possible explanation might be that the ligands stabilise the tau aggregates used in the assay, for example in regions outside the critical binding domain required for DMMB activity, and hence prevent the inhibitory effect of DMMB on Tau-Tau binding.

FIGS. 43-45 show that for any given concentration of DMMB, there is quantitative enhancement of Tau-Tau binding in the presence of Primulin (43, 44) or Thiazin Red (45) which can be modelled by a standard Michaelis-Menten equation. This implies that the Tau-aggregation enhancement effect of these ligands is proportional to the fraction of ligand-binding sites occupied, presumably within the Tau aggregates introduced into the aqueous-phase of the assay. The mean Bmax for both ligands is ~1.6. That is, the maximum ligand effect is to produce 1.6-fold the Tau-Tau binding signal seen in the absence of any drug. The mean Kd for this effect is ~15×. That is, for any given concentration of DMMB >4 μM, 50% of maximal enhancement of Tau-Tau binding can be seen when the ligand molar excess is 15-fold relative to the concentration of DMMB.

Example 8

Example Assays for Identifying Further Diagnostic Ligands Based on Ligands Provided Herein Having defined two classes of ligands as described above suitable for labelling PHFs in AD, further ligands can be developed using the compounds/derivatives in screening assays. Furthermore, modelling methods can be based on the ligands already presented.

(i) Identification of Novel Ligands at the Sulphonated-benzothiazole Site.

Using a suitably labelled preparation of a known sulphonated benzothiazole, incubated with a preparation of aggregated tau molecules (e.g. preaggregated tau in solution, or bound to a solid phase, or highly enriched PHFs isolated from AD brain—see WO96/30766) compounds suspected of being suitable ligands can be introduced, and their capacity to compete with the known ligand in such a way as to prevent binding within the PHF can be tested.

(ii) Identification of Novel Ligands at the Phenothiazine Site.

The tau-tau binding assay described in WO 96/30766 can be used as a preliminary screen to identify potential inhibitors at the tau-tau binding site. Likewise, a suitably-labelled preparation of known diaminophenothiazines, incubated with a aggregated tau as described above, could be used to screen for other compounds which are suspected of being competitors at this PHF-binding site and thus potentially suitable PHF ligands.

The physical implementation of competitive assays is well known in the art. It may include measurement of fluorescence, radioactivity or any other suitable reporting system which derives from sulphonated benzothiazole-like compounds or diaminophenothiazine-like compounds not bound to PHFs, i.e. those which remain in solution.

REFERENCES

1 DeToleda-Morrell, L. et al. (1997), Neurobiology of Aging 18, 5, 463-8;
2 De Leon et al. (1997), Neurobiol. Of Aging, 18, 1, 1-11;
3 Mori, E et al. (1997), Am. J. Psychiatry 154:1, p18;
4 Juottonen, K. (1998); J. Neurol. Neurosurg. Psychiatry 65, 322-327;
5 Bobinski, M. et al. (1999), Lancet 353, p. 38;
6 Fox, N. C. (1999) Neurol. 52, 1687-9;
7 Jack, C. R. et al. (1997) Neurol. 49: 786-794;
8 Fox, N. et al. (1996), Brain 119, 2001-7;
9 Johnson, K. A. et al. (1998), Neurol. 50, 1563-1571;
10 Perez-Tur, J. et al. (1999), Neurol. 53, 411-3;
11 Lehtovirta, M. et al. (1998) J. Neurol. Neurosurg. Psychiatry 64, 742-6;
12 Nagy, Zs et al. (1999), Dement. Geriatr. Cogn. Disord. 10, 109-114;
13 Ishii, K. et al. (1998), Neurol. 51, 125-130;
14 Imamura, T et al. (1997), Neurosci. Lett. 235, 49-52;
15 Minoshima, S. et al. (1997), Ann. Aurol. 42, 85-94;
16 Ibanez, V. et al. (1998), Neurol. 50, 1585-1593;
17 Wischik, C. W. et al. (2000) "Neurobiology of Alzheimer's Disease", Eds. Dawbarn et al., The Molecular and Cellular Neurobiology Series, Bios Scientific Publishers, Oxford)
18 Carretero, M. T. et al. (1995), Dementia 6, 281-5;
19 Villareal, D. T. et al. (1998), Alzheimer's Dis. Rev. 3, 142-152;
20 Marin, D. B. et al. (1998), Artherosclerosis 140, 173-180;
21 Kuller, L. H. et al. (1998), Stroke 29, 388-398;
22 Vargha-Khadem, F. et al. (1997), Science 277, p376;
23 Willingham, D. B. (1997), Neuron 18, 5-8;
24 Lakmache, Y. et al. (1995), PNAS USA 95, 9042-6;
25 Hodges, J. R. et al. (1999), PNAS USA 96, 9444-8;
26 Mena, R. et al. (1995), Acta Neuropathol. 89, 50-6;
27 Mena, R. et al. (1996), Acta Neuropathol. 91, 633-641;
28 (deleted)
29 Lai, R. et al. (1995) Neurobiol. Aging 16, 3, 433-445;
30 Bondareff, W. et al. (1994) J. Neuropathol. Exp. Neurol. 53, 2, 158-164;
31 Resch, J. F. et al. (1991) Bioorg. Med. Chem. Lett. 1, 10, 519-522;
32 Novak, M. et al. (1993), EMBO J. 12, 1, 365-370;
33 Wischik, C. W. et al. (1996), PNAS USA 93, 11213-8;
34 Wischik C. W. et al. (1989), Curr. Opin. Cell Biol. 1, 115-122;
35 WO 96/30766;
36 Muller, T. (1992), Acta Anat. 144, 39-44.

The invention claimed is:

1. A method for determining the Braak stage of neurofibrillary degeneration associated with a tauopathy in a subject having neurofibrillary degeneration, which method comprises the steps of:
(i) administering to the subject a ligand that labels aggregated paired helical filament (PHF) tau protein, wherein the ligand is capable of crossing the blood brain barrier,
wherein the ligand is conjugated, chelated, or otherwise associated, with a detectable chemical group, and
wherein the ligand is a compound of the formula:

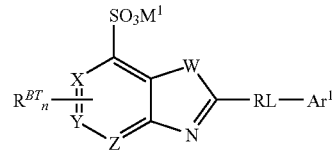

wherein:
W is S, O, or NH;
exactly one of X, Y, and Z is CH or N;
the others of X, Y, and Z are CH;
$M^1$ is an alkali metal cation selected from: Li, Na, K, or Cs;
RL is a rigid linker group;
$Ar^1$ is a $C_{5-20}$ aryl group;
n is an integer from 0 to 3; and,
each $R^{BT}$ is independently a core substituent selected from: $C_{1-4}$ alkyl, hydroxy, $C_{1-4}$ alkoxy, nitro, cyano, halo, or amino,
(ii) determining the presence and\or amount of ligand bound to extracellular aggregated PHF tau in the medial temporal lobe of the brain of the subject, and
(iii) correlating the result of the determination made in (ii) with the extent of neurofibrillary degeneration in the subject.

2. A method as claimed in claim 1 wherein the rigid linker group RL and the aryl group $Ar^1$ are substantially planar and the ligand has a twist that is no greater than the twist of the compound of FIG. 16.

3. A method as claimed in claim 1 wherein n is 1, and $R^{BT}$ is independently -Me, -Et, -nPr, or -iPr.

4. A method as claimed in claim 1 wherein RL is a group of the formula:

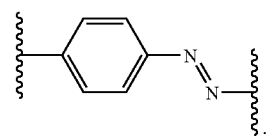

5. A method as claimed in claim 1 wherein $Ar^1$ is selected from:
groups derived from benzene ($C_6$), naphthalene ($C_{10}$), anthracene ($C_{14}$), phenanthrene ($C_{14}$), naphthacene ($C_{18}$), and pyrene ($C_{16}$);
$C_5$ heteroaryl groups derived from furan (oxole), thiophene (thiole), pyrrole (azole), imidazole (1,3-diazole), pyrazole (1,2-diazole), triazole, oxazole, isoxazole, thiazole, isothiazole, oxadiazole and oxatriazole;
$C_6$ heteroaryl groups derived from isoxazine, pyridine (azine), pyridazine (1,2-diazine), pyrimidine (1,3-diazine), pyrazine (1,4-diazine), triazine, tetrazole and oxadiazole (furazan);
$C_9$ heterocyclic groups derived from benzofuran, isobenzofuran, indole, isoindole, purine, benzimidazole;
$C_{10}$ heterocyclic groups derived from quinoline, isoquinoline, benzodiazine, pyridopyridine, quinoxaline;
$C_{13}$ heterocyclic groups derived from carbazole; and
$C_{14}$ heterocyclic groups derived from acridine, xanthene, phenoxathiin, phenazine, phenoxazine, phenothiazine.

6. A method as claimed in claim 5 wherein Ar¹ is an aryl group having a phenyl core, and has the formula:

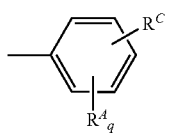

wherein
q is an integer from 0 to 5; and
each $R^A$ is independently an aryl substituent;
wherein each $R^A$ is independently selected from:
—OH, —NH$_2$, —NHR¹, —NR¹R², —SO$_3$M², and C$_{1-4}$alkyl;
wherein:
R¹ and R² are each 01-4 alkyl, and
M² is an alkali metal cation selected from Li, Na, K, or Cs
$R^C$, if present, is a reactive conjugating substituent, or
$R^C$ is, or contains, a detectable label;
and the compound has the formula:

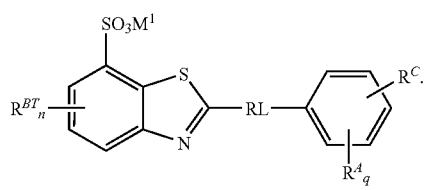

7. A method as claimed in claim 6 wherein $R^C$ is present and is a reactive conjugating substituent, and is, or contains,
a reactive functional group suitable for conjugation to another molecule by chemical reaction therewith, to form a covalent linkage there between, or
a moiety suitable for conjugation to another molecule by a strong non-covalent interaction, or
a moiety suitable for conjugation to another molecule by complex or chelate formation.

8. A method as claimed in claim 7 wherein $R^C$ is present and is, or contains, a technetium-chelating group.

9. A method as claimed in claim 6 wherein $R^C$ is present and is, or contains, a detectable label selected from: a dye, a fluorescent marker, an antigenic group, a stable or an unstable isotope, and a positron-emitting carbon atom.

10. A method as claimed in claim 1 wherein the ligand has the formula:

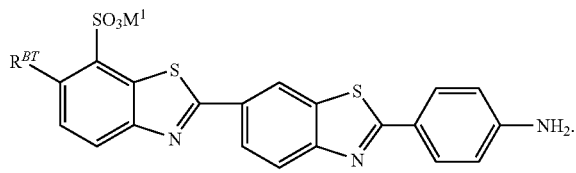

11. A method as claimed in claim 6 wherein Ar¹ is an aryl group having a hydroxy-substituted phenyl core, and has the formula:

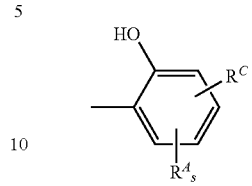

wherein
s is an integer from 0 to 4,
each $R^A$ is independently an aryl substituent, and
$R^C$, if present, is a reactive conjugating substituent, or
$R^C$ is, or contains, a detectable label.

12. A method as claimed in claim 11, wherein the ligand has the formula:

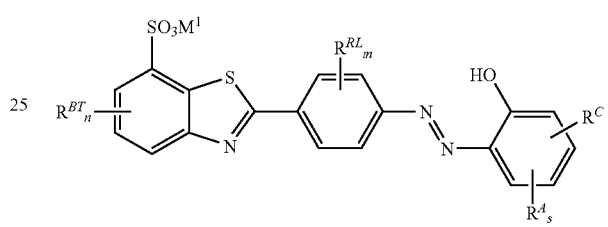

wherein:
M¹ is an alkali metal cation selected from Li, Na, K, or Cs;
n is an integer from 0 to 3;
each $R^{BT}$ is an independently benzothiazole substituent;
m is an integer from 0 to 4;
each $R^{RL}$ is independently a rigid linker aryl substituent;
s is an integer from 0 to 4;
each $R^A$ is independently an aryl substituent; and,
$R^C$, if present, is a reactive conjugating substituent, or
$R^C$ is, or contains, a detectable label.

13. A method as claimed in claim 12 wherein the ligand has the formula:

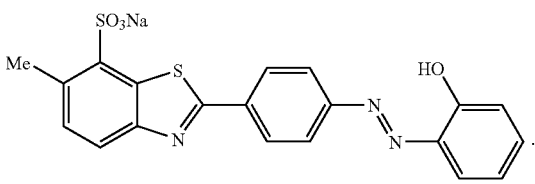

14. A method as claimed in claim 1 further comprising the step of administering to the subject a blocking ligand which labels competing non-aggregated tau binding sites present in the medial temporal lobe and in a neocortical structure of the brain, wherein the blocking ligand is a benzothiazole of the formula:

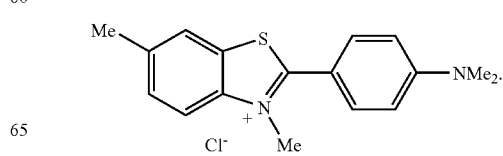

15. A ligand of the formula:

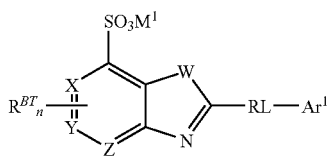

wherein:
W is S, O, or NH;
exactly one of X, Y, and Z is CH or N;
the others of X, Y, and Z are CH;
$M^1$ is an alkali metal cation selected from: Li, Na, K, or Cs;
RL is a rigid linker group;
$Ar^1$ is a $C_{5-20}$ aryl group;
n is an integer from 0 to 3; and,
wherein each $R^{BT}$ is independently $C_{1-4}$ alkyl.

16. A ligand as claimed in claim 15 wherein each $R^{BT}$ is independently -Me, -Et, -nPr or -iPr.

17. A ligand as claimed in claim 16 wherein each $R^{BT}$ is -Me.

18. A ligand as claimed in claim 16 wherein n is 1 and $R^{BT}$ is independently -Me, -Et, -nPr or -iPr.

19. A ligand as claimed in claim 18 wherein n is 1 and $R^{BT}$ is —Me.

20. A ligand of the formula:

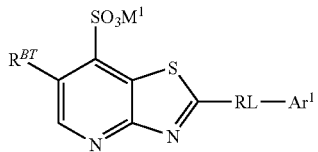

wherein:
$M^1$ is an alkali metal cation selected from: Li, Na, K, or Cs;
RL is a rigid linker group;
$Ar^1$ is a $C_{5-20}$ aryl group; and,
$R^{BT}$ is independently a core substituent selected from: $C_{1-4}$ alkyl, hydroxy, $C_{1-4}$ alkoxy, nitro, cyano, halo, or amino.

21. A ligand as claimed in claim 20 wherein the ligand has the following formula:

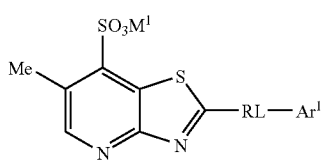

22. A ligand of the formula:

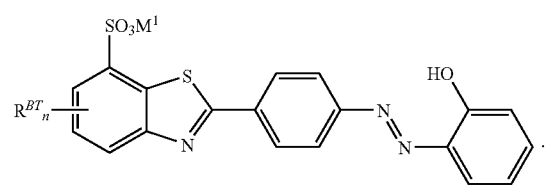

wherein:
$M^1$ is an alkali metal cation selected from: Li, Na, K, or Cs;
n is an integer from 0 to 3; and,
each $R^{BT}$ is independently a core substituent selected from: $C_{1-4}$ alkyl, hydroxy, $C_{1-4}$ alkoxy, nitro, cyano, halo, or amino.

23. A ligand as claimed in claim 22 wherein the ligand has the formula:

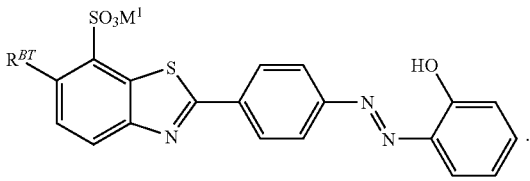

24. A ligand as claimed in claim 23 wherein the ligand has the formula:

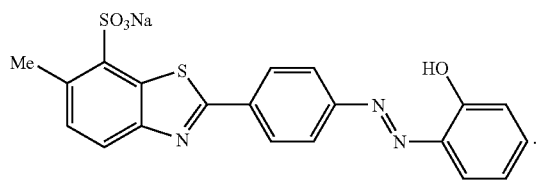

25. A ligand of the formula:

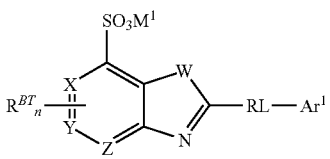

wherein:
W is S, O, or NH;
exactly one of X, Y, and Z is CH or N;
the others of X, Y, and Z are CH;
$M^1$ is an alkali metal cation selected from: Li, Na, K, or Cs;
RL is a rigid linker group;
$Ar^1$ is a $C_{5-20}$ aryl group;
n is an integer from 0 to 3; and,
each $R^{BT}$ is independently a core substituent selected from: $C_{1-4}$ alkyl, hydroxy, $C_{1-4}$ alkoxy, nitro, cyano, halo, or amino,
which is conjugated, chelated, or otherwise associated, with a detectable chemical group.

26. A diagnostic composition comprising as its active ingredient at least 90%, 95% or 98% of a ligand of the formula:

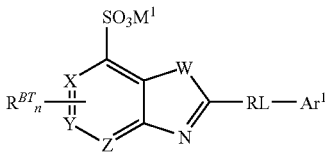

wherein:
W is S, O, or NH;
exactly one of X, Y, and Z is CH or N;
the others of X, Y, and Z are CH;
$M^1$ is an alkali metal cation selected from: Li, Na, K, or Cs;
RL is a rigid linker group;
$Ar^1$ is a $C_{5-20}$ aryl group;
n is an integer from 0 to 3; and,
each $R^{BT}$ is independently a core substituent selected from: $C_{1-4}$ alkyl, hydroxy, $C_{1-4}$ alkoxy, nitro, cyano, halo, or amino.

27. A diagnostic composition as claimed in claim 26 further comprising a carrier material or a pharmaceutically- and physiologically-acceptable excipient.

* * * * *